United States Patent
Adaniya et al.

(10) Patent No.: US 10,420,882 B2
(45) Date of Patent: Sep. 24, 2019

(54) METHOD AND SYSTEM FOR CONTROLLABLY ADMINISTERING FLUID TO A PATIENT AND/OR FOR CONTROLLABLY WITHDRAWING FLUID FROM THE PATIENT

(71) Applicant: MEDOVATE LIMITED, Cambridge (GB)

(72) Inventors: George Adaniya, Rockport, MA (US); Howard Donnelly, Needham, MA (US); Eric Mathews, Walpole, MA (US); Hayden Taylor, Windham, NH (US); Andrew Whitehead, Hingham, MA (US)

(73) Assignee: MEDOVATE LIMITED, Cambridge (GB)

( * ) Notice: Subject to any disclaimer, the term of this patent is extended or adjusted under 35 U.S.C. 154(b) by 656 days.

(21) Appl. No.: 14/777,119

(22) PCT Filed: Mar. 17, 2014

(86) PCT No.: PCT/US2014/030339
§ 371 (c)(1),
(2) Date: Sep. 15, 2015

(87) PCT Pub. No.: WO2014/145548
PCT Pub. Date: Sep. 18, 2014

(65) Prior Publication Data
US 2016/0030663 A1    Feb. 4, 2016

Related U.S. Application Data

(60) Provisional application No. 61/790,481, filed on Mar. 15, 2013.

(51) Int. Cl.
*A61M 5/14* (2006.01)
*A61M 5/145* (2006.01)
(Continued)

(52) U.S. Cl.
CPC ............ *A61M 5/145* (2013.01); *A61M 5/002* (2013.01); *A61M 5/1452* (2013.01);
(Continued)

(58) Field of Classification Search
CPC ................ A61M 5/1452; A61M 5/002; A61M 5/14216; A61M 5/14224; A61M 5/16877;
(Continued)

(56) References Cited

U.S. PATENT DOCUMENTS 4,296,406 A    10/1981 Pearson
4,300,554 A    11/1981 Hessberg et al.
(Continued)

FOREIGN PATENT DOCUMENTS

CN    203935468 U    11/2014
EP    2086480 B1    11/2010
(Continued)

OTHER PUBLICATIONS

Auroy et al., "Major Complications of Regional Anesthesia in France," Anesthesiology, 97(5): 1274-80 (2002).
(Continued)

*Primary Examiner* — Rebecca E Eisenberg
*Assistant Examiner* — Courtney B Fredrickson
(74) *Attorney, Agent, or Firm* — Michael Best & Friedrich LLP

(57) ABSTRACT

Method and system for controllably administering and/or withdrawing fluid from a patient. In one embodiment, the system may include a needle assembly, an ultrasound imager, a fluid supply storage unit, a waste storage unit, a fluid pump, and a foot pedal assembly. A syringe may serve as the fluid supply storage unit and the waste storage unit. The pump may include a bi-directional motor and a gear coupled to the motor. The gear may be engageable with a rack on the syringe plunger to drive the plunger either for
(Continued)

fluid aspiration or infusion. Depression of one portion of the foot pedal assembly causes the motor to drive the gear in one direction, and depression of another portion of the foot pedal assembly causes the motor to drive the gear the other direction. The system may include a control device to keep pressure in the fluid path from exceeding a limit.

32 Claims, 58 Drawing Sheets

(51) Int. Cl.
  *A61M 5/20* (2006.01)
  *A61M 5/00* (2006.01)
  *A61M 5/142* (2006.01)
  *A61M 5/168* (2006.01)
  *A61M 19/00* (2006.01)
(52) U.S. Cl.
  CPC .... *A61M 5/14216* (2013.01); *A61M 5/14232* (2013.01); *A61M 5/14526* (2013.01); *A61M 5/14546* (2013.01); *A61M 5/16877* (2013.01); *A61M 5/20* (2013.01); *A61M 19/00* (2013.01); *A61M 2205/12* (2013.01); *A61M 2205/502* (2013.01); *A61M 2205/505* (2013.01)
(58) Field of Classification Search
  CPC ...... A61M 2005/14212; A61M 5/1456; A61M 2005/14252; A61M 2205/3344; A61M 2205/3355
  See application file for complete search history.

(56) References Cited

U.S. PATENT DOCUMENTS

| 4,679,557 | A | * | 7/1987 | Opie | A61B 17/32002 |
| | | | | | 600/565 |
| 5,284,153 | A | | 2/1994 | Raymond et al. | |
| 5,284,154 | A | | 2/1994 | Raymond et al. | |
| 5,336,095 | A | | 8/1994 | Walburn et al. | |
| 5,573,515 | A | * | 11/1996 | Wilson | A61M 5/14216 |
| | | | | | 128/DIG. 12 |
| 5,808,203 | A | * | 9/1998 | Nolan, Jr. | A61M 5/14546 |
| | | | | | 604/67 |
| 5,830,151 | A | | 11/1998 | Hadzic et al. | |
| 5,910,135 | A | | 6/1999 | Hadzic et al. | |
| 6,003,736 | A | * | 12/1999 | Ljunggren | A61M 5/14244 |
| | | | | | 222/309 |
| 6,200,289 | B1 | | 3/2001 | Hochman et al. | |
| 6,520,928 | B1 | | 2/2003 | Junior | |
| 6,866,648 | B2 | | 3/2005 | Hadzic et al. | |
| 7,282,033 | B2 | | 10/2007 | Urmey | |
| 7,449,008 | B2 | * | 11/2008 | Hochman | A61M 5/1456 |
| | | | | | 604/67 |
| 7,624,953 | B2 | | 12/2009 | Silverman et al. | |
| 7,645,238 | B2 | | 1/2010 | Hirsch | |
| 7,689,292 | B2 | | 3/2010 | Hadzic et al. | |
| 7,727,224 | B2 | | 6/2010 | Hadzic et al. | |
| 8,027,718 | B2 | | 9/2011 | Spinner et al. | |
| 8,257,262 | B2 | | 9/2012 | Petersen et al. | |
| 2003/0167021 | A1 | * | 9/2003 | Shimm | A61M 5/14526 |
| | | | | | 600/554 |
| 2003/0225371 | A1 | * | 12/2003 | Hadzic | A61M 5/16854 |
| | | | | | 604/118 |
| 2004/0015124 | A1 | * | 1/2004 | Sciulli | A61M 5/14546 |
| | | | | | 604/67 |
| 2004/0059247 | A1 | | 3/2004 | Urmey | |
| 2004/0085215 | A1 | * | 5/2004 | Moberg | A61M 5/1456 |
| | | | | | 340/679 |
| 2004/0143223 | A1 | | 7/2004 | Spinello | |
| 2006/0270971 | A1 | | 11/2006 | Gelfand et al. | |
| 2007/0043339 | A1 | | 2/2007 | Horvath et al. | |
| 2007/0073155 | A1 | | 3/2007 | Park et al. | |
| 2007/0213676 | A1 | | 9/2007 | Popoalii | |
| 2007/0213771 | A1 | | 9/2007 | Spinner et al. | |
| 2008/0086088 | A1 | | 4/2008 | Malcolm | |
| 2009/0143734 | A1 | | 6/2009 | Humayun et al. | |
| 2009/0157113 | A1 | * | 6/2009 | Marcotte | A41D 13/1245 |
| | | | | | 606/191 |
| 2009/0299328 | A1 | | 12/2009 | Mudd et al. | |
| 2010/0164746 | A1 | * | 7/2010 | Mesika | H05C 1/00 |
| | | | | | 340/12.55 |
| 2011/0021905 | A1 | * | 1/2011 | Patrick | A61B 8/00 |
| | | | | | 600/424 |
| 2011/0060229 | A1 | | 3/2011 | Hulvershorn et al. | |
| 2011/0230838 | A1 | | 9/2011 | Adams et al. | |
| 2012/0245560 | A1 | * | 9/2012 | Hochman | A61M 5/20 |
| | | | | | 604/518 |
| 2012/0289891 | A1 | * | 11/2012 | Abdulreda | A61M 5/3148 |
| | | | | | 604/28 |
| 2014/0012226 | A1 | | 1/2014 | Hochman | |

FOREIGN PATENT DOCUMENTS

| WO | 9320751 | A1 | 10/1993 |
| WO | 9632156 | A1 | 10/1996 |
| WO | 2004075973 | A2 | 9/2004 |
| WO | 2007024399 | A2 | 3/2007 |
| WO | 2012082889 | A1 | 6/2012 |
| WO | 2012139035 | A1 | 10/2012 |
| WO | 2013160680 | A2 | 10/2013 |
| WO | 2014007949 | A1 | 1/2014 |

OTHER PUBLICATIONS

Urmey et al., "Inability to Consistently Elicit a Motor Response following Sensory Paresthesia during Interscalene Block Administration," Anesthesiology, 96(3): 552-4 (2002).

Borgeat et al., "Evaluation of the Lateral Modified Approach for Continuous Interscalene Block after Shoulder Surgery," Anesthesiology, 99:436-42 (2003).

Kudo, "Initial Injection Pressure for Dental Local Anesthesia: Effects on Pain and Anxiety," Anesthesia Progress, 52:95-101 (2005).

* cited by examiner

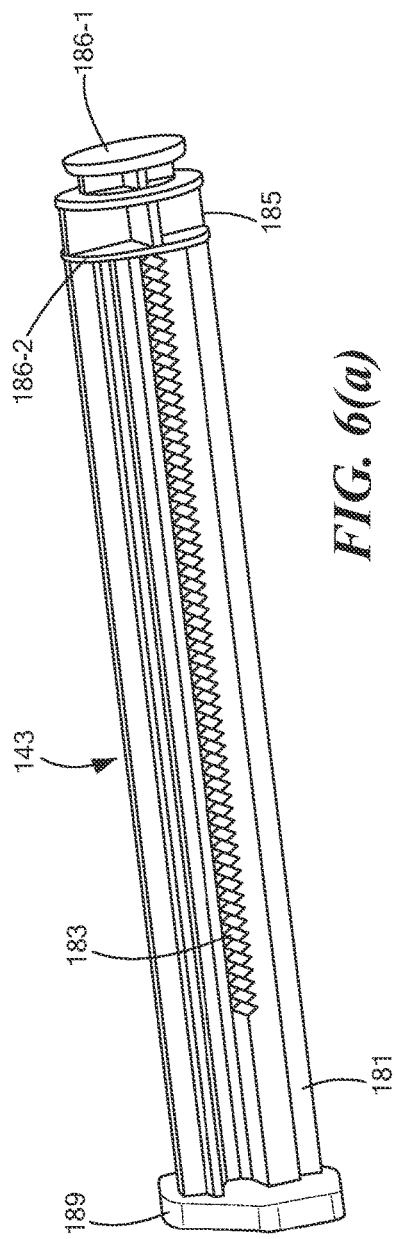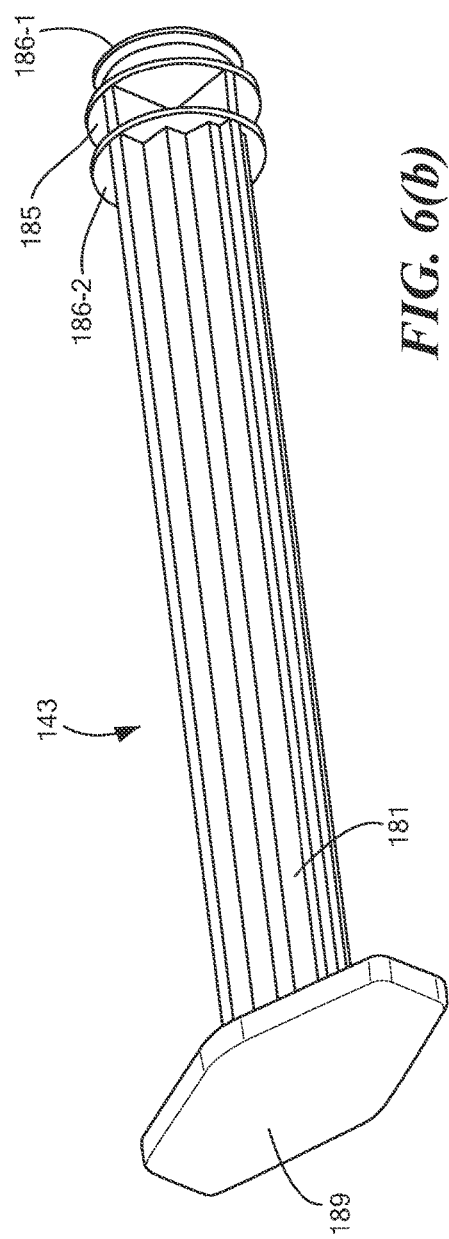

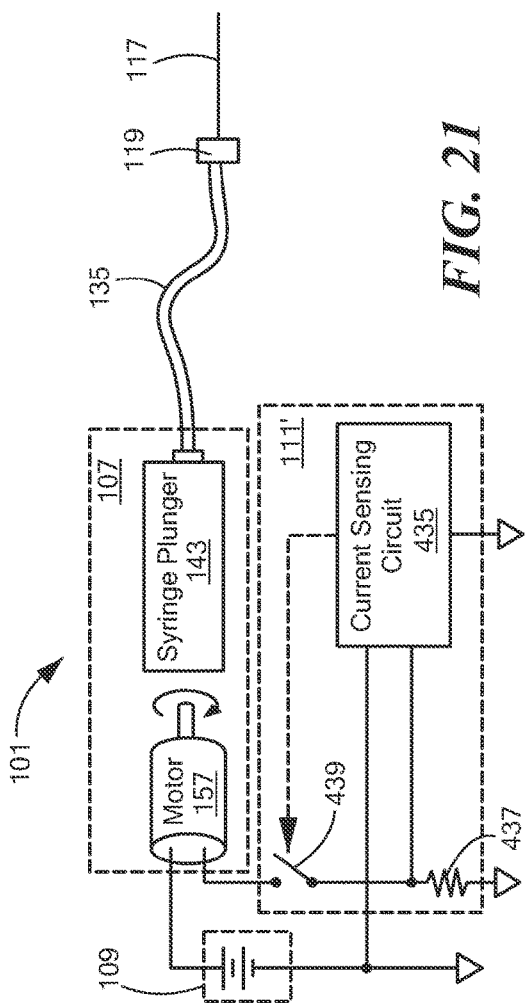
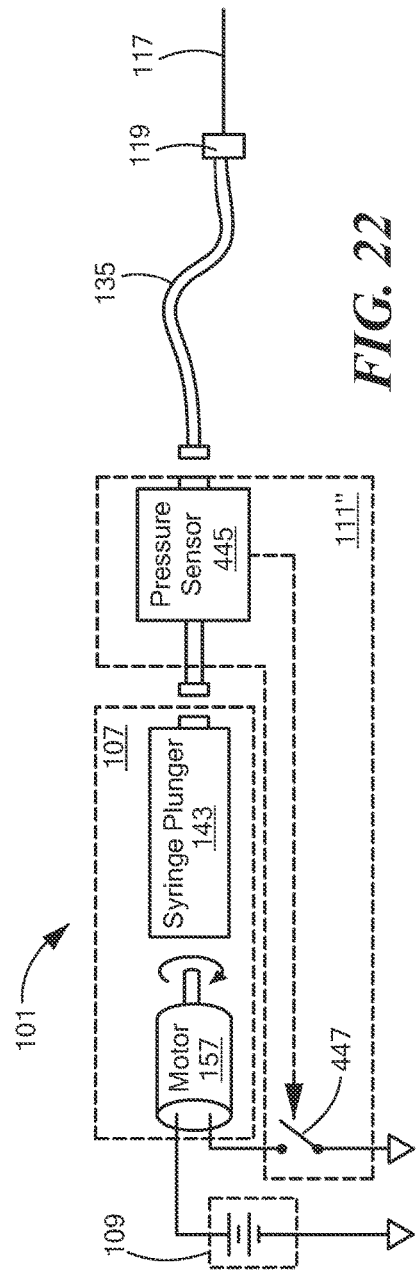
FIG. 21
FIG. 22

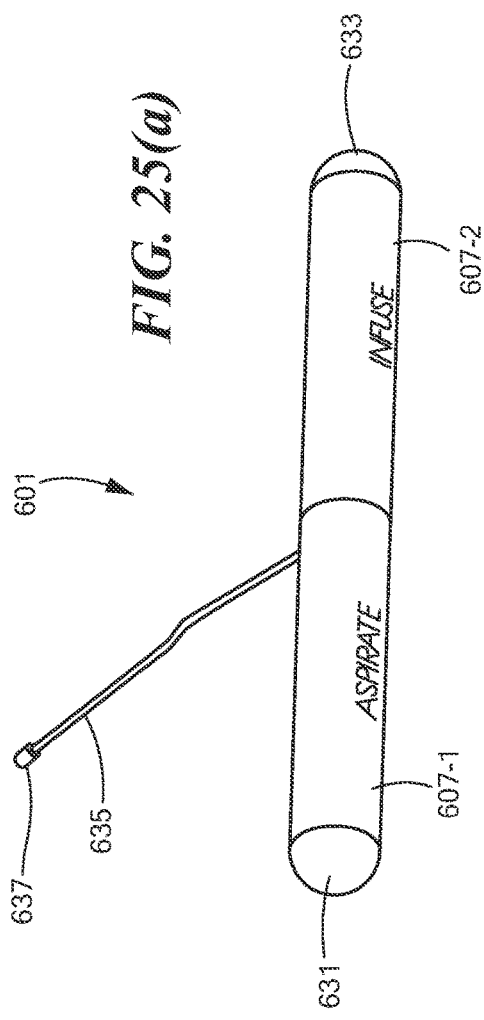
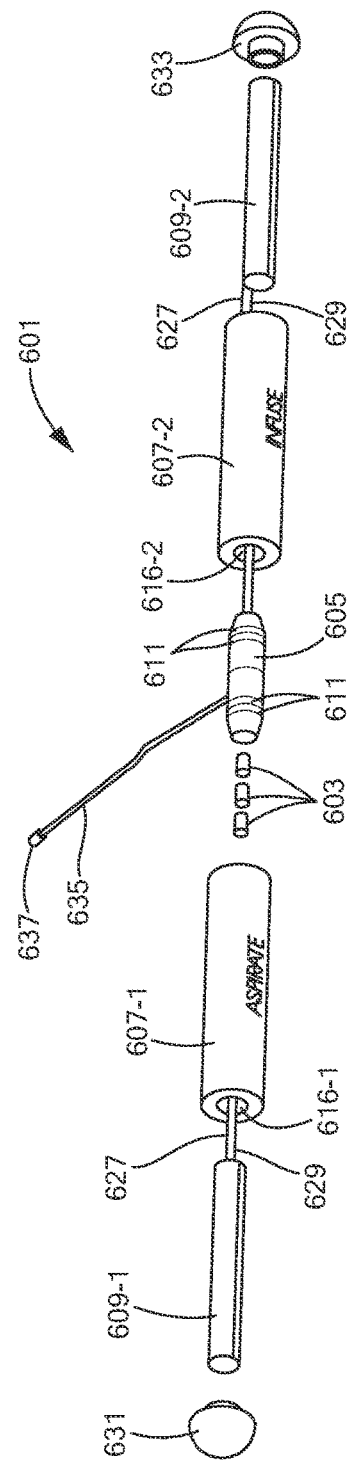
FIG. 25(a)
FIG. 25(b)

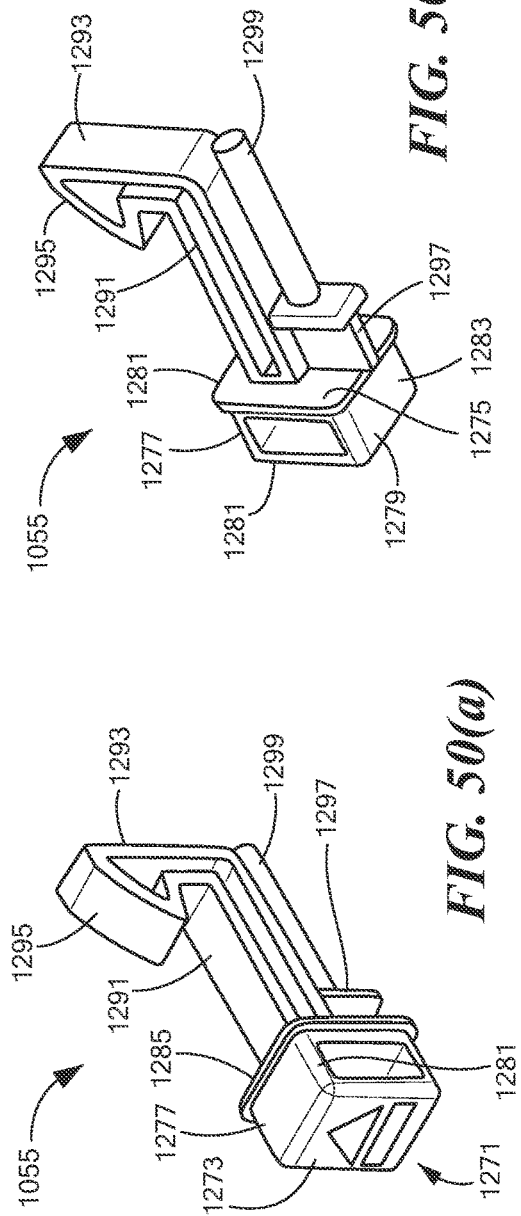
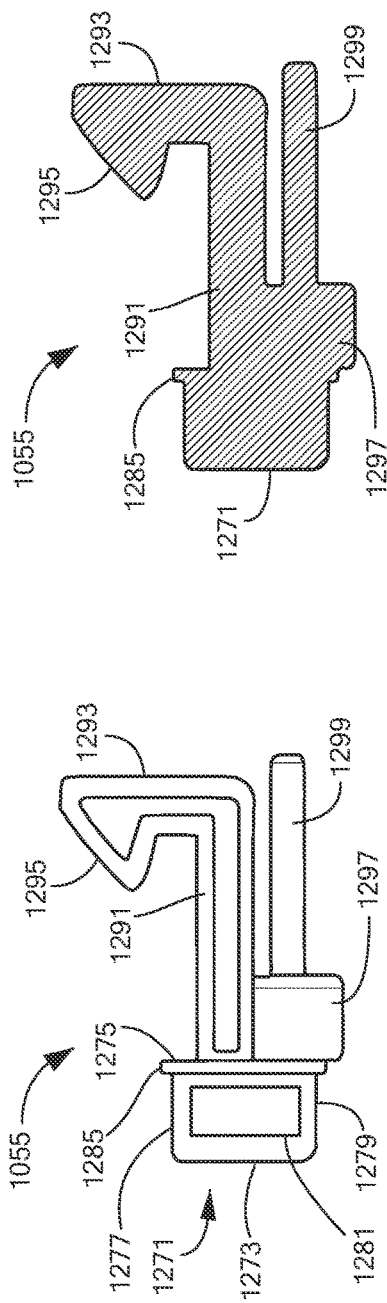

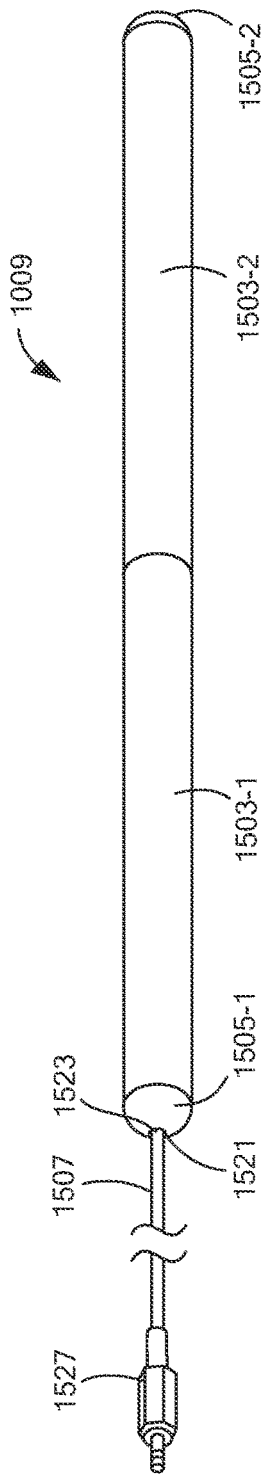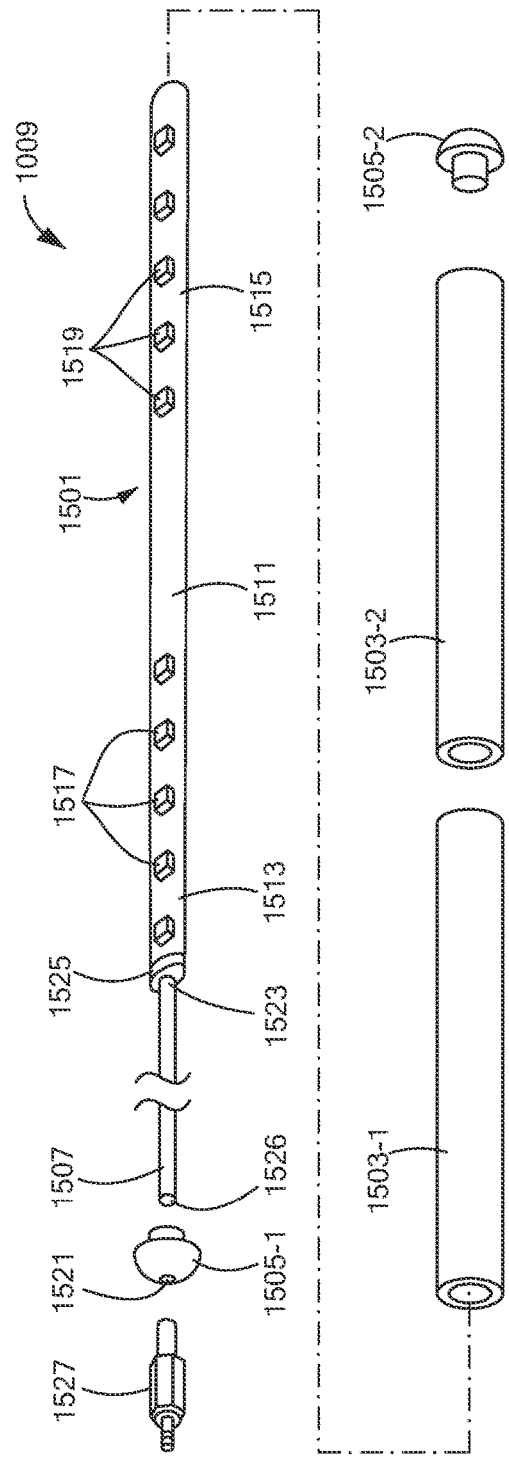
FIG. 54(a)
FIG. 54(b)

METHOD AND SYSTEM FOR CONTROLLABLY ADMINISTERING FLUID TO A PATIENT AND/OR FOR CONTROLLABLY WITHDRAWING FLUID FROM THE PATIENT

BACKGROUND OF THE INVENTION

The present invention relates generally to the administration of fluid to a patient or to the withdrawal of fluid from a patient and relates more specifically to a method and system for controllably administering fluid to a patient and/or for controllably withdrawing fluid from the patient.

There are many situations in which it may be desirable to administer one or more fluids to a patient or to withdraw one or more fluids from a patient. An example of one such situation involves the administration of regional anesthesia to a patient. In contrast to general anesthesia, which is a systemic sedation of a patient, regional anesthesia is the administration of medication to specific body regions by anesthetizing specific nerves, thereby permitting the patient to block pain and to be cognitively alert or conscious. Regional anesthesia may be used to treat pain during surgery and during post-surgery recovery and may also be used to provide patients with extended relief of longer-term pain. Because regional anesthesia is not systemic, regional anesthesia increase patient safety and satisfaction and, concurrently, reduces anesthesia cost. Regional anesthesia is an effective technique for selectively anesthetizing a specific region of the body without interfering with a patient's vital systems.

Traditionally, regional anesthesia involves the use of a specialty regional anesthesia needle, which the physician uses to infuse medication in close proximity to the target nerves to be blocked, i.e., anesthetized. The physician may insert the needle blindly, using anatomical landmarks of the patient in an attempt to locate the nerve to be blocked. If the needle tip is more than 5 mm from the nerve, the anesthesia may be ineffective. If the needle tip touches the nerve, such contact of the nerve by the needle tip may cause nerve damage. With effective manual needle insertion and infusion, the patient experiences paresthesia, a buzzing tingling sensation, which is usually orally reported by the patient to the physician.

As can be appreciated, the success rate of a blindly-located nerve block is lowered if the patient's feedback to the physician during the needle insertion procedure is inaccurate or if the patient is disoriented or unresponsive. To minimize the likelihood of an errant positioning of the infusion needle, certain devices have been used to help position the needle in proximity to the body portion that one wishes to target. One such device is a nerve stimulator, which provides electrical current to the infusion needle and which causes a body portion contacted by the needle to twitch, thereby providing a visual indicator to the physician of the location of the needle. Examples of nerve stimulators are disclosed in the following documents, all of which are incorporated herein by reference: U.S. Pat. No. 5,284,153, inventors Raymond et al., issued Feb. 8, 1994; U.S. Patent Application Publication No. US 2007/0213771 A1, inventors Spinner et al., published Sep. 13, 2007; U.S. Patent Application Publication No. US 2004/0059247 A1, inventor Urmey, published Mar. 25, 2004; European Patent Application Publication No. EP 0 957 982 A1, published Nov. 24, 1999; and European Patent Application Publication No. EP 0 637 934 A1, published Feb. 15, 1995.

Another device that is commonly used, either in place of a nerve stimulator or in combination therewith, to help position in infusion needle in proximity to a body portion that one wishes to target is a handheld ultrasonic imager. Examples of handheld ultrasonic imagers are disclosed in the following documents, all of which are incorporated herein by reference: U.S. Pat. No. 8,257,262 B2, inventors Petersen et al., issued Sep. 4, 2012; U.S. Pat. No. 7,645,238 B2, inventor Hirsch, issued Jan. 12, 2010; and U.S. Patent Application Publication No. US 2007/0073155 A1, inventors Park et al., published Mar. 29, 2007.

One of the shortcomings associated with administering regional anesthesia to a patient in the manner described above is that typically more than one person is needed to perform the procedure. This is because, for example, the physician may use one hand or both hands to position the needle in the patient or may use one hand to position the needle in the patient and may use another hand to hold a handheld ultrasonic imager, a nerve stimulator, or another device used to help locate the needle in the patient. As a result, a nurse or other assistant is typically needed to operate the syringe or other fluid flow device coupled to the infusion needle, typically by a length of tubing, so that the desired quantity of anesthesia may be dispensed through the infusion needle.

In addition, despise the advent of techniques to help position the needle correctly, the needle tip may inadvertently be inserted into a nerve. As can be appreciated, if insertion of the needle tip into a nerve occurs, any subsequent injection of anesthesia into the nerve may cause significant injury to the nerve. Such injury to the nerve can be either mechanical or ischemic trauma due to an increase in endoneural pressure caused by the fluid injected and/or endoneural edema. In view of the above, current recommendations are for the syringe operator to avoid high injection pressures. However, a determination of when an injection pressure is, in fact, dangerously high has traditionally been based simply on a subjective feel of the syringe by the syringe operator, without any accompanying objective measurement of the actual injection pressure. Such a subjective assessment by the syringe operator is further complicated by the differences in hand strength among different users and by the multitude of needle types, needle lengths, and needle lumen calibers, all of which can affect an interpretation of what is too forceful or too fast.

In an attempt to address some, but not all, of the above issues, there is disclosed a method and apparatus to decrease the risk intraneuronal injection during administration of nerve block anesthesia in U.S. Pat. No. 6,866,648 B2, inventors Hadzic et al., issued Mar. 15, 2005, which is incorporated herein by reference. More specifically, the aforementioned patent teaches the provision of a pressure sensing device located between an injection device (typically a syringe) and a nerve block needle whereby injection pressure during a nerve block injection can be easily and objectively monitored, thereby allowing the operator to monitor the injection pressure and/or injection speed during a nerve blockage injection procedure and to take appropriate corrective actions if abnormal pressure conditions are observed.

Other document that may be of interest include the following, all of which are incorporated herein by reference: U.S. Pat. No. 7,727,224 B2, inventor Hadzic et al., issued Jun. 1, 2010; U.S. Pat. No. 7,689,292 B2, inventors Hadzic et al., issued Mar. 30, 2010; U.S. Pat. No. 5,910,135, inventors Hadzic et al., issued Jun. 8, 1999; U.S. Pat. No. 5,830,151, inventors Hadzic et al., issued Nov. 3, 1998; PCT International Publication No. WO 2012/139035 A1, published Oct. 11, 2012; European Patent Application Publication. No. EP 1 599 135 A2, published Nov. 30, 2005; Steinfeldt et al., "Forced Needle Advancement During Needle-Nerve Contact is a Porcine Model: Histological Outcome," *Anesth. Analg.*, 113:417-20 (2011); ASRA News, May 2009 Newsletter, a Publication of the American Society of Regional Anesthesia and Pain Medicine; Theron et al., "An Animal Model of 'Syringe Feel' Daring Peripheral Nerve Block," *Reg. Anesth. Pain Med.*, 34(4):330-2 (2009); Robards et al., "Intraneural Injection with Low-Current Stimulation During Popliteal Sciatic Nerve Block," *Anesth Analog.*, 109:673-7 (2009); Gerancher et al., "Development of a Standardized Peripheral Nerve Block Procedure Note Form," *Reg. Anesth. Pain Med.*, 30(1):67-71 (2005); Claudio et al., "Injection Pressures by Anesthesiologist During Simulated Peripheral Nerve Block," *Reg. Anesth. Pain Med.*, 29(3):201-5 (2004); Hadzic et al., "Combination of Intraneural Injection and High Injection Pressure Leads to Fascicular Injury and Neurologic Deficit in Dogs," *Reg. Anesth. Pain Med.*, 29(5):417-23 (2004); Auroy et al., "Major Complications of Regional Anesthesia in France," *Anesthesiology*, 97:1274-80 (2002); Urmey et al., "Inability to Consistently Elicit a Motor Response following Sensory Paresthesia during Interscalene Block Administration," *Anesthesiology*, 96:552-4 (2002); Borgeat et al., "Evaluation of the Lateral Modified Approach for Continuous Interscalene Block after Shoulder Surgery," *Anesthesiology*. 99:436-42 (2003); and ASRA News, May 2007 Newsletter, a Publication of the Americas Society of Regional Anesthesia and Pain Medicine.

SUMMARY OF THE INVENTION

It is an object of the present invention to provide a new method and system for controllably administering fluid to a patient and/or for controllably withdrawing fluid from the patient.

It is another object of the present invention to provide a method and system as described above that overcomes at least some of the deficiencies of existing methods and systems.

According to one aspect of the invention, there is provided a system for controllably administering fluid to a patient and/or for controllably withdrawing fluid from the pattern, the system comprising (a) an infusion needle; (b) a pump adapted to be operably coupled to the infusion needle for creating fluid flow through the infusion needle; and (c) a hands-free switch for activating and/or deactivating the pump.

According to another aspect of the invention, there is provided a system for controllably administering fluid to a patient and/or for controllably withdrawing fluid from the patient, the system comprising (a) a syringe, the syringe comprising a syringe body and a syringe plunger; (b) an infusion needle, the infusion needle being operatively coupled to the syringe; (c) a pump, the pump comprising a motor and a gear, the gear being engageable with the syringe plunger to drive movement of the syringe plunger relative to the syringe body; (d) an adaptor for selectively engaging the gear and the syringe plunger; and (e) a hands-free switch for activating and/or deactivating the motor.

According to still another aspect of the invention, there is provided a method for controllably administering fluid to a patient and/or for controllably withdrawing fluid from the patient, the method comprising (a) providing the above-described system; (b) positioning the infusion needle at a desired location within the patient; (c) using the hands-free switch to activate and to deactivate the pump. In a further, more detailed aspect of the invention, the system may further comprise a control device for automatically preventing the fluid pressure in the infusion needle from exceeding a predetermined threshold.

According to yet another aspect of the invention, there is provided a foot-operable switch, the foot-operable switch comprising (a) a resiliently-compressible tube having a void; (b) a resiliently-compressible circuit roll disposed in the void, the resiliently-compressible circuit roll comprising a sheet of electrically-insulating material and two electrically-conductive elements on the sheet of electrically-insulating material, the two electrically-conductive elements being arranged on the sheet so as to make contact with one another when the resiliently-compressible tube is compressed.

According to still yet another aspect of the invention, there is provided a kit, the kit comprising (a) a first container; (b) a syringe disposed within the first container; (c) a pump disposed within the first container, the pump being adapted to pump fluid into and/or out of the syringe; and (d) a second container, the first container being disposed within the second container, the second container being a blister pack container into which is incorporated at least one foot pedal adapted for operating the pump.

According to a further aspect of the invention, there is provided a kit, the kit comprising (a) a first container; (b) a syringe disposed within the first container; (c) a pump disposed within the first container, the pump being adapted to pump fluid into and/or out of the syringe; and (d) a foot pedal adapted for operating the pump.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 6(a) and 6(b) are enlarged distal perspective and enlarged proximal perspective views, respectively, of the syringe plunger shown in FIG. 3(b);

FIG. 21 is a simplified schematic representation a second exemplary embodiment of the control device of FIG. 2, the second exemplary embodiment of the control device being shown as part of a simplified rendering of the system of FIG. 2;

FIG. 22 is a simplified schematic representation of a third exemplary embodiment of the control device of FIG. 2, the third exemplary embodiment of the control device being shown as part of a simplified rendering of the system of FIG. 2;

FIGS. 25(a) and 25(b) are perspective and partly exploded perspective views, respectively, of a foot pedal assembly tor use in the system of FIG. 2;

FIGS. 50(a) through 50(d) are top perspective, bottom perspective, side, and longitudinal section views, respectively, of the locking clip shown in FIG. 45;

FIGS. 54(a) and 54(b) are fragmentary perspective and fragmentary partly exploded perspective views, respectively, of the foot pedal assembly shown in FIG. 45;

DETAILED DESCRIPTION OF THE INVENTION

The present invention is directed at a method sod system for controllably administering fluid to a patient and/or for controllably withdrawing fluid from the patient. An exemplary and non-limiting application of the method and system of the present invention is in the field of regional anesthesia, where the method and system may be used to inject an anesthetizing fluid into a specific region of the patient, for example, to effect a nerve blockage. In addition, the method and system of the present invention may also be used to aspirate fluid from the patient, for example, to ascertain whether a needle that has been inserted into the patient in order to administer anesthesia to a nerve has been properly placed or has been misplaced, for example, its a blood vessel. The aforementioned injection and aspiration procedures of the present method and system can be performed on the same patient, albeit sequentially, as opposed to simultaneously.

Figure 1:
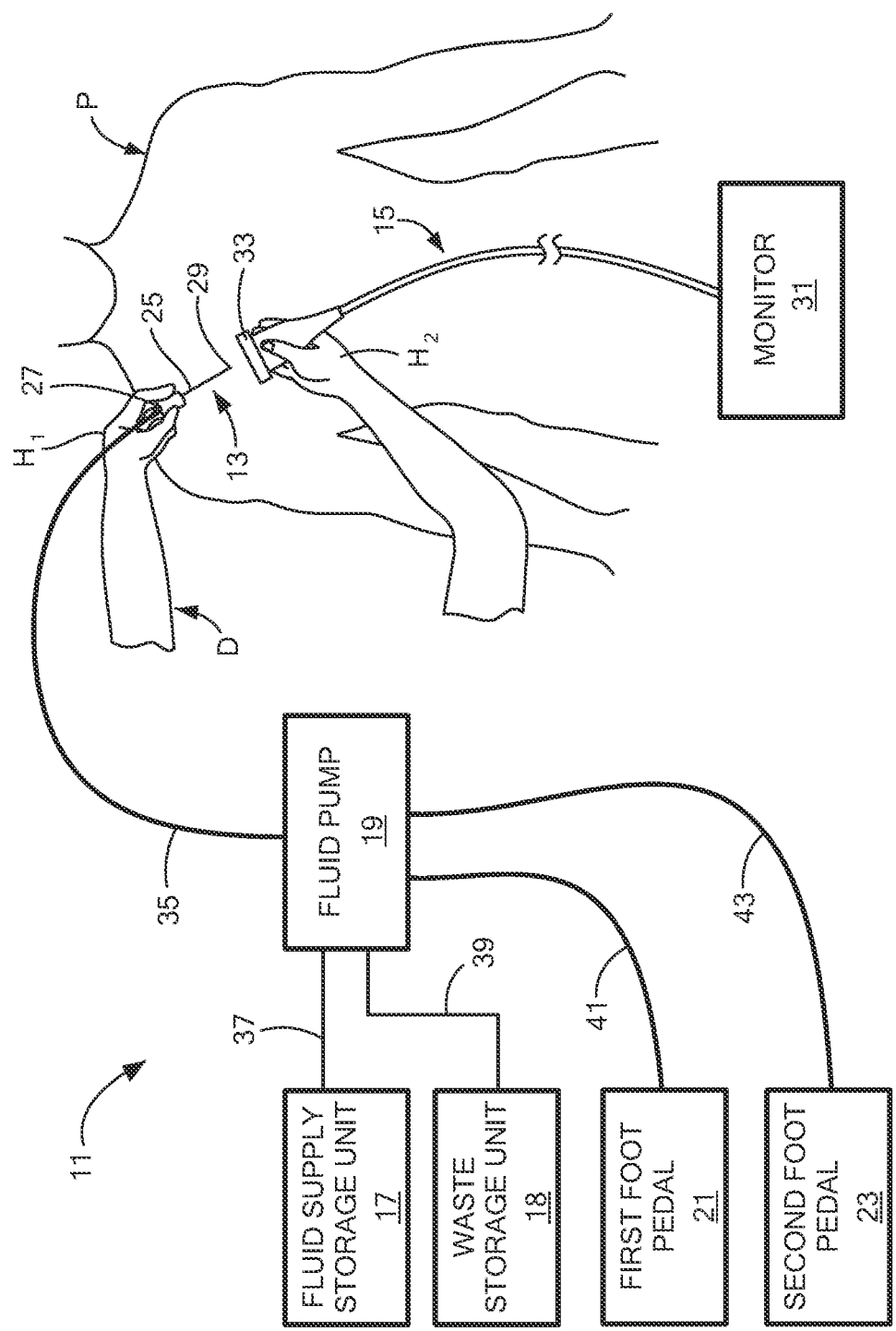
FIG. 1 is a schematic representation of a first embodiment of a system according to the present invention for controllably administering fluid to a patient and/or for controllably withdrawing fluid from the patient.

Referring now to FIG. 1, there is schematically shown a first embodiment of a system according to the present invention for controllably administering fluid to a patient and/or for controllably withdrawing fluid from the patient, the system being represented generally by reference numeral 11. System 11 is shown in FIG. 1 being used by a doctor D on a patient P.

System 11 may include one or more of an infusion needle assembly 13, a handheld ultrasound imager 15, a fluid supply storage unit 17, a waste storage unit 18, a fluid pump 19, a first foot pedal 21, and a second foot pedal 23. Each of the foregoing components will now be discussed further below.

Infusion needle assembly 13 may be conventional and may include an infusion needle 25 and a needle hub 27. Infusion needle 25, which may be a generally tubular member having a sharpened distal end 29, may have a length of, for example, approximately 25 mm to approximately 150 mm and may have an outer diameter of, for example, approximately 25 gauge to approximately 18 gauge. Needle hub 27, which may be a generally tubular or otherwise finger graspable member, may be coaxially positioned around and fixed to infusion needle 25. In use, doctor D may grasp needle hub 27 in a first hand $H_1$, then may insert distal end 29 of infusion needle 25 into patient P through a desired entry site, and then may guide distal end 29 of infusion needle 25 to a desired destination within the body of patient P.

Handheld ultrasound imager 15 may be conventional and may be used by doctor D to observe, in real-time, on a monitor 31 the location of infusion needle 25 within patient P. In use, doctor D may hold a probe 33 of handheld ultrasound imager 15 in a second hand $H_2$ and may position probe 33 against patient P so that infusion needle 25 may be observed on monitor 31. (Although not shown in FIG. 1, infusion needle assembly 13 may alternatively or additionally include a nerve stimulator lead, which may be connected at one end to infusion needle 25 and at an opposite end to a source of electrical current and which may be used to cause a body portion contacted by infusion needle 25 to involuntarily twitch, thereby providing a visual indicator to the doctor of the location of infusion needle 25. One hand of the doctor may be used to guide and to provide fine control of distal end 29 of infusion needle 25, and the other hand may be used to adjust the stimulator.)

Fluid supply storage unit 17 may be a receptacle suitable for holding a quantity of the fluid one wishes to inject into patient P through infusion needle 25. Fluid supply storage unit 17 may comprise, for example, a syringe, a fluid pouch, such as an I.V. bag, or some other fluid receptacle. Fluid supply storage unit 17 may hold a quantity of a suitable fluid, which fluid may be, for example, a conventional anesthetizing fluid.

Waste storage unit 18 may be a suitable receptacle for holding a quantity of the fluid one wishes to withdraw from patient P through infusion needle 25. Waste storage unit 18 may comprise, for example, a syringe, a fluid pouch, or some other fluid receptacle.

If desired, for example, depending on the type of procedure being performed, the same receptacle may be used, albeit at different points in time, both as fluid supply storage unit 17 and as waste storage unit 18.

Fluid pump 19 may be a bi-directional pumping device that may be adapted so cause fluid to flow from fluid supply storage unit 17 to infusion needle 25 and that may alternatively be adapted to cause fluid to flow from infusion needle 25 to waste storage unit 18. More specifically, when used in one mode of operation, fluid pump 19 may cause fluid to flow from fluid supply storage unit 17 to infusion needle 25, and, when used in another mode cooperation, fluid pump 19 may cause fluid to flow from infusion needle 25 to waste storage unit 18. Fluid pump 19 may be positioned, as shown, in-line between fluid supply storage unit 17 and infusion needle assembly 13 using a first tubing 35 and a second tubing 37 and in-line between waste storage unit 18 and infusion needle assembly 13 using first tubing 35 and a third tubing 39. (Where the same receptacle is used as fluid supply storage unit 17 and as waste storage unit 18, third tubing 39 may be eliminated.) Alternatively, instead of being positioned in-line between fluid supply storage unit 17 and infusion needle assembly 13 and in-line between waste storage unit 18 and infusion needle assembly 13, fluid pump 19 may be positioned elsewhere, for example, so that fluid supply storage unit 17 is positioned between fluid pump 19 and needle infusion assembly 13 and so that waste storage unit 18 is positioned between fluid pump 19 and needle infusion assembly 13.

Fluid pump 19 may be electrically powered, for example, using alternating current or direct current (e.g., one or more batteries). Fluid pump 19 may include some mechanism for shutting down (i.e., stopping operation or stalling) when the fluid pressure within the fluid path exceeds some predetermined threshold value. In this manner, for example, if infusion needle 25 experiences an unexpected blockage, such as may occur if infusion needle 25 is inadvertently inserted into a nerve, thereby causing the field pressure within the fluid path to exceed the predetermined threshold value, fluid pump 19 will stop pumping fluid from fluid supply storage unit 17 to needle 25. Where system 11 is being used to anesthetize a nerve, the threshold value for shutting down fluid pump 19 may be, for example, approximately 10 psi to approximately 20 psi, preferably approximately 15 psi to approximately 20 psi. The shutdown mechanism for fluid pump 19 may comprise, for example, arty mechanism (e.g., mechanical, electrical, electromechanical, magnetomechanical, etc.) that is triggered when the fluid pressure within the fluid path exceeds the predetermined threshold.

First foot pedal 21 may be coupled to fluid pump 19 in such a way that actuation of first foot pedal 21 causes fluid pump 19 to operate by pumping fluid from fluid supply storage unit 17 to infusion needle 25. Where fluid pump 19 is a pump of the type that is electrically powered, first foot pedal 21 may be connected to fluid pump 19 by a wire 41 and may be used to close a switch that causes fluid pump 19 to pump fluid from fluid supply storage unit 17 to infusion needle 25. First foot pedal 21 may be a conventional foot pedal but is not limited to a conventional foot pedal and may encompass any switching mechanism that may be operated by foot.

Second foot pedal 23 may be coupled to fluid pump 19 in such a way that actuation of second foot pedal 23 causes fluid pump 19 to operate by pumping fluid from infusion needle 25 to waste storage unit 18. Where fluid pump 19 is a pump of the type that is electrically powered, second foot pedal 23 may be connected to fluid pump 19 by a wire 43 and may be used to close a switch that causes fluid pump 19 to pump fluid from infusion needle 25 to waste storage unit 18. Second foot pedal 23 may be a conventional foot pedal but is not limited to a conventional foot pedal and may encompass any switching mechanism that may be operated by foot.

Although first foot pedal 21 and second foot pedal 23 are shown in FIG. 1 being coupled to fluid pump 19 by wires 41 and 43, respectively, it can readily be appreciated that wires 41 and 43 may be replaced by any wireless means including, but not limited to, using Bluetooth communications to connect foot pedals 21 and 23 to fluid pump 19 or using voice command and recognition electronics within a control module to control the application of power to the motor of fluid pump.

In use, doctor D may use first hand $H_1$ both to insert infusion needle 25 into patient P and to guide infusion needle 25 to the desired location within patient P. Doctor D may use second hand $H_2$ to operate handheld ultrasound imager 15 so that infusion needle 25 may be observed during its placement. If doctor D wishes to aspirate fluid from the patient, doctor D may step on second foot pedal 23. If doctor D wishes to inject a fluid, such as anesthesia, through infusion needle 25, doctor D may step on first foot pedal 21. If the pressure within the fluid path exceeds the threshold value at any time when first foot pedal 21 or second foot pedal 23 is depressed, fluid pump 19 will shut down, stopping any injection or aspiration.

As can be appreciated, one of the benefits of system 11, as compared to conventional injection needle systems, is that system 11 does not require, for its operation, the participation of a plurality of individuals, but rather, may be operated by a single individual, such as a physician. For example, the physician may hold infusion needle assembly 13 in first hand $H_1$ and may hold handheld ultrasound imager 15 in second hand $H_2$, observing the positioning of infusion needle 25 on monitor 31. Then, to inject fluid into patient P through infusion needle 25, or to aspirate fluid from patient P through infusion needle 25, the physician may merely step on first foot pedal 21 or on second foot pedal 23, respectively. In so doing, the physician does not need to remove his hands from infusion needle assembly 13 or from handheld ultrasound imager 15.

Moreover, where, as in the present embodiment fluid pump 19 includes a mechanism that automatically causes pumping to slop when the fluid pressure within the fluid path exceeds a predetermined threshold, system 11 may enable one to avoid the undesirable consequences resulting from excessively high fluid pressures and obviates the need for one to actively monitor the fluid pressure during injection or aspiration to ensure that excessively high fluid pressures are not reached.

Therefore, where system 11 is used by a physician to perform a nerve block procedure, system 11 enables the physician to perform the nerve block without the assistance of other individuals. This is because system 11 enables the physician to control the infusion and aspiration of fluids through the infusion needle without using his hands, which are typically required for the fine control of adjusting the needle tip location and for the manipulation of the position and/or controls of a needle tip monitoring device. Moreover, system 11 can minimize nerve damage by limiting the pressure of the fluid medication to less than the threshold at which neuronal damage to the nerve is induced.

If desired, one or more components of system 11 and, in some cases, all of the components of system 11, except possibly for handheld ultrasound imager 15, may be disposable, single-use items. This single-use may be desirable as it may provide a convenient way of ensuring the sterility of system 11 in an operating room or surgery center environment.

As can be appreciated, system 11 may be modified to provide only the capacity to inject fluid or only the capacity to aspirate fluid. If so modified, the components of system 11 pertaining to the eliminated function may be omitted, and fluid pump 19 may be modified to pump fluid in only the corresponding direction.

Figure 2:
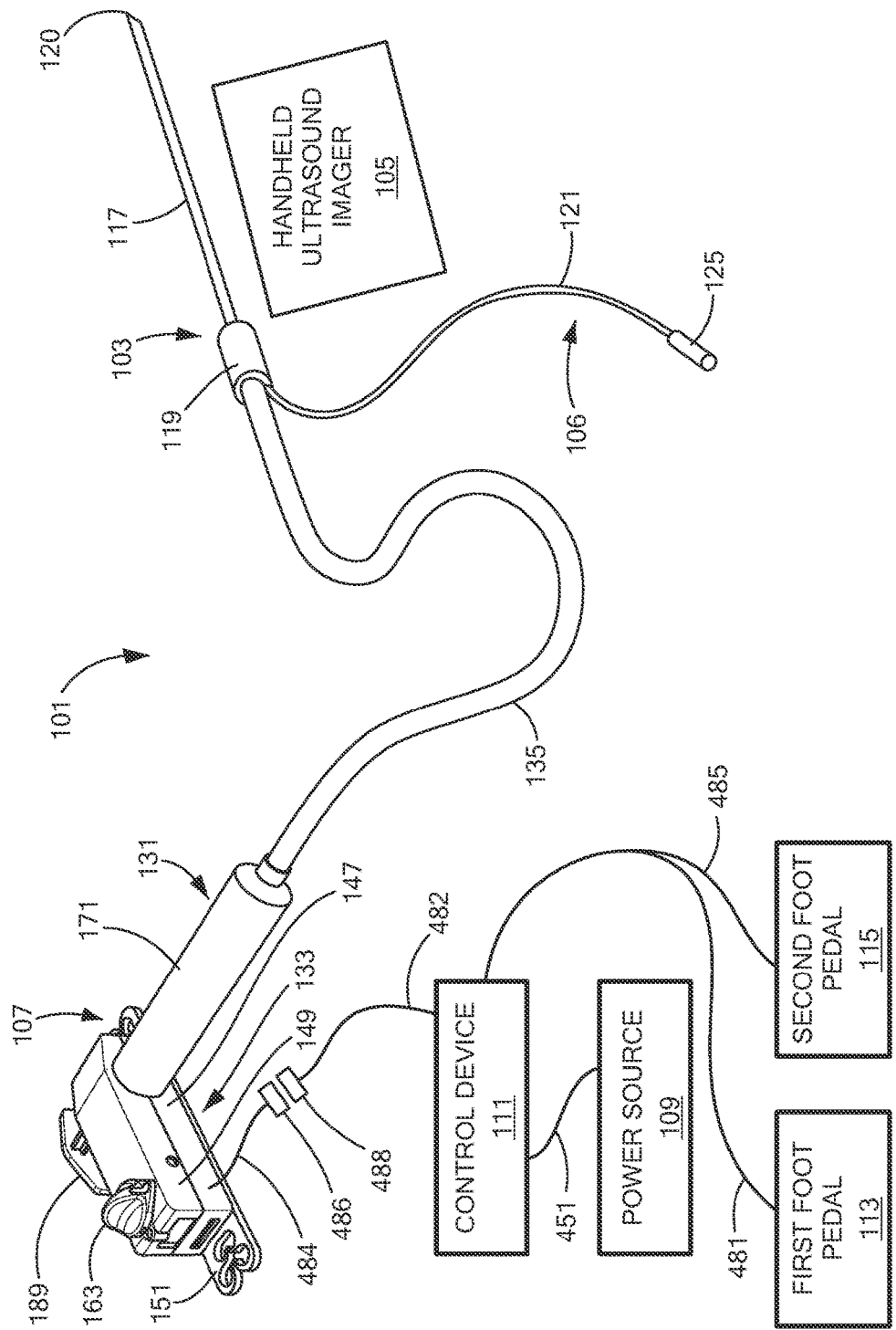
FIG. 2 is a perspective view, partly schematic, of a second embodiment of a system according to the present invention for controllably administering fluid to a patient and/or for controllably withdrawing fluid from the patient.

Referring now to FIG. 2, there is shown a perspective view, partly schematic, of a second embodiment of a system according to the present invention for controllably administering fluid to a patient and/or for controllably withdrawing fluid from the patient, the system being represented generally by reference numeral 101.

System 101 may include one or more of an infusion needle assembly 103, a handheld ultrasound imager 105, a nerve stimulator lead 106, a syringe/pump assembly 107, a power source 109, a control device 111, a first foot pedal 113, and a second foot pedal 115. Each of the foregoing components will now be discussed further below.

Infusion needle assembly 103, which may be similar to infusion needle assembly 13, may be conventional and may include an infusion needle 117 and a needle hub 119. Infusion needle 117 may be a generally tubular member having a sharpened distal end 120 and may have a length of, for example, approximately 25 mm to approximately 150 mm and an outer diameter of, for example, approximately 25 gauge to approximately 18 gauge, Needle hub 119 may be a generally tubular or otherwise finger graspable member coaxially positioned around and fixed to infusion needle 117.

Handheld ultrasound imager 105 may be similar to handhold ultrasound imager 15 of system 11 and may be used in a similar fashion.

Nerve stimulator lead 106 may comprise a wire 121 or other electrically conductive member having a first end inserted into needle hub 119 and in contact with infusion needle 117 and a second end coupled to an electrically conductive connector 125. At least a portion of the length of wire 121 between its first and second ends may be coaxially covered with an electrically insulating jacket (not shown). Connector 125 may be coupled to a source of electrical current, and nerve stimulator lead 106 may be used in the fashion described above to cause a body portion contacted by infusion needle 117 to involuntarily twitch, thereby providing a visual indicator to the physician of the location of infusion needle 117.

If desired, one or both of handheld ultrasound imager 105 and nerve stimulator lead 106 may be omitted from system 101.

Figure 3A:
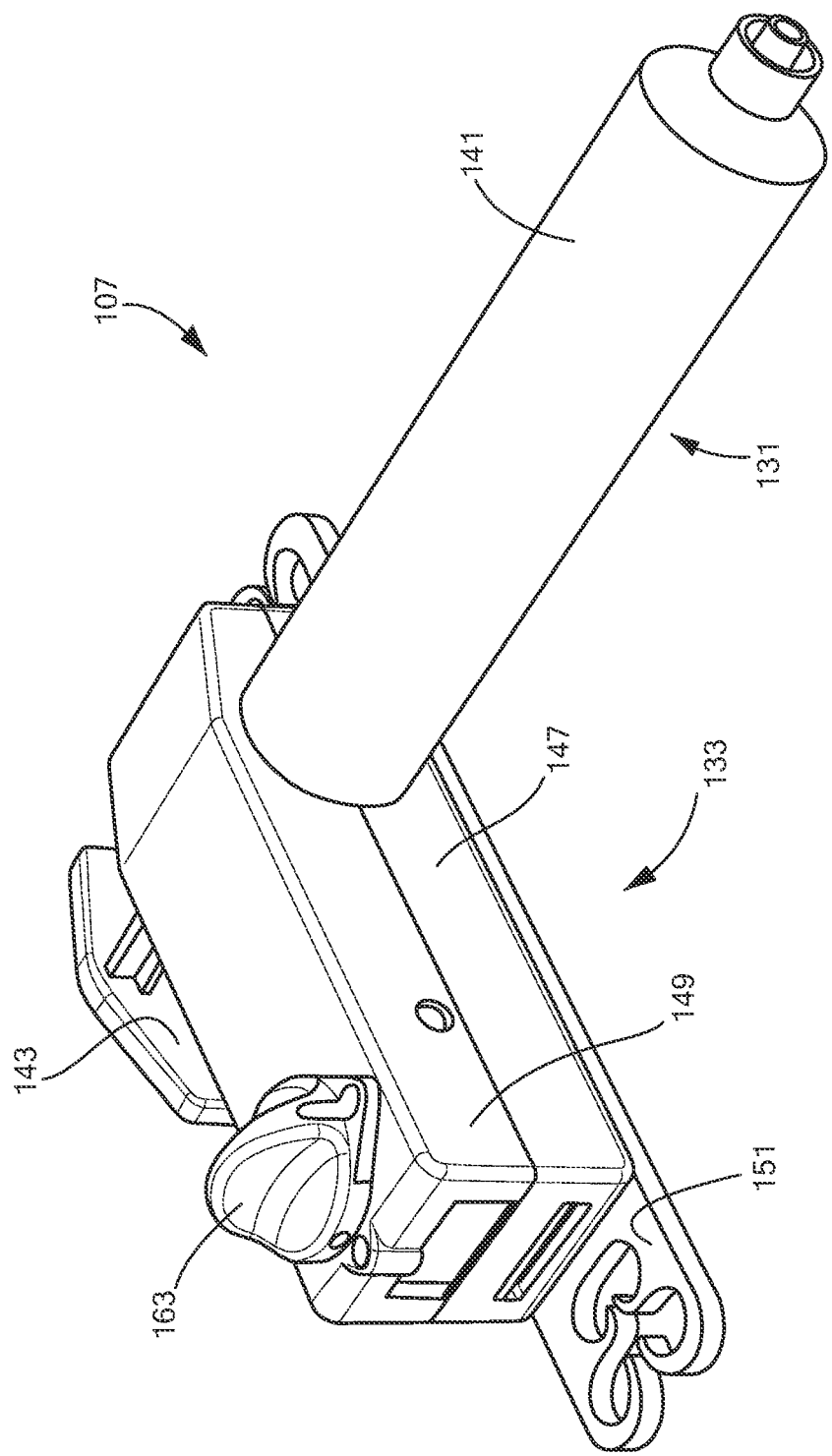
FIGS. 3(a) and 3(b) are perspective and partly exploded perspective views, respectively, of the syringe/pump assembly of FIG. 2.
Figure 3B:
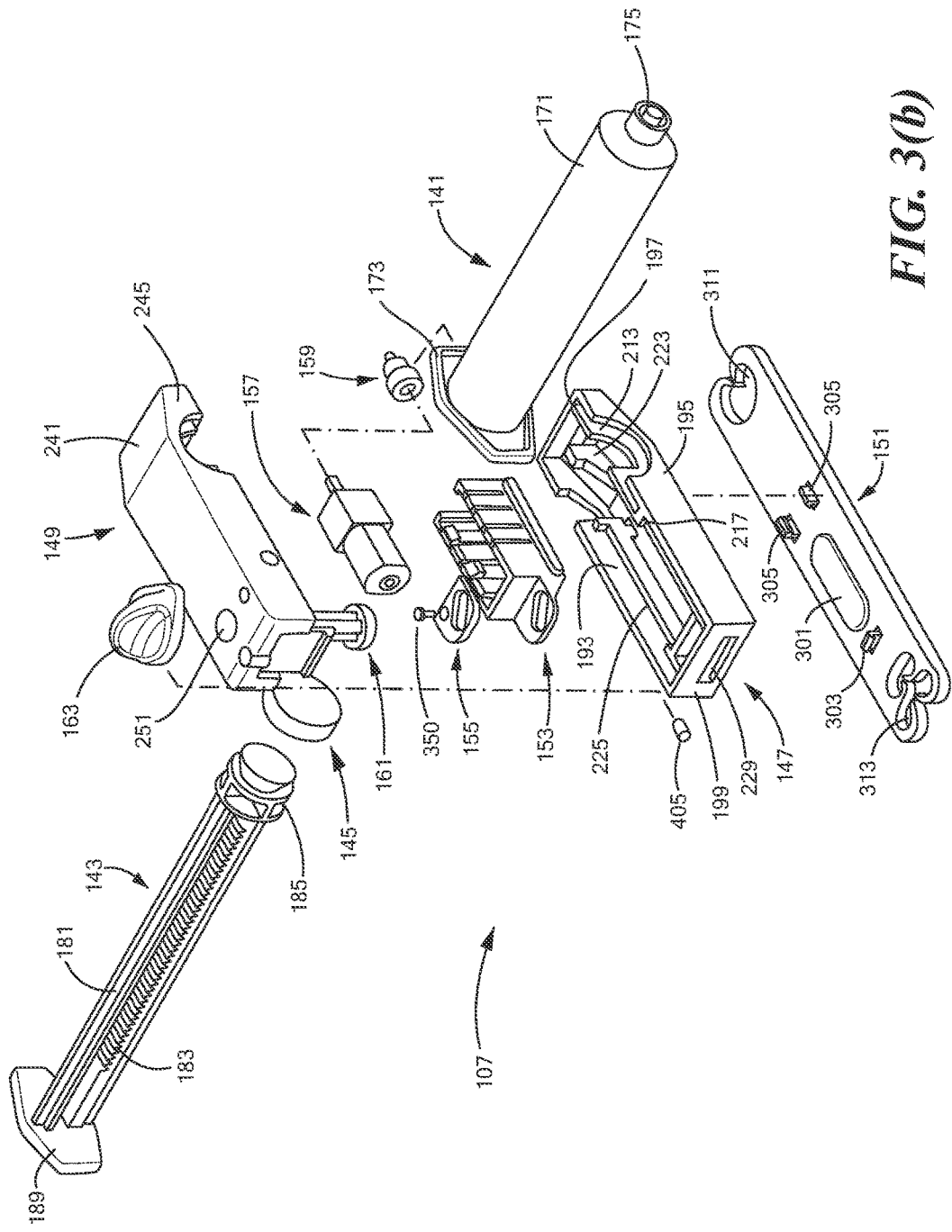
Figure 4:
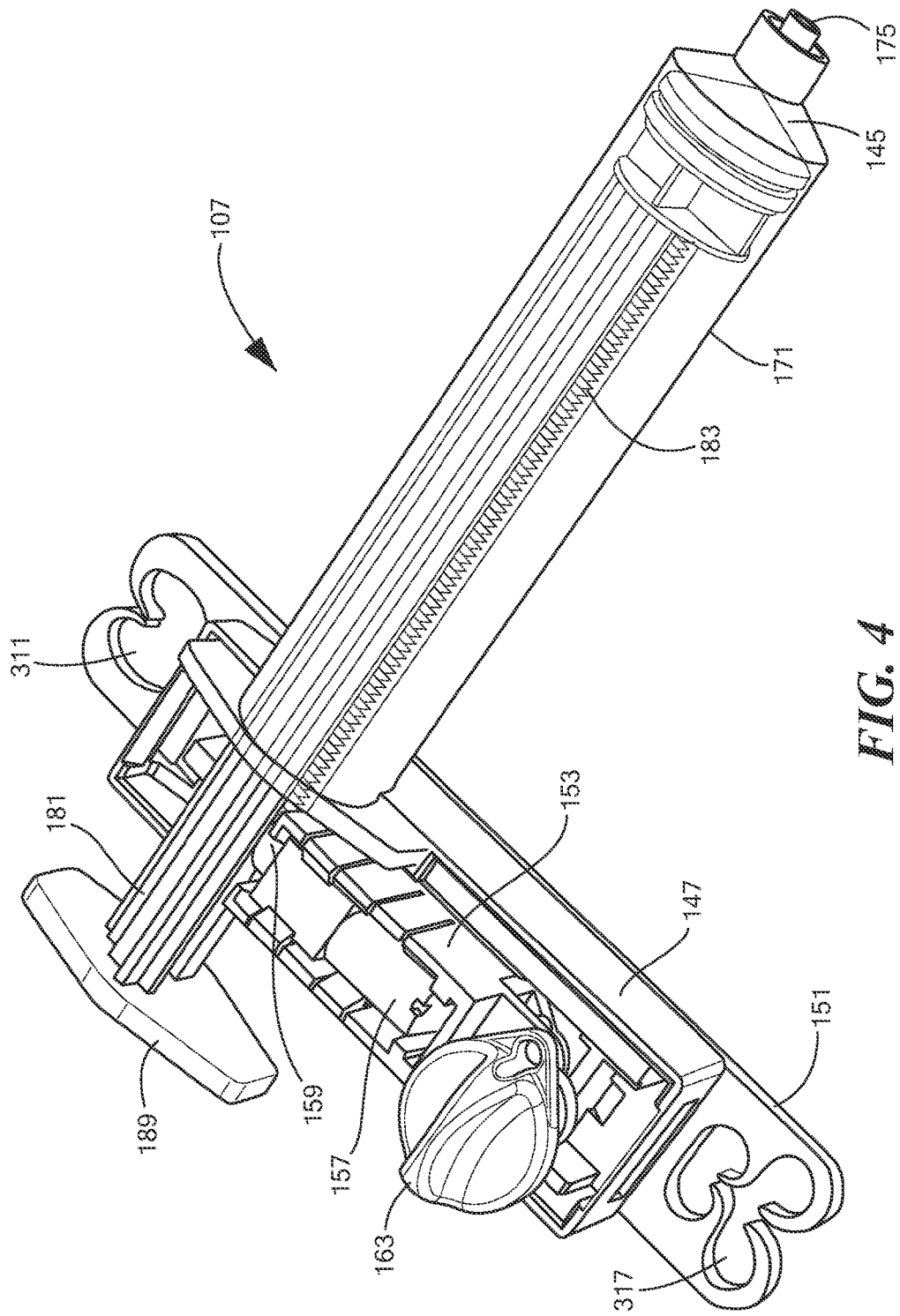
FIG. 4 is a perspective view of the syringe/pump assembly of FIG. 2, with the housing cover not being shown to reveal certain internal components.

Syringe/pump assembly 107 may comprise a syringe 131 and a pump 133. Syringe 131 may be used to hold a quantity of a fluid, such as a medication (e.g., anesthesia) to be administered to a patient or to hold a quantity of a fluid that has been aspirated from the patient. Syringe 131 may be fluidly coupled to infusion needle assembly 103 by a length of tubing 135. Pump 133 may be used to expel fluid from syringe 131 or to draw fluid into syringe 131 by controlling the operation of syringe 131. Referring now to FIGS. 3(*a*), 3(*b*), and 4, syringe/pump assembly 107 is shown in greater detail.

Syringe/pump assembly 107 may include one or more of a syringe body 141, a syringe plunger 143, a seal 145, a housing body 147, a housing cover 149, a clip 151, a motor carrier 153, a friction plate 155, a motor 157, a gear 159, a rotary actuator 161, and a knob 163. Each of the foregoing components will now be discussed further below.

Figure 5A:
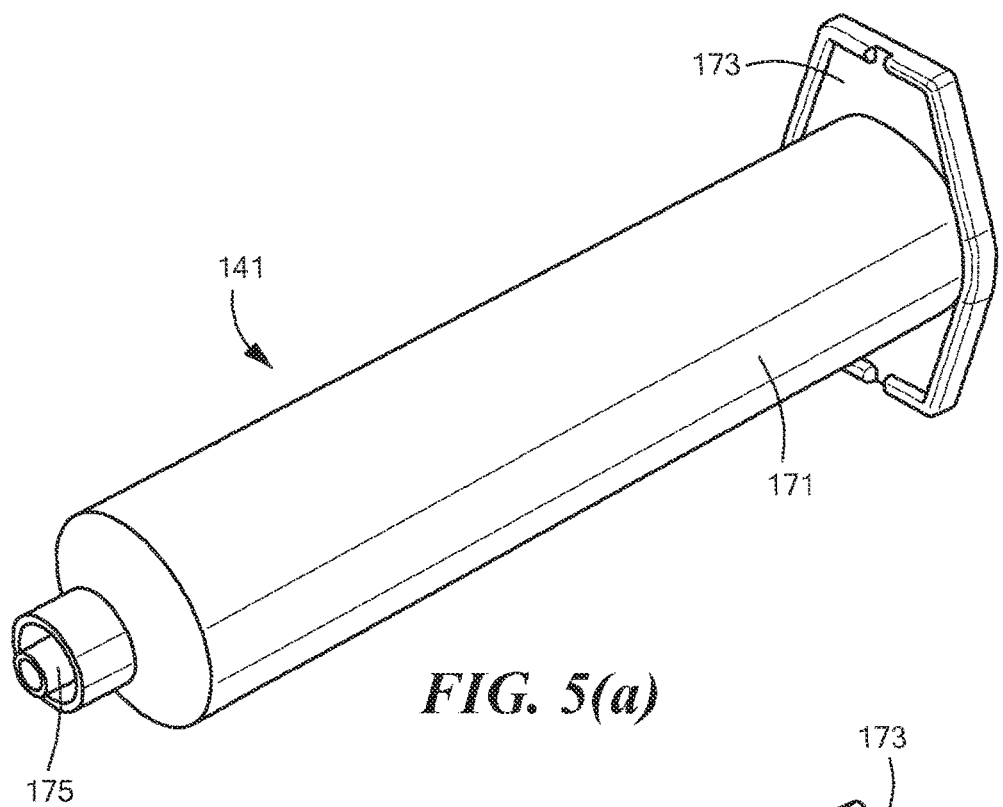
FIGS. 5(a) and 5(b) are enlarged distal perspective and enlarged proximal perspective views, respectively, of the syringe body shown in FIG. 3(b)
Figure 5B:
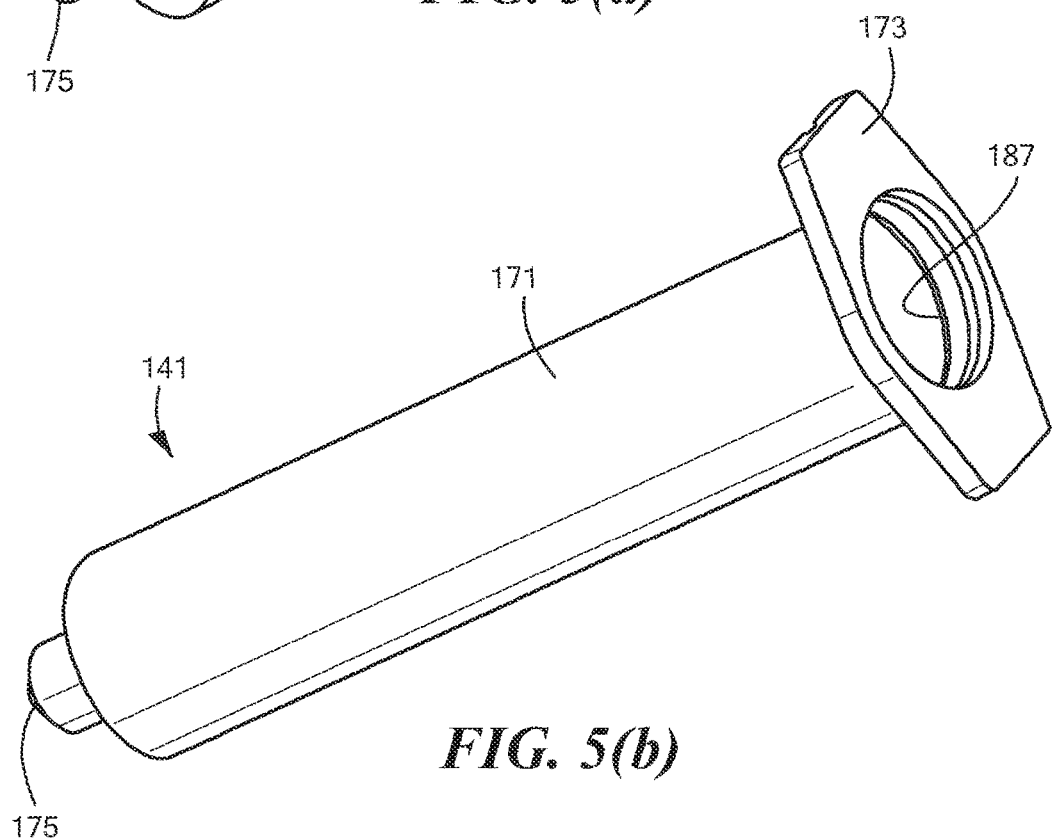

Syringe body 141, which is also shown separately in FIGS. 5(*a*) and 5(*b*), may be conventional and may comprise a unitary tubular member shaped to define a generally cylindrical main portion 171 having a flange 173 disposed at a proximal end thereof and having a male luer connector 175 disposed at a distal end thereof. Flange 173 may be of the type that is appropriately sized and shaped to permit the forefinger and the middle finger of an operator to be rested thereon in the conventional fashion. Male luer connector 175 may be appropriately constructed to mate with a female luer connector (not shown) on the proximal end of a tubing 135 fluidly interconnecting syringe body 141 and infusion needle assembly 103 (see FIG. 2). Although not shown, markings may be provided on main portion 171 to indicate the volume of fluid present within syringe body 141. In the embodiment shown, syringe body 141 may be dimensioned to hold approximately 20 ml of fluid; however, syringe body 141 need not be so dimensioned and may be dimensioned to hold greater than 20 ml of fluid (e.g., up to 60 ml or more) or less than 20 ml of fluid (e.g., down to 10 ml or less). Syringe body 141 may be molded or otherwise fashioned from a rigid, transparent, medical-grade polymer or similar material.

Syringe plunger 143, which is also shown separately in FIGS. 6(*a*) and 6(*b*), may comprise an elongated unitary member, which may be molded or otherwise fashioned from a rigid, medical-grade polymer or similar material. Syringe plunger 143 may be shaped to include a column portion 181 that is generally semi-annular in transverse cross-section. A rack 183, whose purpose will become apparent below, may be formed on an interior surface of column portion 181 along at least a portion of the length of column portion 181. An end member 185 may be provided at the distal end of column portion 181. A distal end 186-1 of end member 185 may be adapted to receive seal 145 thereover. A proximal end 186-2 of end member 185 may be adapted to engage a circumferential rib 187 on the interior of syringe body 141 (see FIG. 5(*b*)) to delimit proximal movement of syringe plunger 143 relative to syringe body 141. A handle 189 may be provided at the proximal end of column portion 181.

Figure 7A:
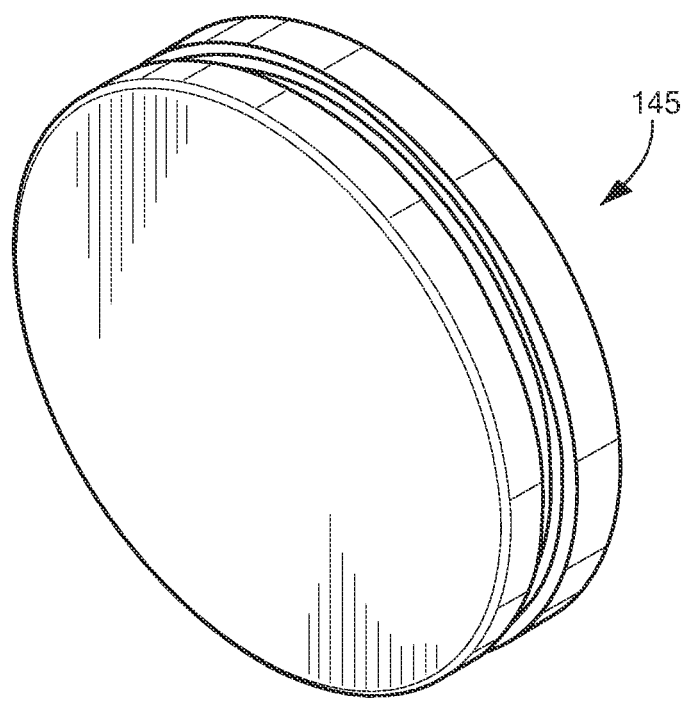
FIGS. 7(a) and 7(b) are enlarged distal perspective and enlarged proximal perspective views, respectively, of the seal shown in FIG. 3(b)
Figure 7B:
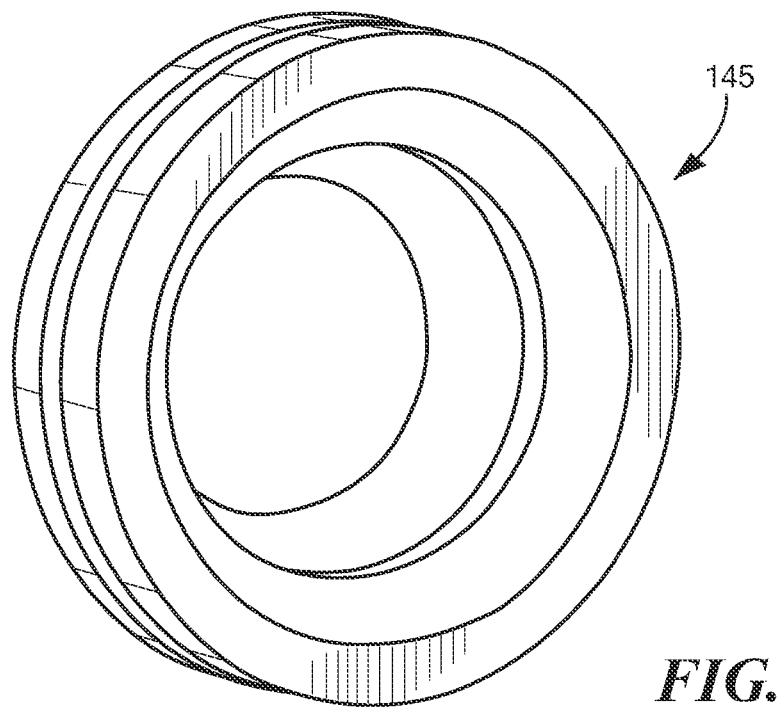

Seal 145, which is also shown separately in FIGS. 7(*a*) and 7(*b*), may be conventional. As noted above, seal 145 may be mounted on the distal end 186-1 of syringe plunger 143 and may be appropriately dimensioned to provide a fluid-tight seal between syringe body 141 and syringe plunger 143.

Figure 8A:
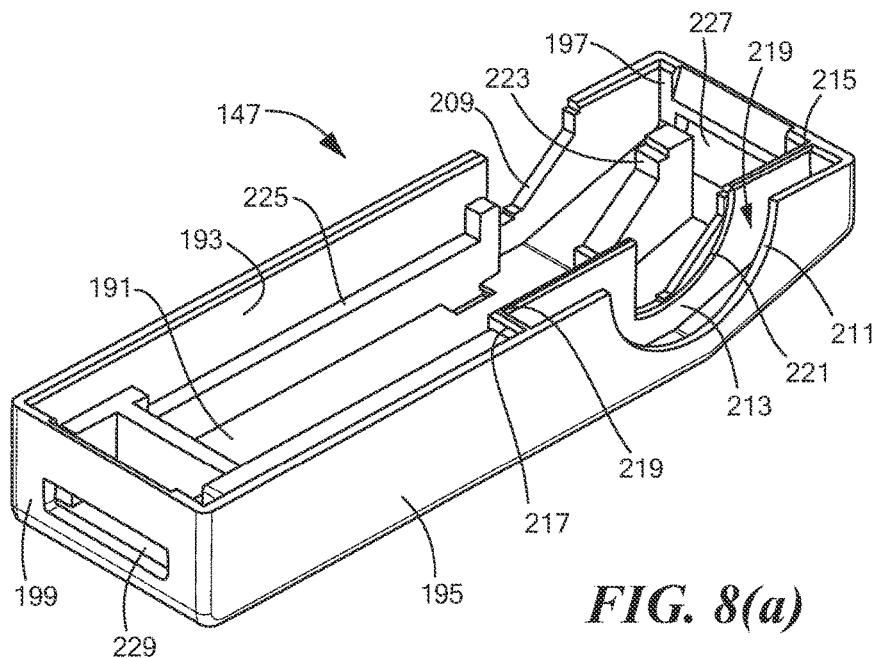
FIGS. 8(a) and 8(b) are enlarged top perspective and enlarged bottom perspective views, respectively, of the housing body shown in FIG. 3(b)
Figure 8B:
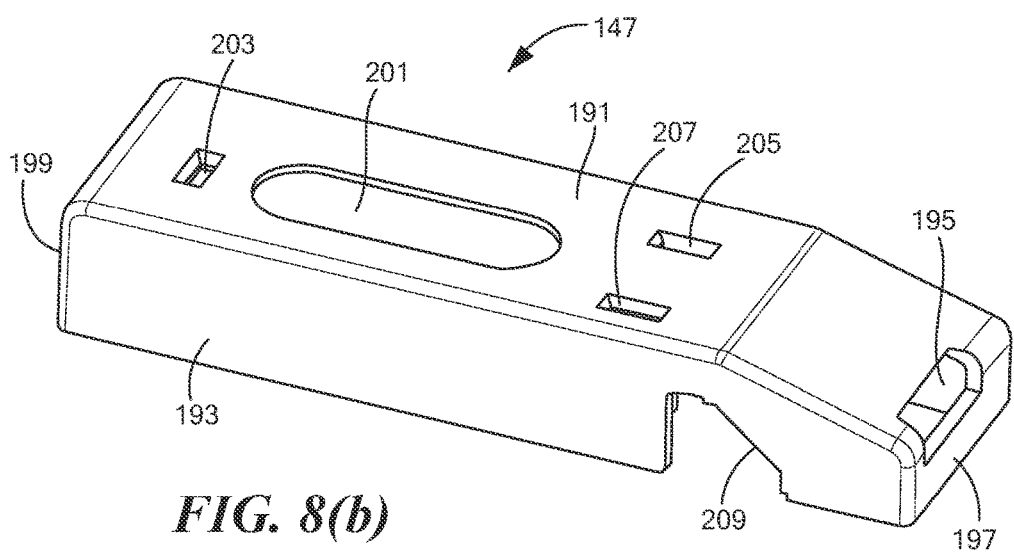

Housing body 147, which is also shown separately in FIGS. 8(*a*) and 8(*b*), may be a unitary structure molded or otherwise fashioned from a suitably storage material, such as a suitable polymer, metal or other material. Housing body 147 may be shaped to include an angled bottom wall 191, a proximal wall 193, a distal wall 195, a left wall 197, a right wall 199, and an open top. Bottom wall 191 may be provided with a plurality of transverse openings 201, 203, 205 and 207, which may be adapted to matingly receive corresponding structures provided on clip 151. Proximal wall 193 may be shaped to include a recess 209, which may be appropriately dimensioned for syringe plunger 143 to be slidably mounted thereacross. Distal wall 195 may also be slurped to include a recess 211, which may be appropriately dimensioned for cylindrical portion 171 of syringe body 141 to extend therethrough. A first internal wall 213, which may be spaced in a parallel fashion a short distance from distal wall 195, may extend upwardly from bottom wall 191 and may be joined at a first end 215 to left wall 197. A second internal wall 217 may join a second end 219 of first internal wall 213 to distal wall 195 such that first internal wall 213, second internal wall 217, left wall 197 and distal wall 195 jointly define a compartment 219. Compartment 219 may be appropriately dimensioned to securely receive flange 173 of syringe body 141. First internal wall 213 may be shaped to include a recess 221, which may be appropriately dimensioned for syringe plunger 143 to be slidably mounted thereacross. A rib 223 may extend upwardly from bottom wall 191 proximate to left wall 197 and may be appropriately sized and shaped to provide support to syringe plunger 143, which may slide thereacross. A pair of rails 225, on which motor earner 153 may be slidably mounted, may extend upwardly from bottom wall 191 and may extend parallel to proximal wall 193 and distal wall 195. (It may be noted that only one of rails 225 can be seen in the drawings, the other rail 225 being obscured by distal wall 195.) A transverse opening 227 may be provided at the intersection of bottom wall 191 and left wall 197. A transverse opening 229 may be provided in right wall 199. Openings 227 and 229 may be used to receive complementary resilient tabs formed on housing cover 149 for use in detachably coupling together housing body 147 and housing cover 149. Although not shown, housing body 147 may additionally include one or more openings through which electrical wires connected to power source 109, control device 111, first foot pedal 113, and second foot pedal 115 may be passed.

Figure 9A:
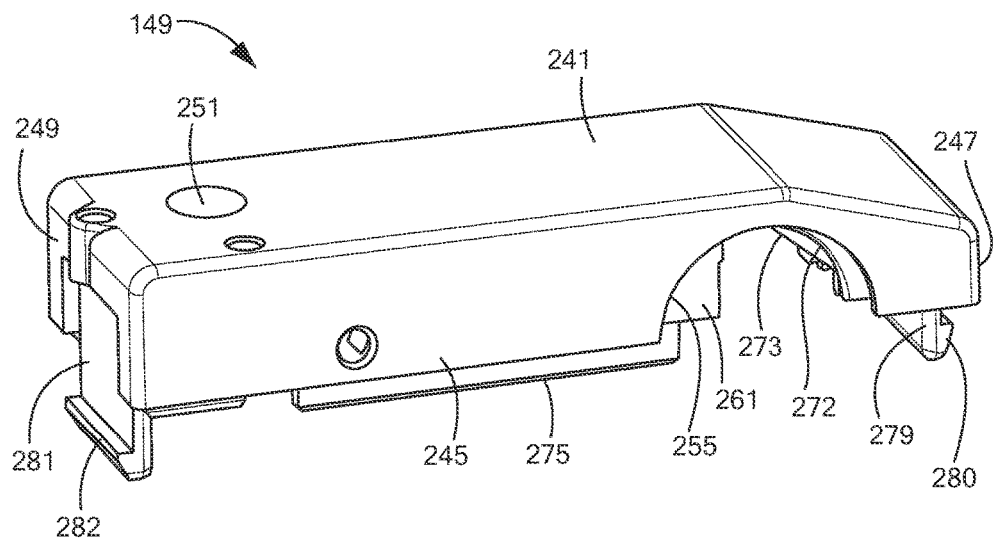
FIGS. 9(a) and 9(b) are enlarged top perspective and enlarged bottom perspective views, respectively, of the housing cover shown in FIG. 3(b)
Figure 9B:
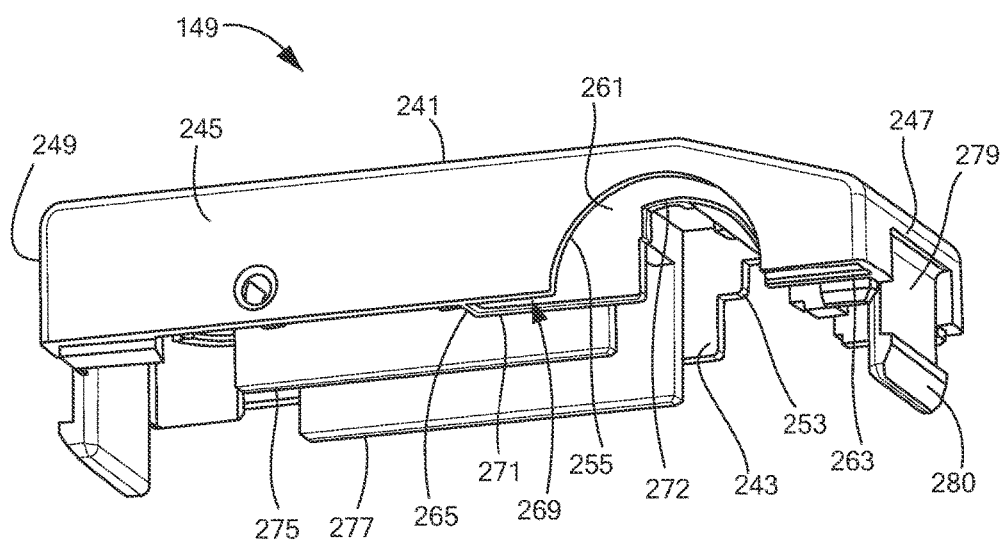

Housing cover 149 which is also shown separately in FIGS. 9(a) and 9(b) may be a unitary structure molded or otherwise fashioned from a suitably strong material, such as a suitable polymer, metal or other material. Housing cover 149 may be shaped to include an angled top wall 241, a proximal wall 243, a distal wall 245, a left wall 247, a right wall 249, and an open bottom. Top wall 241 may be provided with a transverse opening 251, which may be adapted for the rotatable mounting of rotary actuator 161 therewithin. Proximal wall 243 may be shaped to include a recess 253, which, like recess 209 of housing body 147, may be appropriately dimensioned for syringe plunger 143 to be slidably mounted thereacross. Distal wall 245 may be shaped to include a recess 255, which, like recess 211 of housing body 147, may be appropriately dimensioned tor cylindrical portion 171 of syringe body 141 to extend therethrough. A first internal wall 291, which may be spaced in a parallel fashion a short distance from distal wall 245, may extend downwardly from top wall 241 and may be joined at a first end 263 to left wall 247. A second internal wall 265 may join a second end 271 of first internal wall 261 to distal wall 245 such that first internal wall 261, second internal wall 265, left wall 247 and distal wall 245 jointly define a compartment 269. Compartment 269, like compartment 219 of housing body 147, may be appropriately dimensioned to securely receive flange 173 of syringe body 141. First internal wall 261 may be shaped to include a recess 272, which may be appropriately dimensioned for syringe plunger 143 to be slidably mounted thereacross. A rib 273 may extend downwardly from top wall 241 proximate to left wall 247 and may be appropriately sized and shaped to provide support to syringe plunger 143, which may slide thereacross. A pair of rails 225 and 277, against which motor carrier 153 may slide, may extend downwardly from top wall 241 and may extend parallel to proximal wall 243 and distal wall 245. Left wall 247 may be shaped to include a resilient tab 279 having a free end 280 that may be matingly inserted into opening 227, and right wall 249 may be shaped to include a resilient tab 281 having a free end 282 that may be matingly inserted into opening 229.

Figure 10:
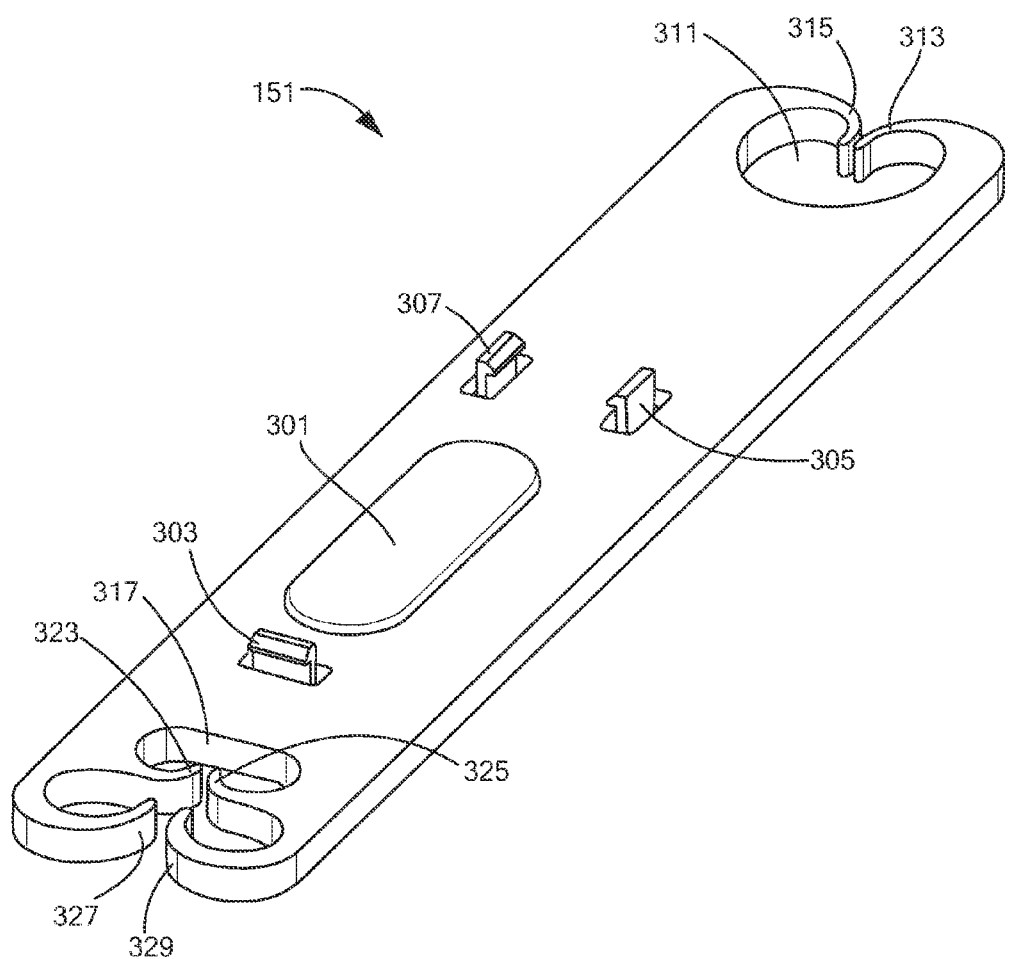
FIG. 10 is an enlarged top perspective view of the clip shown in FIG. 3(b)

Clip 151, which is also shown separately in FIG. 10, may be a unitary structure molded or otherwise fashioned from a suitably strong material, such as a suitable polymer, metal or other material. Clip 151 may be shaped to include a block 301, which may be adapted to mate with opening 201 of housing body 147. Clip 151 may be additionally shaped to include resilient tabs 303, 305, and 307, which may be adapted to be matingly received in openings 203, 205, and 207, respectively, of housing body 147 so that clip 151 may be securely coupled to housing body 147. Clip 151 may be further shaped to include a first transverse opening 311, which may be defined, in part, by a pair of resilient fingers 313 and 315, and a second transverse opening 317, which may be defined, in part, by resilient fingers 323, 325, 327 and 329. A surgical drape worn by patient P, a bed linen for a bed on which patient P may be positioned, or a similar item may be inserted through transverse opening 311 and frictionally engaged, i.e., gripped, by one or both of fingers 313 and 315 and/or may be inserted through transverse opening 317 and frictionally engaged by one or more of resilient fingers 323, 325, 327, and 329. In this manner, syringe/pump assembly 107 may be immobilized during whatever medical procedure is to be performed.

Although housing body 147 and clip 151 are shown in the present embodiment as being two separate pieces, it can readily be appreciated that body 147 and clip 151 may be formed as a single piece.

Figure 11A:
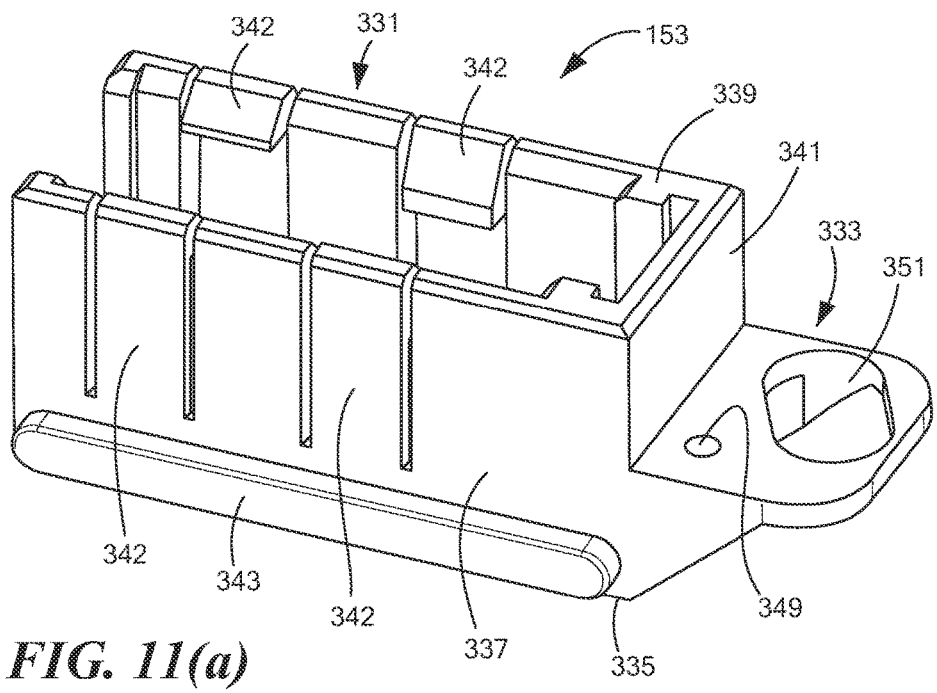
FIGS. 11(a) and 11(b) are enlarged lop perspective and enlarged bottom perspective views, respectively, of the motor carrier shown in FIG. 3(b)
Figure 11B:
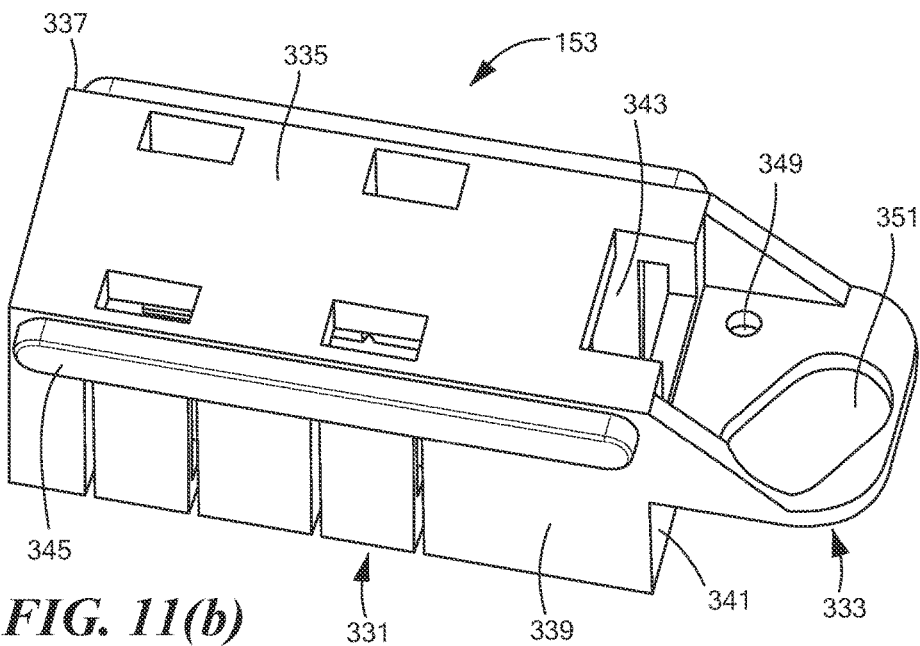

Molar carrier 153, which is also shown separately in FIGS. 11(a) and 11(b), may be a unitary structure molded or otherwise fashioned from a suitably strong material, such as a suitable polymer, metal, such as brass, or other material. Motor carrier 153 may be shaped to include a trough portion 331 and a tab portion 333. Trough portion 331, which may be adapted to securely receive motor 157, may be shaped to include a bottom wall 335, a proximal wall 337, a distal wall 339, a right side wall 341, an open left side, and an open top. An opening 343 may be provided in bottom wall 335 so that wires connected to power source 109, control device 111, first foot pedal 113, and second foot pedal 115 may be passed therethrough. Proximal wall 337 and distal wall 339 may be shaped to include resilient members 342, which may function to securely retain motor 157 within trough portion 331. Ribs 343 and 345 may be provided along proximal wall 337 and distal wall 339, respectively. Ribs 343 and 345 may be appropriately dimensioned to ride on top of rails 225 of housing body 147 and beneath rails 275 and 277 of housing cover 149 so that motor carrier 153 may be moved translationally between the left and right side walls of housing body 147 and housing cover 149. Tab portion 333 may be shaped to include an opening 349 and a slot 351. Opening 349 may be used to receive a screw 350, which may be used to secure friction plate 155 to tab portion 333. Slot 351, which may be generally oval in shape, may be oriented at an angle (e.g., approximately 45 degrees) relative to the longitudinal axis of motor carrier 153. Slot 351 may be used to receive rotary actuator 161, as will be discussed further below, so that rotation of rotary actuator 161 may cause motor carrier 153 to move translationally within housing body 147 and housing cover 149.

Figure 12A:
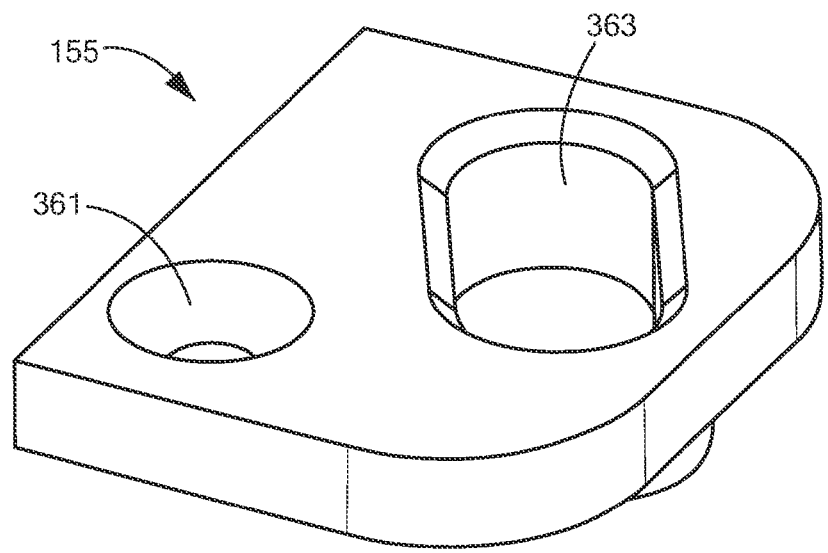
FIGS. 12(a) and 12(b) are enlarged top perspective and enlarged bottom perspective views, respectively, of the friction plate shown in FIG. 3(b)
Figure 12B:
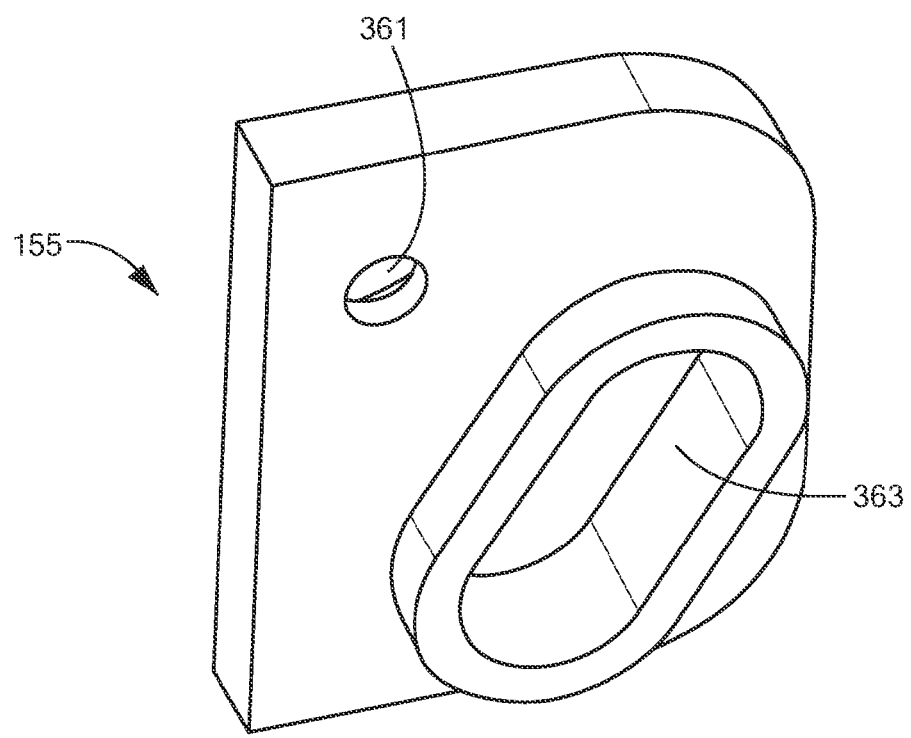

Friction plate 155, which is also shown separately in FIGS. 12(a) and 12(b), may be a unitary structure molded or otherwise fashioned from a suitably strong material, such as a suitable polymer, metal or other material. Friction plate 155 may be appropriately dimensioned to sit on top of tab portion 333 of motor carrier 153. Friction plate 155 may be shaped to include an opening 361 that may be aligned with opening 349 of motor carrier 153 so that screw 350 may be inserted through both opening 361 and opening 349 in order to couple friction plate 155 to motor carrier 153. Friction plate 155 may also be shaped to include a slotted projection 363, which may be tightly received within slot 351 of motor carrier 153.

It should be understood that friction plate 155 may be eliminated if adequate friction can be maintained between rotary actuator 161 and motor carrier 153.

Figure 13:
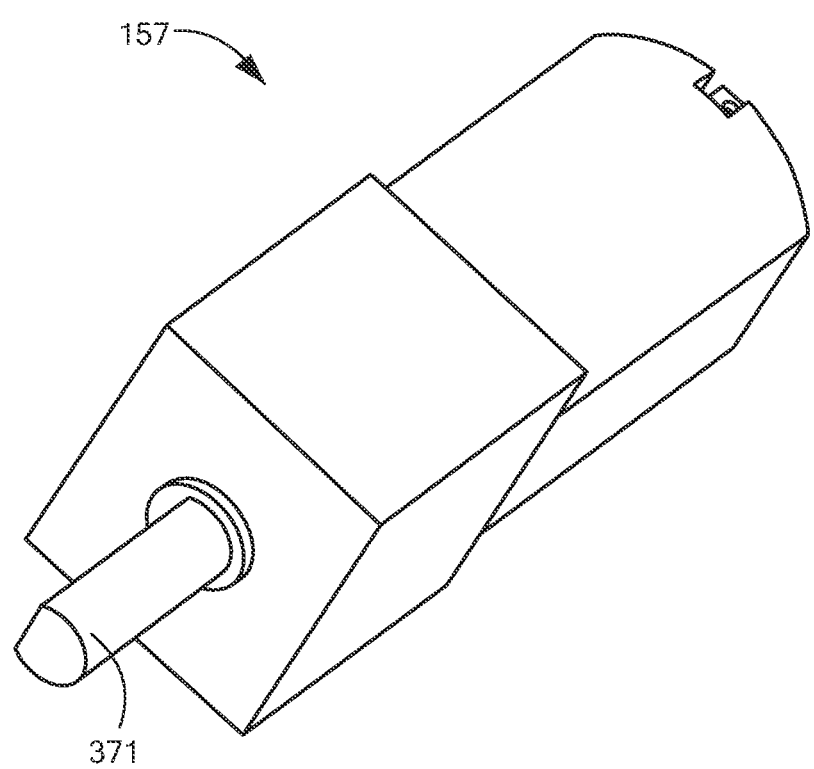
FIG. 13 is an enlarged perspective view of the motor shown in FIG. 3(b)

Motor 157, which is also shown separately in FIG. 13, may be a conventional bi-directional DC motor. Motor 157 may comprise a rotatable shaft 371. Motor 157 may be appropriately dimensioned to be securely received in trough portion 331 of motor carrier 153, with shaft 371 extending through the open left side of motor carrier 153.

Figure 14A:
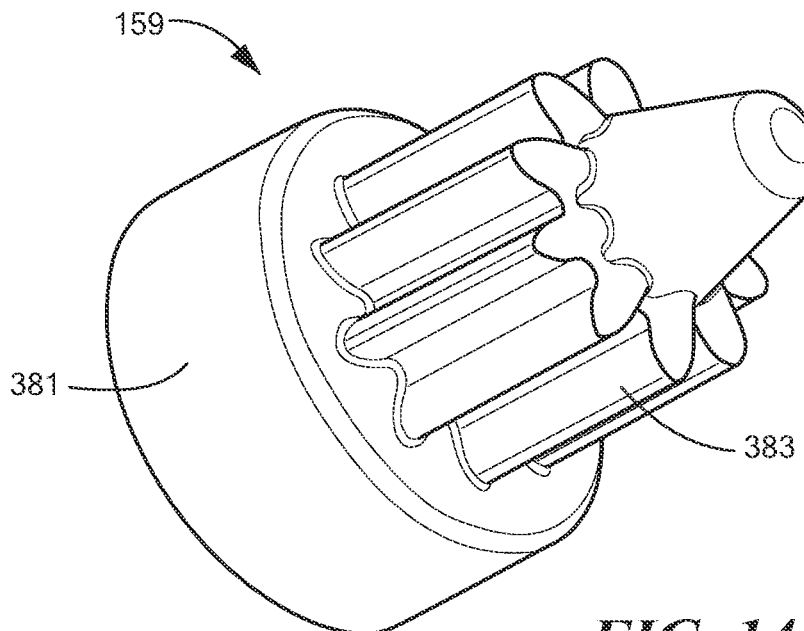
FIGS. 14(a) and 14(b) are enlarged front perspective and enlarged rear perspective views, respectively, of the gear shown in FIG. 3(b)
Figure 14B:
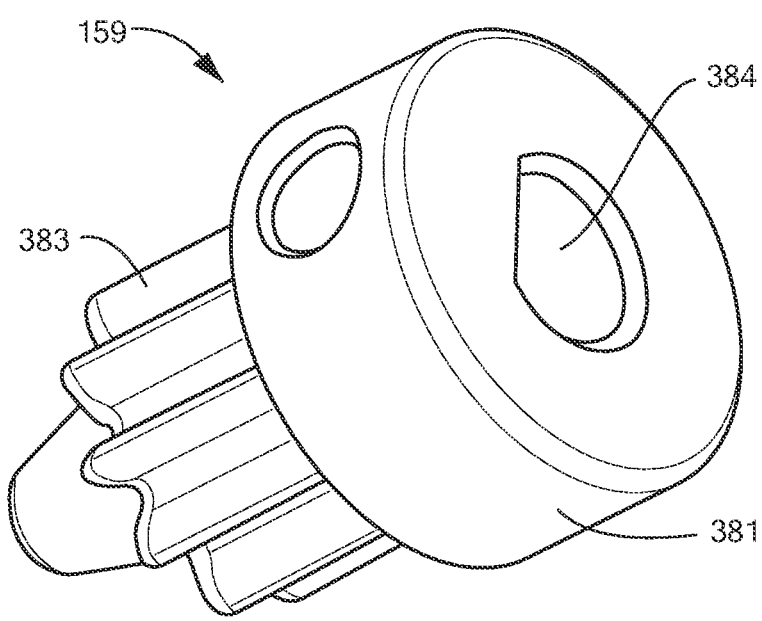

Gear 159, which is also shown separately in FIGS. 14(a) and 14(b), may be a unitary structure molded or otherwise fashioned from a suitably strong material, such as a suitable polymer, metal or other material. Gear 159 may be appropriately shaped to include a base portion 381 and a toothed wheel 383. Base portion 381 may include a longitudinally extending bore 384, which may be appropriately dimensioned to securely and coaxially receive rotatable shaft 371 so that gear 159 may be coupled to rotatable shaft 371 for rotation. Toothed wheel 383 may be appropriately dimensioned so that, when gear 159 is brought into engagement with rack 183 of syringe plunger 143, the rotation of gear 159 causes syringe plunger 143 to be moved translationally relative to syringe body 141, resulting either in the expulsion of fluid from syringe body 141 or in the suctioning of fluid into syringe body 141, depending on the direction in which syringe plunger 143 is moved.

Figure 15A:
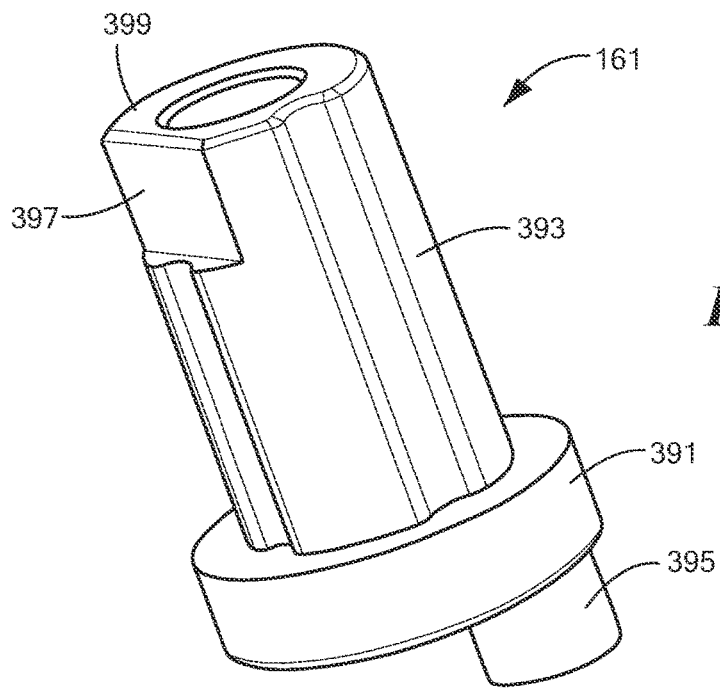
FIGS. 15(a) and 15(b) are enlarged top perspective and enlarged bottom perspective views, respectively, of the rotary actuator shown in FIG. 3(b)
Figure 15B:
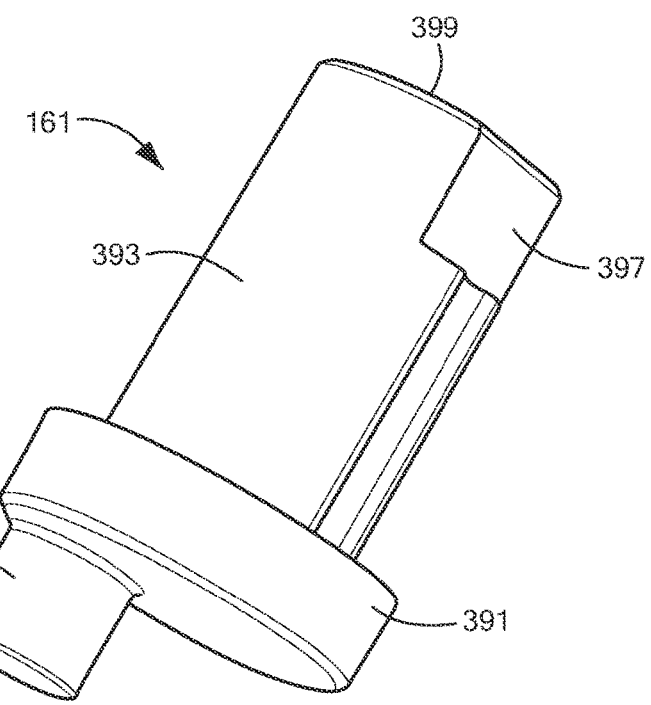

Rotary actuator 161, which is also shown separately in FIGS. 15(a) and 15(b), may be a unitary structure molded or otherwise fashioned from a suitably strong material, such as a suitable polymer, metal or other material. Rotary actuator 161 may be shaped to include a base portion 391, a first post portion 393, and a second post portion 395. Base portion 391 may be generally cylindrical in shape. First post portion 393, which may extend upwardly from base portion 391 and which may be coaxial therewith, may be generally cylindrical in shape and may have a reduced diameter as compared to base portion. First post portion 393 may include a beveled area 397 proximate to its free end 399. Second post portion 395, which may extend downwardly from base portion 391 and which may be off-axis relative to base portion 391 and first post portion 393, may be appropriately dimensioned for engagement with slotted projection 363 of friction plate 155. Consequently, as first post portion 393 is rotated, second post portion 395 causes motor carrier 153 to be moved translationally within housing body 147 and housing cover 149 between a first location, at which gear 159 is engaged with rack 183, and a second location, at which gear 159 is disengaged from rack 183.

Figure 16A:
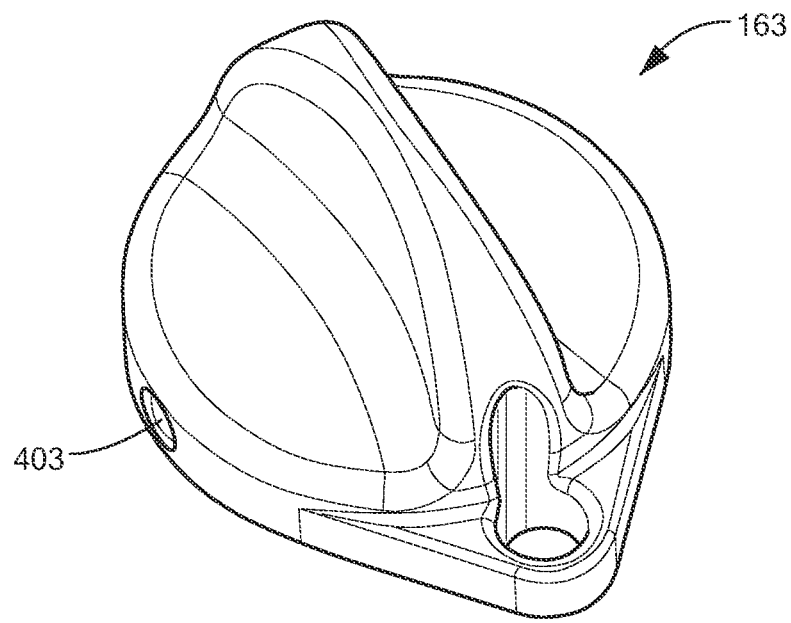
FIGS. 16(a) and 16(b) are enlarged top perspective and enlarged bottom perspective views, respectively, of the knob shown in FIG. 3(b)
Figure 16B:
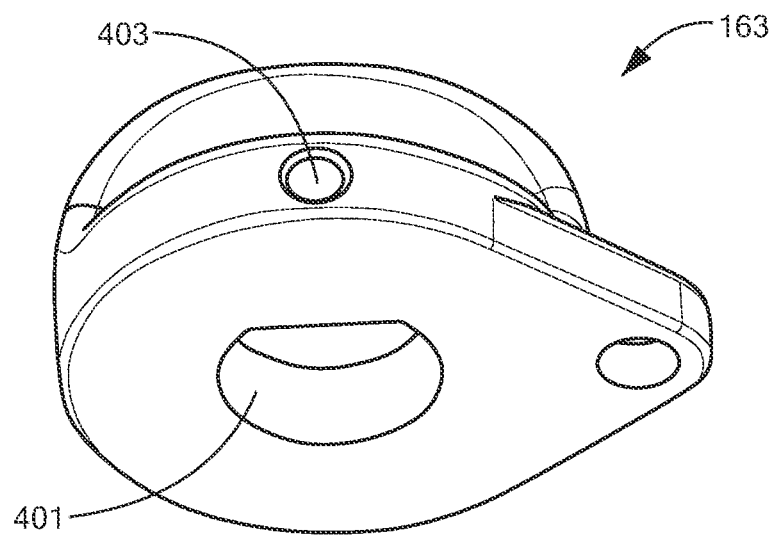

Knob 163, which is also shown separately in FIGS. 16(a) and 16(b), may be a unitary structure molded or otherwise fashioned from a suitably strong material, such as a suitable polymer, metal or other material. Knob 163 may be shaped to include a bore 401, which may be appropriately dimensioned to securely and coaxially receive free end 399 of rotary actuator 161. An opening 403 may be provided in knob 163 to receive a hex socket 405 for securing knob 163 to first post portion 393 of rotary actuator 161.

Referring back now to FIG. 2, power source 109 may be a DC power source, such as one or more batteries, which batteries may be disposable batteries. Although power source 109 is shown in the present embodiment as being external to syringe/pump assembly 107, it should be understood that power source 109 may be incorporated into syringe/pump assembly 107. Alternatively, as discussed further below, power source 109 may be incorporated into foot pedals 113 and 115.

Control device 111 may be any type of mechanism for keeping the pressure in the fluid path from exceeding a predetermined threshold. Where system 101 is being used, for example, to anesthetize a nerve, the threshold value may be approximately 10 psi to approximately 20 psi, preferably approximately 15 psi to approximately 20 psi. Such a pressure control mechanism may operate, for example, by limiting the maximum motor torque by voltage or current control, by using a mechanical or electromagnetic clutch, by electrical current limiting the battery source, by using a pressure relief valve which bleeds fluid as waste to limit the pressure, or by using a pressure sensor to cutoff power to the drive mechanism at a pressure limit. If a maximum torque specification or a current limiting of the battery source is employed, then, if an occlusion occurs in the fluid path that causes the fluid pressure to exceed the threshold, such a maximum torque specification or current limiting of the battery source simply stalls the factor and does not allow it to drive the plunger any further. Alternatively, with a pressure relief valve, the fluid flow is simply diverted from the fluid path, keeping the pressure below the threshold. With a pressure sensor, the effect is to simply cutoff the power source to the motor.

Figure 17:
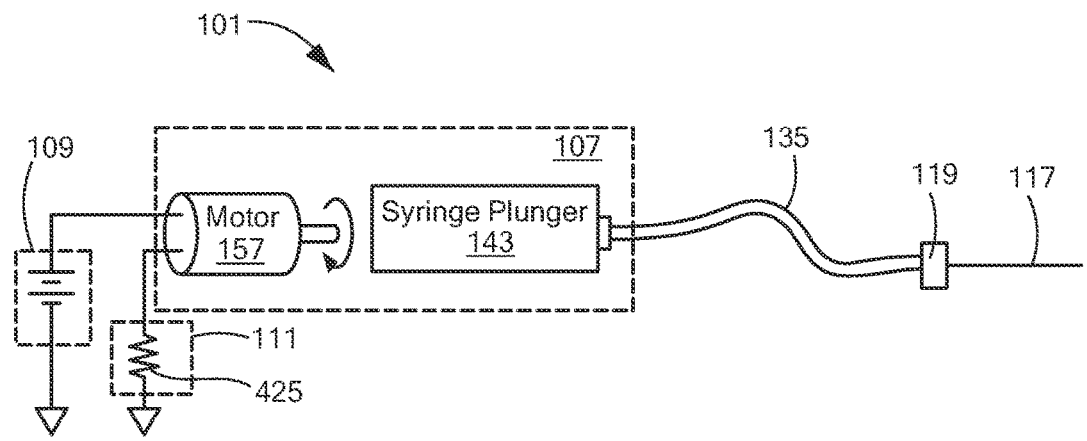
FIG. 17 is a simplified schematic representation of a first exemplary embodiment of the control device of FIG. 2, the first exemplary embodiment of the control device being shown as part of a simplified rendering of the system of FIG. 2.

Referring now to FIG. 17, there is shown a simplified schematic representation of a first exemplary embodiment of control device 111. (For simplicity and ease of understanding, the first exemplary embodiment of control device 111 is shown in FIG. 17 as part of system 101. Certain elements of system 101, such as handheld ultrasound imager 105, nerve stimulator lead 106, first foot pedal 113, and second foot pedal 115, are not shown in FIG. 17.) As shown in FIG. 17, the first exemplary embodiment of control device 111 may be in the form of a maximum torque (pressure) limiter that may comprise a resistor 425. The resistance of resistor 425 may be selected so as to cause motor 157 to stop or to stall when the fluid pressure its the fluid path exceeds a predetermined threshold pressure. Where, for example, system 11 is intended to be used to administer regional anesthesia, such a threshold pressure may be approximately 15 psi. The necessary magnitude of resistance provided by resistor 425 may depend on one or more factors, such as, but not limited to, the type of motor being used and the size of syringe being used.

Figure 18:
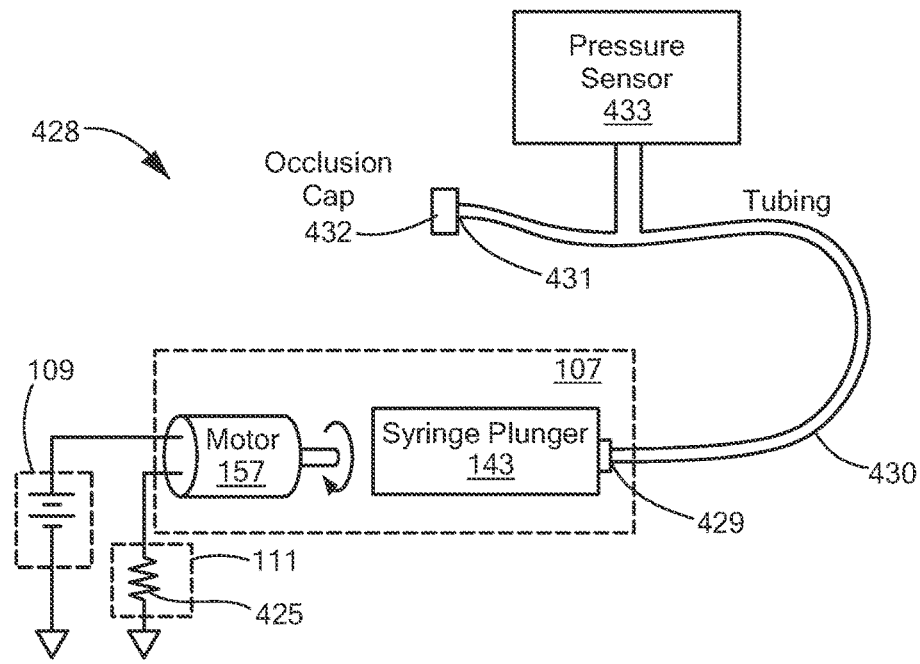
FIG. 18 is a simplified schematic representation of an experimental set-up used to measure the pressure generated by a small electric motor used in a prototype of the syringe/pump assembly of FIG. 2 for driving a 20 mL syringe whose output was occluded.

Referring now to FIG. 18, there is schematically shown an experimental set-up that was used to measure the pressure generated by a small electric motor used in a prototype of syringe/pump assembly 107 for driving a 20 mL syringe whose output was occluded, the experimental set-up being represented generally by reference numeral 428.

Figure 19:
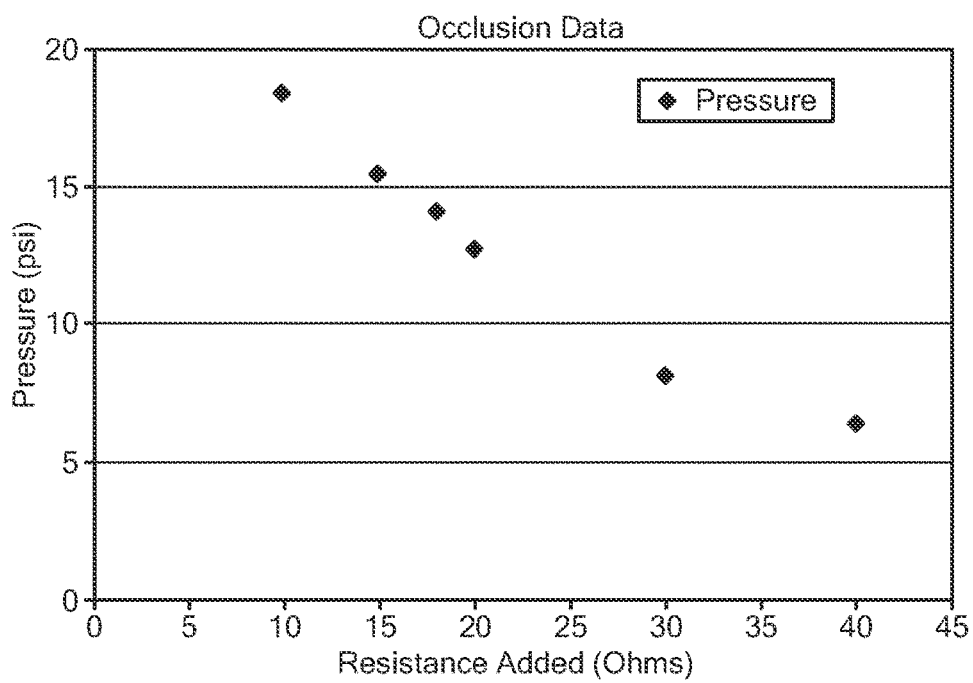
FIG. 19 is a graph depicting the pressure measured as a function of resistance added using the experimental set-up of FIG. 18.
Figure 20:
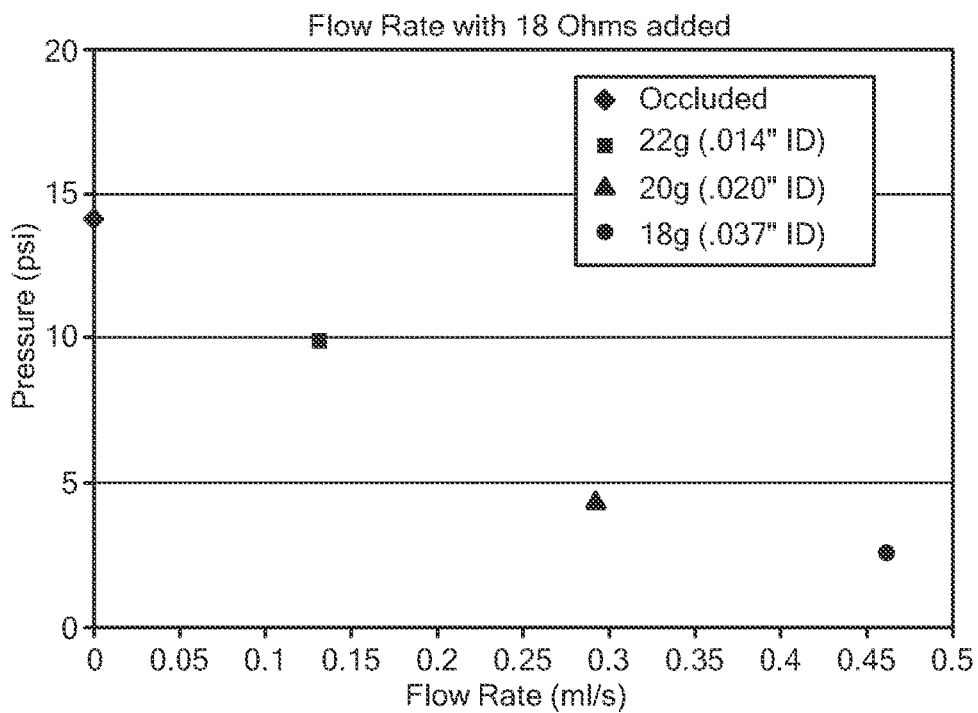
FIG. 20 is a graph depicting the flow rates measured when replacing the occlusion cap in the experimental set-up of FIG. 18 with various needle types and using an 18-ohm resistor as the control device.

Set-up 428 comprises syringe/pump assembly 107. Assembly 107 is electrically connected to each of power source 109 and control device 111. The output of syringe/pump assembly 107 is coupled to an input end 429 of a length of tubing 430. An occlusion cap 423 is mounted on an output end 431 of tubing 430, and a pressure sensor 433 is positioned at an intermediate point within tubing 430. As can be seen in FIG. 19, as the resistance increased from about 10 ohm to about 40 ohm, the maximum pressure decreased from about 18 psi to about 7 psi. In particular, an 18-ohm resistor in series with moon 157 limited the torque and resulted in a maximum pressure of just under 15 psi, which is a desirable result. FIG. 20 shows the flow rates for various needle types (i.e., a 22-gauge needle, a 20-gauge needle, an 18-gauge needle, and an occluded needle) using set-up 428 with an 18-ohm resistor for control device 111 (and replacing occlusion cap 432 with the various needles). The resulting flow rates for the non-occluded needles varied from about 0.13 mL/see to about 0.46 mL/sec.

Referring now to FIG. 21, there is shown a simplified schematic representation of a second exemplary embodiment of control device 111. (For simplicity and ease of understanding, the second exemplary embodiment of control device 111 is shown in FIG. 21 as part of system 101. Certain elements of system 101, such as handheld ultrasound imager 105, nerve stimulator lead 106, first foot pedal 113, and second toot pedal 115, are not shown in FIG. 21.) In order to distinguish the second exemplary embodiment of control device 111, which is shown in FIG. 21, from the first exemplary embodiment of control device 111, which shown in FIG. 17, the second exemplary embodiment of control device 111 is represented generally in FIG. 21 by reference numeral 111'. As shown in FIG. 21, control device 111' may be in the form of a maximum torque (pressure) limiter that may comprise a current sensing circuit (or current sensor) 435, a resistor 437, and a shutoff switch 439.

Referring now so FIG. 22, there is shown a simplified schematic representation of a third exemplary embodiment of control device 111. (For simplicity and ease of understanding, the third exemplary embodiment of control device 111 is shown in FIG. 22 as part of system 101. Certain elements of system 101, such as handheld ultrasound imager 105, nerve stimulator lead 106, first foot pedal 113, and second foot pedal 115, are not shown in FIG. 22.) In order to distinguish the third exemplary embodiment of control device 111, which is shown in FIG. 22, from the first exemplary embodiment of control device 111, which shown in FIG. 17, the third exemplary embodiment of control device 111 is represented generally in FIG. 22 by reference numeral 111". As shown in FIG. 22, control device 111" may be in the form of a maximum torque (pressure) limiter that may comprise a fluid path pressure sensor 445 and a shutoff switch 447.

Referring back now to FIG. 2, although control device 111 is shown in the present embodiment as being external to syringe/pump assembly 107, it should be understood that control device 111 may be incorporated into syringe/pump assembly 107. Alternatively, control device 111 may be incorporated into foot pedals 113 and 115. In the present embodiment, control device 111 may be electrically coupled to motor 157 (see FIG. 3b) by wires 482 and 484, which may be coupled to one another by mating connectors 486 and 488. Power source 109 may be coupled to control device 111 by a wire 451.

First foot pedal 113, which may be conventional, may be electrically coupled by a wire 481 to control device 111, and second foot pedal 115, which may be conventional may be electrically coupled by a wire 485 to control device 111. System 101 may be configured so that, when first foot pedal 113 is depressed, motor 157 is operated in injection-mode, and so that, when second foot pedal 115 is depressed, motor 157 is operated in aspiration-mode. Alternatively, system 101 may be configured so that, when first foot pedal 113 is depressed, motor 157 is operated in aspiration-mode, and so that, when second foot pedal 115 is depressed, motor 157 is operated in injection-mode. First foot pedal 113 and second foot pedal 115 may be distinguishable from one another in such a way as to indicate which foot pedal may be used for aspiration and which foot pedal may be used for infusion. For example, the foot pedals may be prominently labeled with the words like "ASPIRATE" and "INFUSE" and/or may be decorated with icons that convey their respective functions. In addition or alternatively, the foot pedals may be colored differently, such as blue or green for infusion and yellow for aspiration.

As can readily be appreciated, although foot pedals 113 and 115 are shown in FIG. 2 being coupled to syringe/pump assembly 107 by wires, such wires may be replaced by any wireless means including, but not limited to, using Bluetooth communications to connect foot pedals 113 and 115 to fluid pump 133 or using voice command and recognition electronics within a control module to control the application of power front power source 109 to motor 157 of fluid pump 133.

If desired, one or more components of system 101 and, in fact, preferably all of the components of system 101, except possibly for handheld ultrasound imager 15, may be disposable, single-use items. This single-use feature may be desirable as it may provide a convenient way of ensuring the sterility of system 101 in an operating room or surgery center environment.

To use system 101 to inject fluid into a patient, syringe/pump assembly 107 may initially be arranged so that toothed wheel 383 of gear 159 is disengaged from rack 183 of syringe plunger 143. Such an arrangement enables the physician to manually fill syringe 131 with the desired fluid. The physician may then prime tubing 135 either manually, before turning rotary actuator 161 to cause toothed wheel 383 to engage rack 183, or by turning rotary actuator 161 to cause toothed wheel 383 to engage rack 183 and then by depressing the appropriate foot pedal to cause toothed wheel 383 to drive syringe plunger 143 in such a way as to cause sufficient fluid to be expelled from syringe 131 to prime. Additional depression of said foot pedal when infusion needle 117 is placed in the patient P causes fluid to be injected into the patient. If, at any time during the procedure, the physician wishes to manually control syringe 131, pump 133 can be disengaged from syringe 131 by turning rotary actuator 161 to disengage toothed wheel 383 from rack 183. If aspiration of fluid front the patient P is desired, this may be accomplished by depressing the other foot pedal, causing toothed wheel 383 to move rack 183 in the opposite direction. If, while gear 383 is engaged with rack 183 and either first foot pedal 113 or second foot pedal 115 is depressed, the pressure in the fluid path exceeds the predetermined threshold, control device 111 causes gear 383 to stop driving the movement of syringe plunger 143.

System 101 may be used to deliver fluid at a desired flow rate, such as up to 1 ml/see, without having the pressure of the fluid in the fluid path exceed a desired threshold, such as about 15 psi. In a preferred embodiment, syringe plunger 143 may be driven at such a speed that approximately 0.5 milliliter of fluid per sec is dispensed front syringe 131. Since physicians use a wide range of needle diameters, for example, from 16 G up to 27 G and a wide range of needle lengths, for example, from 25 millimeters to 150 millimeters, the flow rates of the fluid may range depending on the pump, syringe and needle type selected and may vary, for example, from about 0.01 milliliters/sec to about 0.5 millimeters/sec.

Figure 23:
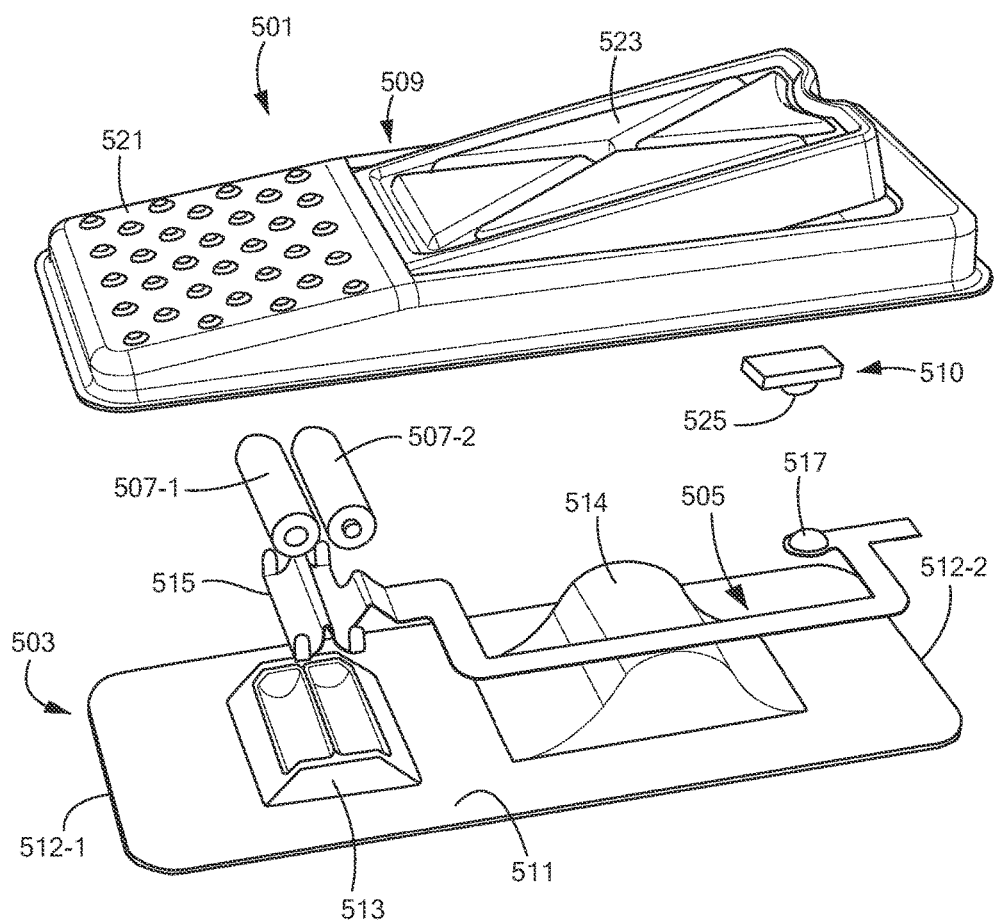
FIG. 23 is a partly exploded perspective view of as alternate foot pedal for use in the system of FIG. 2.

Referring now to FIG. 23, there is shown a partly exploded perspective view of an alternate foot pedal for use in system 101, said alternate foot pedal being constructed according to the present invention and being represented generally by reference numeral 501. Foot pedal 501 may be used in place of first foot pedal 113 or may be used in place of second foot pedal 115; alternatively, a pair of foot pedals 501 may be used in place of foot pedals 113 and 115.

Foot pedal 501 may comprise a bottom 503, a first electrically-conductive element 505, a pair of batteries 507-1 and 507-2, a top 509, and a second electrically-conductive element 510. Each of the foregoing components will now be discussed further below.

Bottom 503 may be a unitary structure molded or otherwise fashioned from a suitable material, which may be an electrically non-conductive material, such as an electrically non-conductive polymer or the like. Bottom 503 may be shaped to include a base portion 511, which may be generally planar, a battery holder 513, which may be seated on top of base portion 511 proximate to a first end 512-1 of base portion 511, and a resilient member 514, which may be biased upwardly and which may be disposed proximate to a second end 512-2 of base portion 511. Instead of making battery holder 513 integral with the remainder of bottom 503, battery holder 513 may be made separately from bottom 503 and then may be mounted on bottom 503 using an adhesive or other suitable mounting means.

First electrically-conductive element 505 may be an elongated unitary structure made of a suitable, electrically-conductive material, such as a metal. First electrically-conductive element 505 may comprise a first end 515. First end 515 may be appropriately shaped to be received within battery holder 513 and may be adapted to make electrical contact with batteries 507-1 and 507-2, which may be seated on first end 515. The remainder of first electrically-conductive element 505 may be mounted on top of base portion 511 of bottom 503 and may be shaped to include a contact 517.

Batteries 507-1 and 507-2, which may be conventional batteries and, more specifically, may be conventional disposable batteries, may be seated on top of first end of first electrically-conductive element 505 within battery holder 513. Although two batteries 507-1 and 507-2 are shown in the present embodiment, there could be as few as one battery or as many as three or more batteries.

Top 509 may be a unitary structure molded or otherwise fashioned from a suitable material, which may be an electrically non-conductive material, such as an electrically non-conductive polymer or the like. Top 509 may be shaped to include a base portion 521 and a tab 523. Tab 523, which may be positioned over and in contact with resilient member 514 of bottom 503, may be adapted for hinged movement relative to base portion 521. In this manner, tab 523 may be pivoted downwardly, against the force of resilient member 514, when an operator applies sufficient downward force to tab 523.

Second electrically-conductive element 510, which may be made of a suitable, electrically-conductive element, such as a metal, may be secured to the bottom of tab 523 at an appropriate location so that, when tab 523 is pivoted downwardly, a contact 525 provided on second electrically-conductive element 510 may make contact with contact 517 of first electrically-conductive element 505. Second electrically-conductive element 510 may be coupled to wire 481 (if foot pedal 501 is used in place of first foot pedal 113) or to wire 485 (if foot pedal 501 is used in place of second foot pedal 115).

As can be appreciated, because foot pedal 501 includes a power source, the need for power source 109 is obviated when foot pedals 113 and 115 are replaced with a pair of foot pedals 501.

Foot pedal 591 may be a disposable, single-use item.

Figure 24:
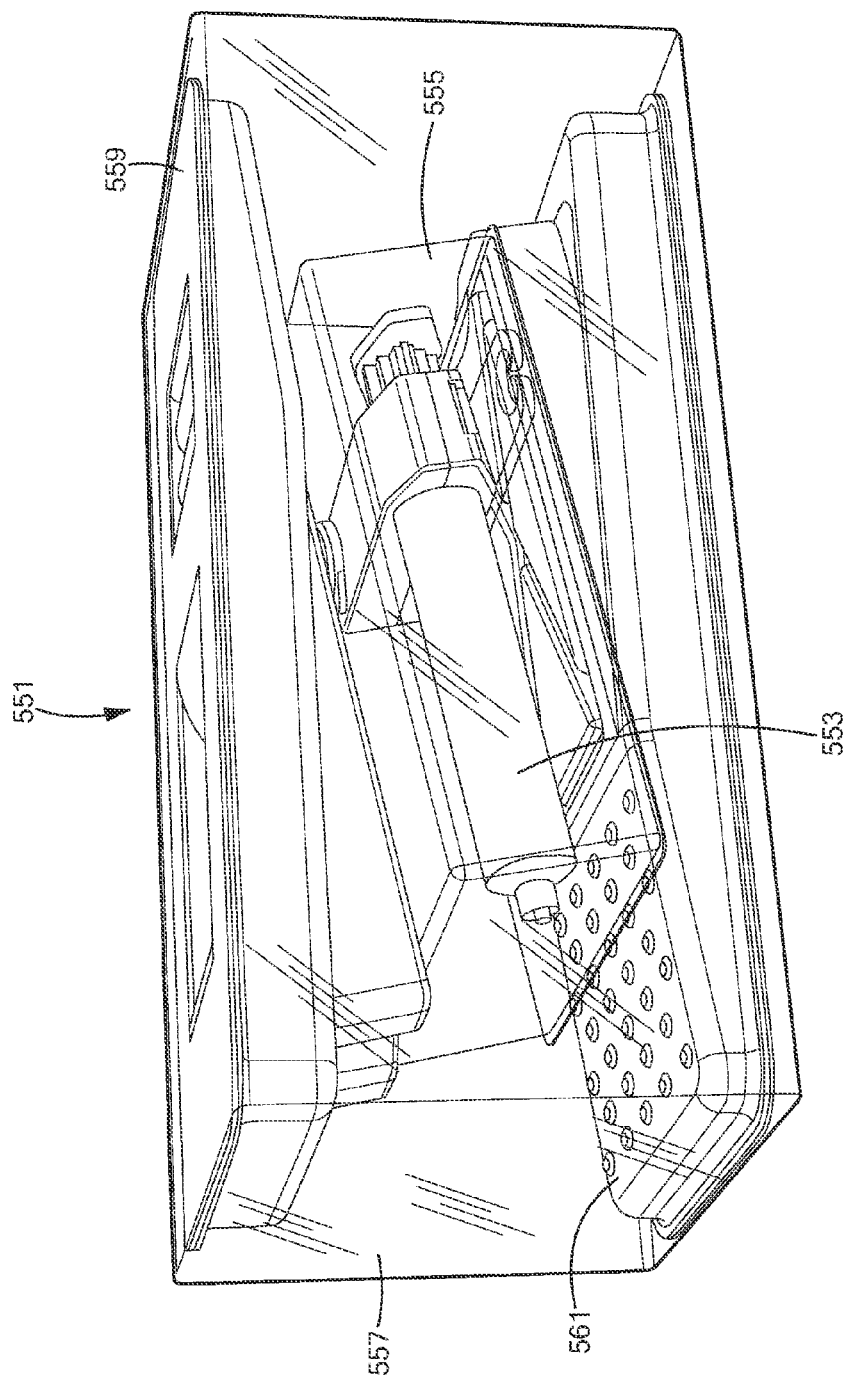
FIG. 24 is a perspective view of a kit comprising two of the foot pedals of FIG. 23, together with certain components of the system of FIG. 2.

Referring now to FIG. 24, there is shown a perspective view of a kit constructed according to the present invention, the kit being represented generally by reference numeral 551.

Kit 551 may comprise a syringe/pump assembly 553, which may be identical to syringe/pump assembly 107. Syringe/pump assembly 553 may be packaged within an inner container 555 in preferably a sealed, sterile condition. Inner container 555 may, in turn, be packaged within an outer container 557 of blister packaging. A first foot pedal 559 and a second foot pedal 561, both of which may be identical to foot pedal 501, may be integrated into and form a part of outer container 557. Although not shown in FIG. 24, kit 551 may also include the wire for each of foot pedals 559 and 561. Each such wire may be connected to its respective foot pedal and may be stored within the space outside of inner container 555 but within outer container 557. In addition, kit 551 may further include the wires for syringe/pump assembly 553, which wires may be stored within inner container 555.

Kit 551 may be a disposable, single-use item.

Referring now to FIGS. 25(a) and 25(b), there are shown perspective and partly exploded perspective views, respectively, of a foot pedal assembly for use in system 101, said foot pedal assembly being constructed according to the present invention and being represented generally by reference numeral 601. Foot pedal assembly 601, which may be regarded as effectively having two independently-operable pedal portions, may be used in place of both first foot pedal 113 and second foot pedal 115.

Foot pedal assembly 601 may comprise a plurality of batteries 603, a battery container 605, a pair of resiliently-compressible tubes 607-1 and 607-2, and a pair of resiliently-compressible circuit rolls 609-1 and 609-2. Each of the foregoing components will now be discussed further below.

Batteries 603 may be conventional batteries and, more specifically, may be conventional disposable AA batteries. Although three batteries 603 are shown in the present embodiment, there could be as few as one or two batteries or as many as four or more batteries.

Battery container 605 may be appropriately dimensioned to hold batteries 603 in a series configuration. In addition, battery container 605 may also be appropriately dimensioned to be coaxially inserted into adjacent ends of resiliently-compressible tubes 607-1 and 607-2 so as to physically couple resiliently-compressible tubes 607-1 and 607-2 in a secure manner. Barbs 611 may be provided on the exterior of battery container 605 so enhance the interference fit between battery container 605 and resiliently-compressible tubes 607-1 and 607-2.

Resiliently-compressible tubes 607-1 and 607-2 may be generally identical to one another in size, shape and construction but may be marked and/or colored differently to facilitate their being differentiated by an operator. Resiliently-compressible tubes 607-1 and 607-2 may be molded or otherwise fashioned from blown polyethylene or a similarly suitable material that quickly returns to its original shape after being radially compressed.

Figure 26A:
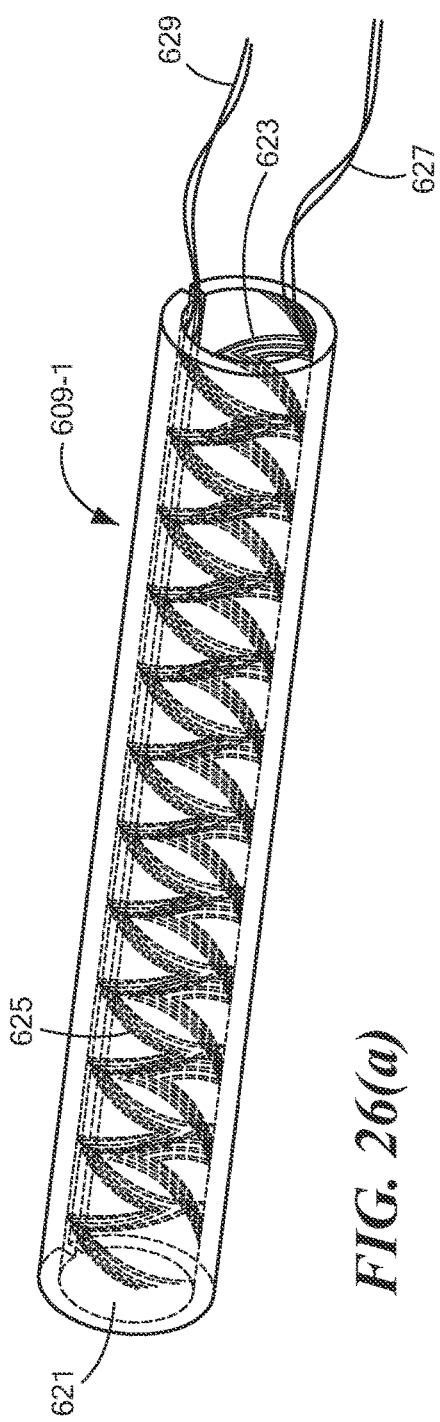
FIGS. 26(a) and 26(b) are views of one of the resiliently-compressible circuit rolls of FIG. 25(b) shown in rolled and unrolled states, respectively.
Figure 26B:
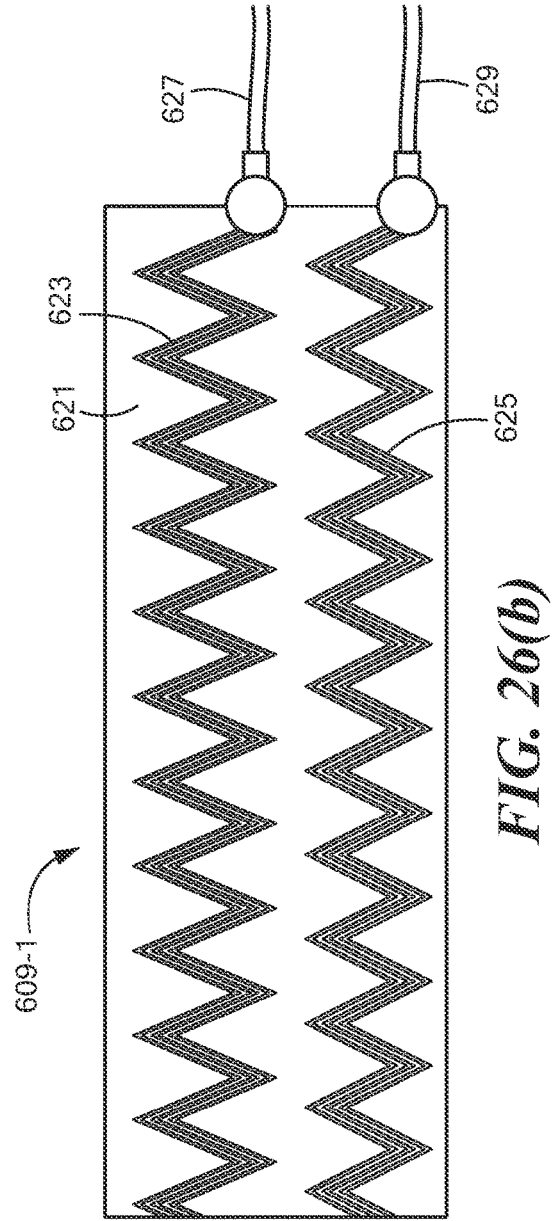

Resiliently-compressible circuit rolls 609-1 and 609-2, which may be coaxially disposed within appropriately dimensioned voids 616-1 and 616-2 of resiliently-compressible tubes 607-1 and 607-2, respectively, may be identical to one another; accordingly, the comments below pertaining to roll 609-1 may be applicable to roll 609-2. Roll 609-1, which is also shown separately in FIGS. 26(a) and 26(b), may comprise a sheet of electrically con-conductive material 621, such as MYLAR biaxally-oriented polyethylene terephthalate or a similarly suitable material. A pair of conductive elements 623 and 625, each of which may comprise, for example, a conductive ink, may be arranged on sheet 621. Conductive element 623 may be coupled to a cable 627, and conductive element 625 may be coupled to a cable 629. Conductive elements 623 and 625 may be appropriately positioned on sheet 621 so that radial compression of roll 609-1, such as when an operator steps on resiliently-compressible tube 607-1, causes conductive elements 623 and 625 to come into contact with one another. Consequently, by stepping on resiliently-compressible tube 607-1, one may close the switch defined by roll 609-1, and by stepping on resiliently-compressible tube 607-2, one may close the switch defined by roll 609-2.

Foot pedal assembly 601 may further comprise plugs 631 and 633. Plug 631 may be used to plug the outside end of void 616-1, and plug 633 may be used to plug the outside end of void 616-2.

Foot pedal assembly 601 may further comprise a cable 635, which may be connected at one end to a connector 637 and which may be coupled at its opposite end to each of circuit rolls 609-1 and 609-2.

As can be appreciated, because foot pedal assembly 601 includes a power source, the need for power source 109 is obviated when foot pedals 113 and 115 are replaced with foot pedal assembly 601.

Foot pedal assembly 601 may be a disposable, single-use item.

Figure 27:
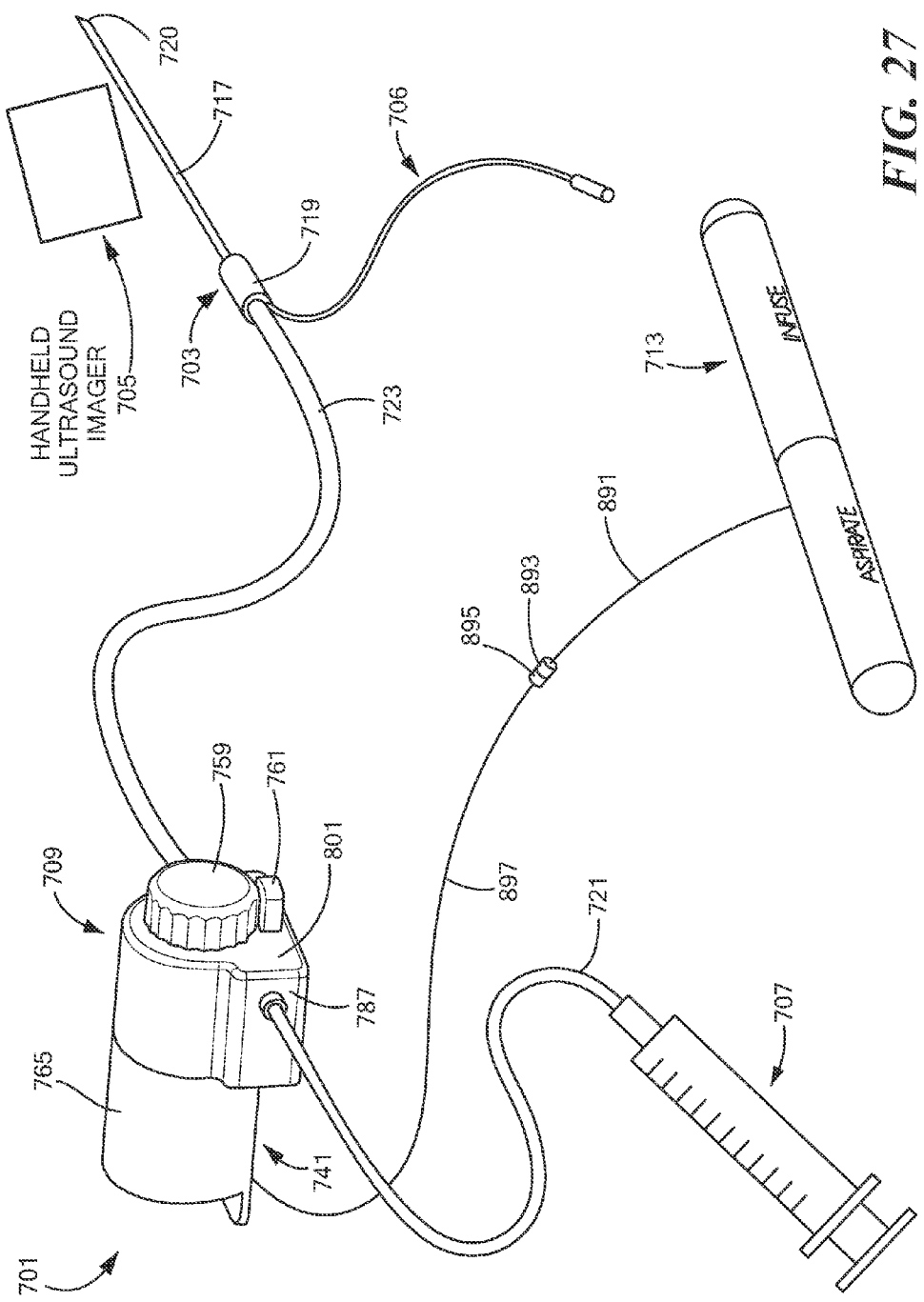
FIG. 27 is a perspective view, partly schematic, of a third embodiment of a system according to the present invention for controllably administering fluid to a patient and/or for controllably withdrawing fluid from the patient.

Referring now to FIG. 27, there is shown a perspective view, partly schematic, of a third embodiment of a system according to the present invention for controllably administering fluid so a patient and/or for controllably withdrawing fluid from the patient, the system being represented generally by reference numeral 701.

System 701 may include one or more of an infusion needle assembly 703, a handheld ultrasound imager 705, a nerve stimulator lead 706, a fluid receptacle 707, a peristaltic pump 709, and a foot pedal assembly 713. Each of the foregoing components will now be discussed further below.

Infusion needle assembly 703, which may be similar to infusion needle assembly 13, may be conventional and may include an infusion needle 717 and a needle hub 719. Infusion needle 717 may be a generally tubular or otherwise finger graspable member having a sharpened distal end 720 and may have a length of, for example, approximately 25 mm to approximately 150 mm and an outer diameter of, for example, approximately 25 gauge to approximately 18 gauge. Needle hub 719 may be a generally tabular member coaxially positioned around and fixed to infusion needle 717.

Handheld ultrasound imager 705 may be similar to handheld ultrasound imager 15 of system 11 and may be used in a similar fashion.

Nerve stimulator lead 706 may be similar to nerve stimulator lead 106 of system 101 and may be used in a similar fashion.

If desired, one or both of handheld ultrasound imager 705 and serve stimulator lead 706 may be omitted from system 701.

Fluid receptacle 707 may comprise a conventional syringe or other fluid receptacle, such as, but not limited to, an intravenous fluid bag.

Figure 28:
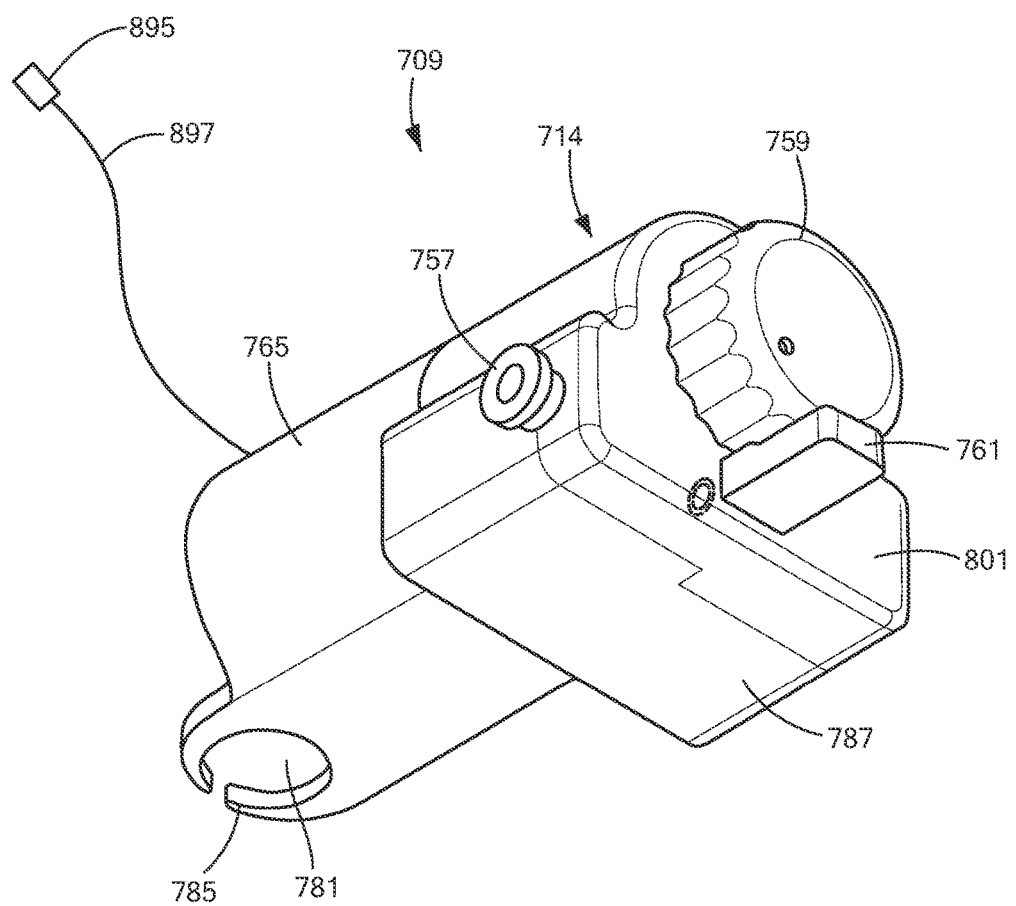
FIG. 28 is an enlarged bottom perspective view of the peristaltic pump shown in FIG. 27, together with its associated cable and connector.
Figure 29:
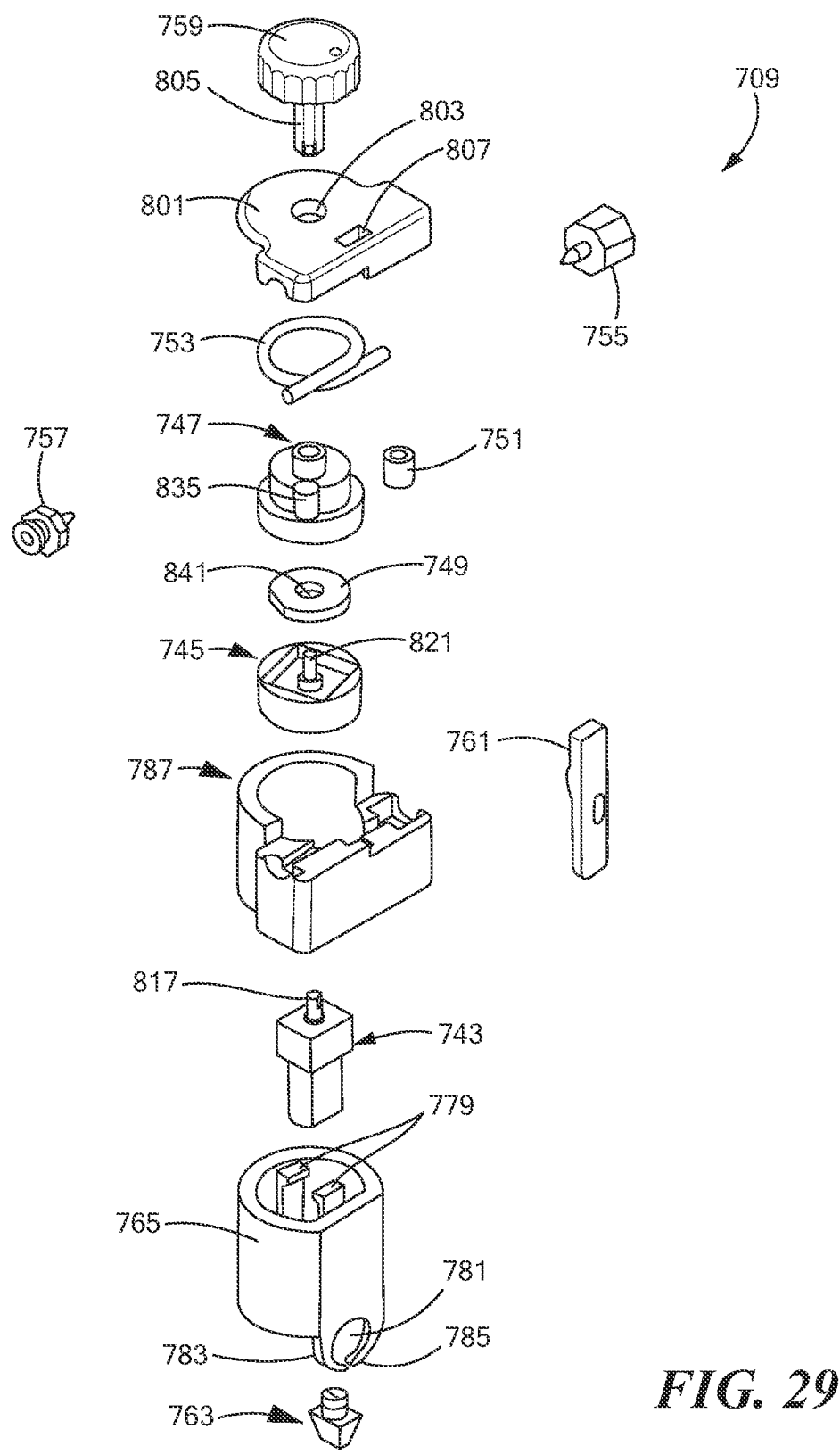
FIG. 29 is an exploded perspective view of the peristaltic pump shown in FIG. 27.
Figure 30B:
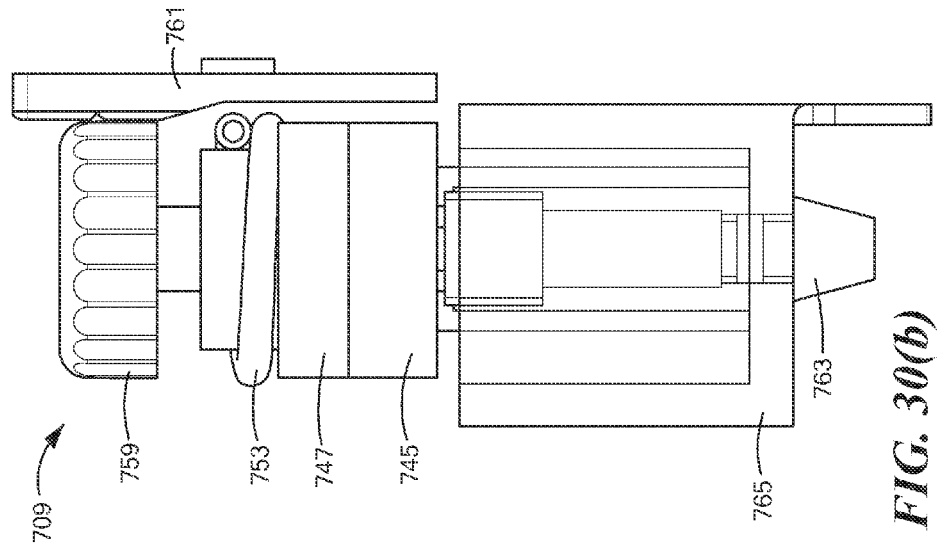
FIGS. 30(a) and 30(b) are side views of the peristaltic pump shown in FIG. 27, with a portion of the housing not being shown and with the tube stop positioned in engagement with and disengaged from respectively, the silicone tubing.
Figure 30A:
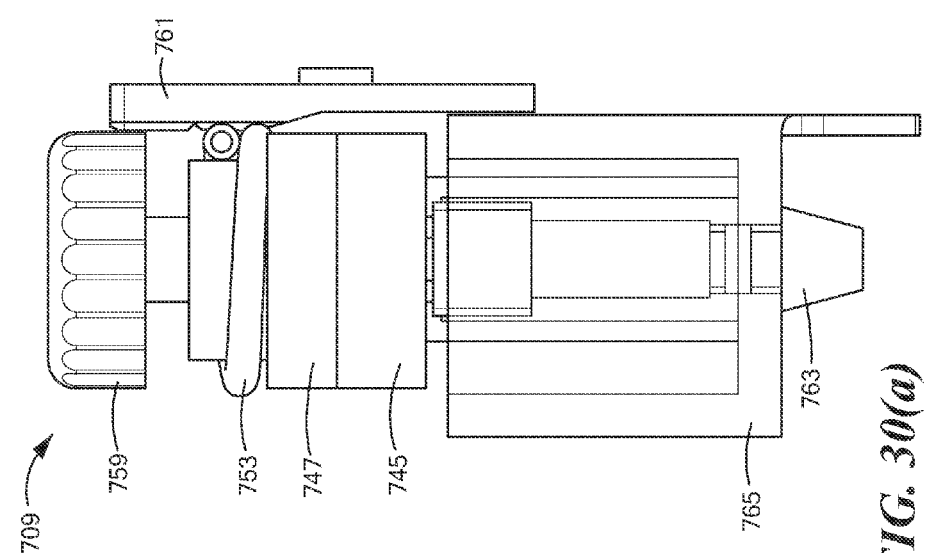

Peristaltic pump 709, which may be used to pump fluid from fluid receptacle 707 to infusion needle 717 or to pump fluid from infusion needle 717 to fluid receptacle 707, may be fluidly coupled to fluid receptacle 707 by a first length of tubing 721 and may be fluidly coupled to infusion needle assembly 703 by a second length of tubing 723. Referring now to FIGS. 28, 29, 30(*a*) and 30(*b*), peristaltic pump 709 is shown in greater detail.

Pump 709 may include one or more of a housing 741, a motor 743, a motor magnet 745, an upper magnet washer 747, a tab washer 749, a roller 751, a silicone tube 753, a male luer 755, a female luer 757, a knob 759, a tube stop 761, and a cable strain relief 763. Each of the foregoing components will now be discussed further below.

Figure 31A:
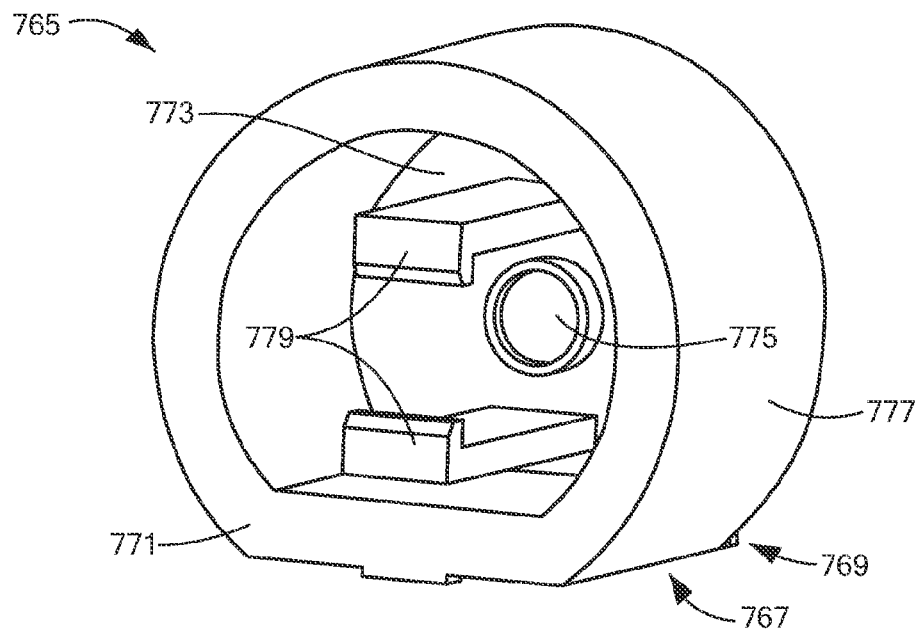
FIGS. 31(a) and 31(b) are enlarged top perspective and enlarged bottom perspective views, respectively, of the motor cover shown in FIG. 29.
Figure 31B:
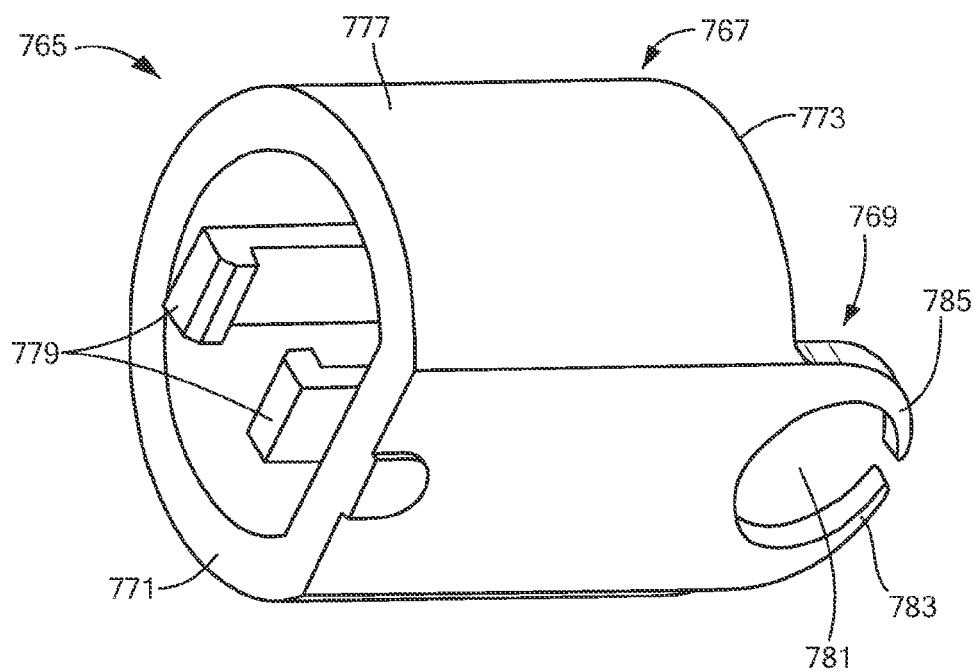

Housing 741 may comprise a motor cover 765. Motor cover 765, which is also shown separately in FIGS. 31(*a*) and 31(*b*), may be a unitary structure molded or otherwise fashioned from a suitably strong material, such as a suitable polymer, metal or other material. Motor cover 765 may comprise a tubular portion 767 and a tab portion 769. Tubular portion 767 may include a first end 771, which may be open, a second end 773, which may be closed, except for a small opening 775, and a side wall 777, which may be generally D-shaped in transverse cross section. Opening 775 may be used to receive cable strain relief 763, which, in turn, may be used to receive cable 897. A pair of resilient fingers 779 may extend generally longitudinally from second end 773 on opposite sides of opening 775. Fingers 779 may be used to securely receive motor 743. Tab portion 769 may be shaped to include a cloth grabber similar to those of clip 151 of assembly, the cloth grabber comprising an opening 781 defined at least in part by a pair of resilient fingers 783 and 785.

Figure 32A:
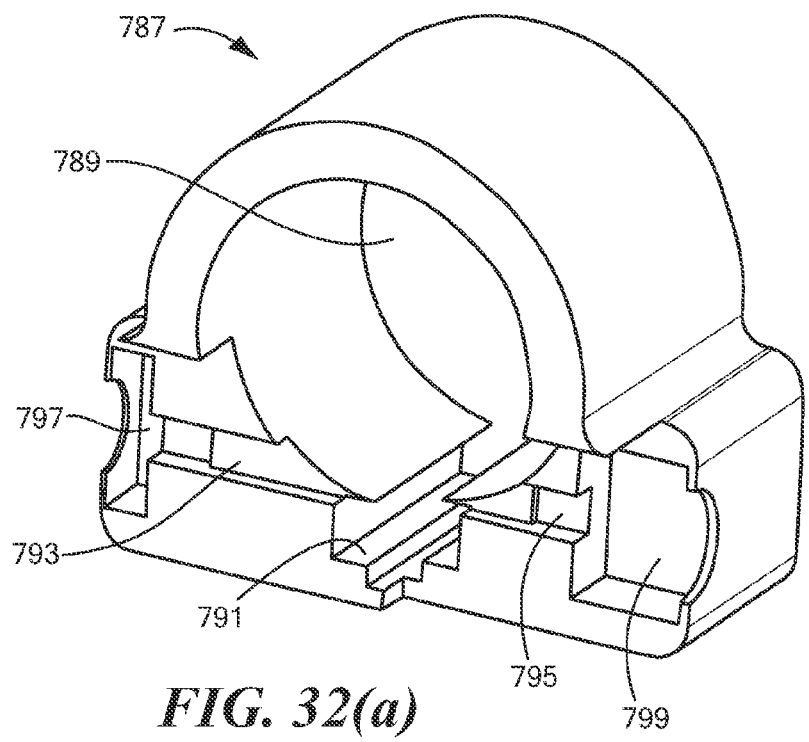
FIGS. 32(a) and 32(b) are enlarged top perspective and enlarged bottom perspective views, respectively, of the housing body shown in FIG. 29.
Figure 32B:
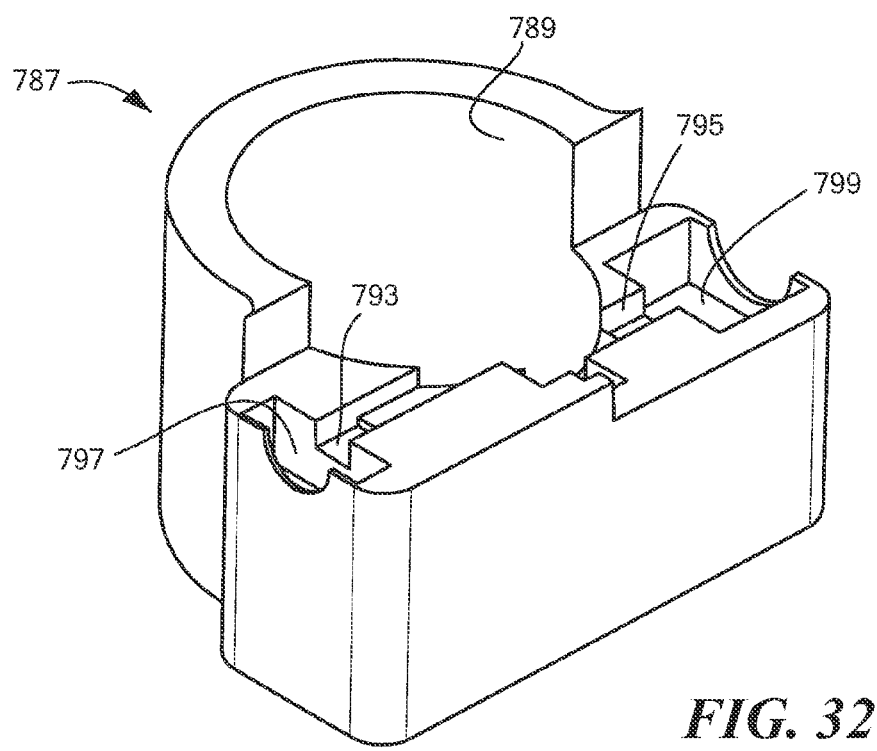

Housing 741 may further comprise a housing body 787. Housing body 787, which is also shown separately in FIGS. 32(*a*) and 32(*b*), may be a unitary structure molded or otherwise fashioned from a suitably strong material, such as a suitable polymer, metal or other material. Housing body 787 may be shaped to include an opening 789, which may be adapted to receive motor magnet 745, tab washer 749, upper magnet washer 747, and silicone tube 753. Housing body 787 may also be shaped to include a slot 791, which may be adapted to receive tube stop 761 in such a way that tube stop 761 may be slidably adjustable within slot 791. Housing body 787 may additionally be shaped to include a pair of grooves 793 and 795, which may be adapted to receive opposing ends of silicone tube 753. Housing body 787 may further be shaped to include a first compartment 797, which may be adapted to receive female luer 757, and a second compartment 799, which may be adapted to receive male luer 755.

Figure 33A:
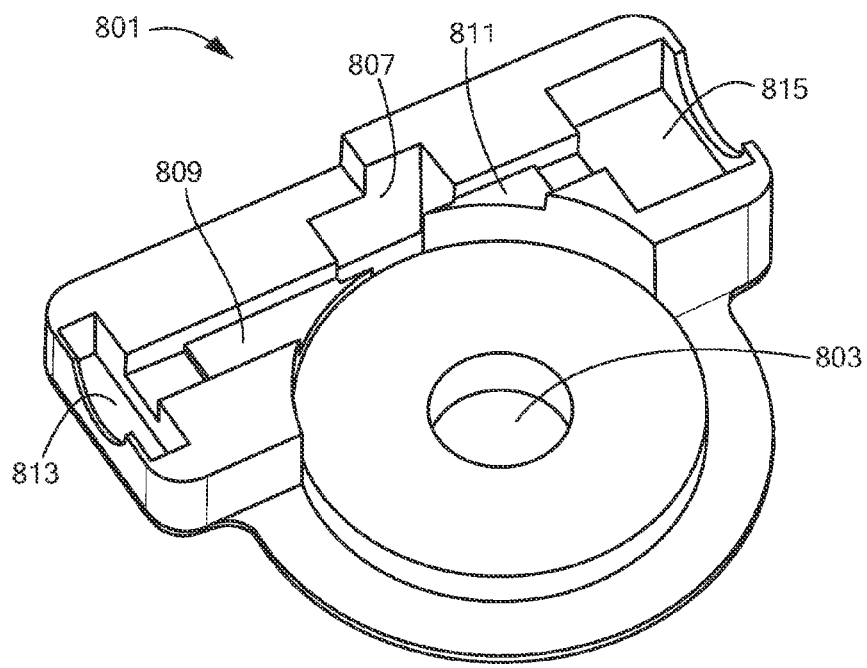
FIGS. 33(a) and 33(b) are enlarged perspective views, respectively, of the housing cover shown in FIG. 29.
Figure 33B:
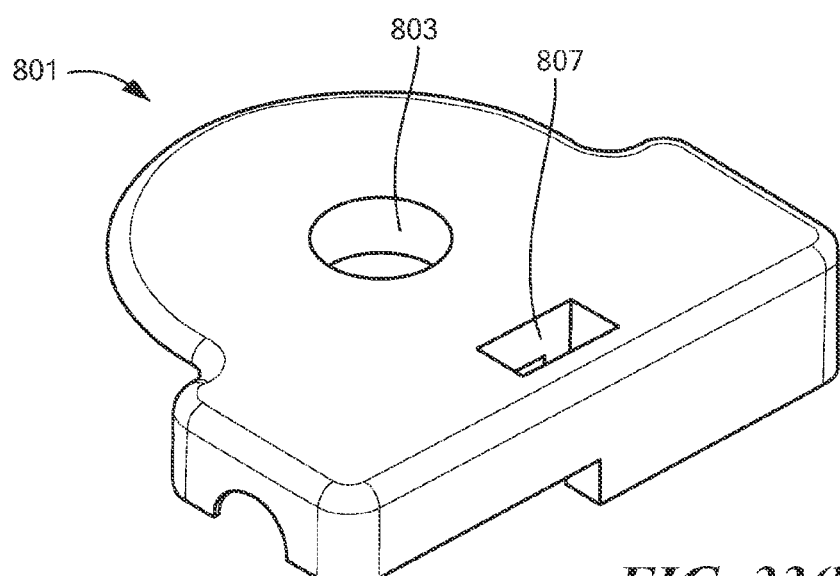

Housing 741 may further comprise a housing cover 801. Housing cover 801, which is also shown separately in FIGS. 33(*a*) and 33(*b*), may be a unitary structure molded or otherwise fashioned from a suitably strong material such as a suitable polymer, metal or other material. Housing cover 801, which may be shaped to mate with housing body 787, may include a first opening 803, which may be adapted to coaxially receive a shaft 805 of knob 759 in such a way that shaft 805 may be freely rotatable within opening 803. Housing cover 801 may also include a second opening 807, which may be adapted to receive tube stop 761 in such a way that tube stop 761 may be slidably adjustable within second opening 807. Housing cover 801 may additionally be shaped to include a pair of grooves 809 and 811, which may be adapted to receive opposing ends of silicone tube 753. Housing cover 801 may further be shaped to include a first compartment 813, which may be adapted to receive female luer 757, and a second compartment 815, which may be adapted to receive male luer 755.

Figure 34:
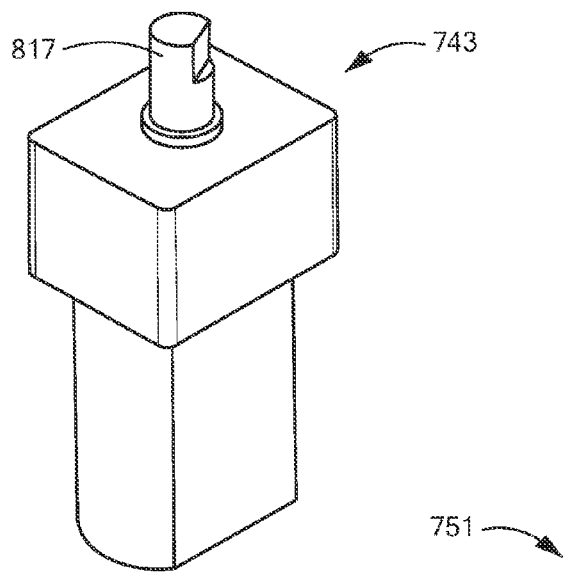
FIG. 34 is tar enlarged perspective view of the motor shown in FIG. 29.

Motor 743, which is also shown separately in FIG. 34, may be a conventional bi-directional DC motor. Motor 743 may comprise a rotatable shaft 817.

Figure 35A:
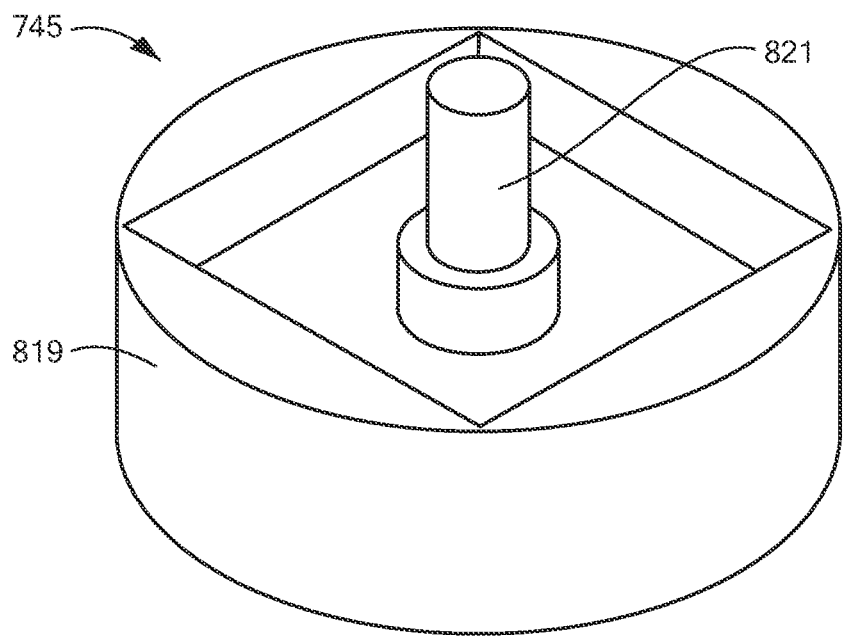
FIGS. 35(a) and 35(b) are enlarged top perspective and enlarged bottom perspective views, respectively, of the motor magnet shown in FIG. 29.
Figure 35B:
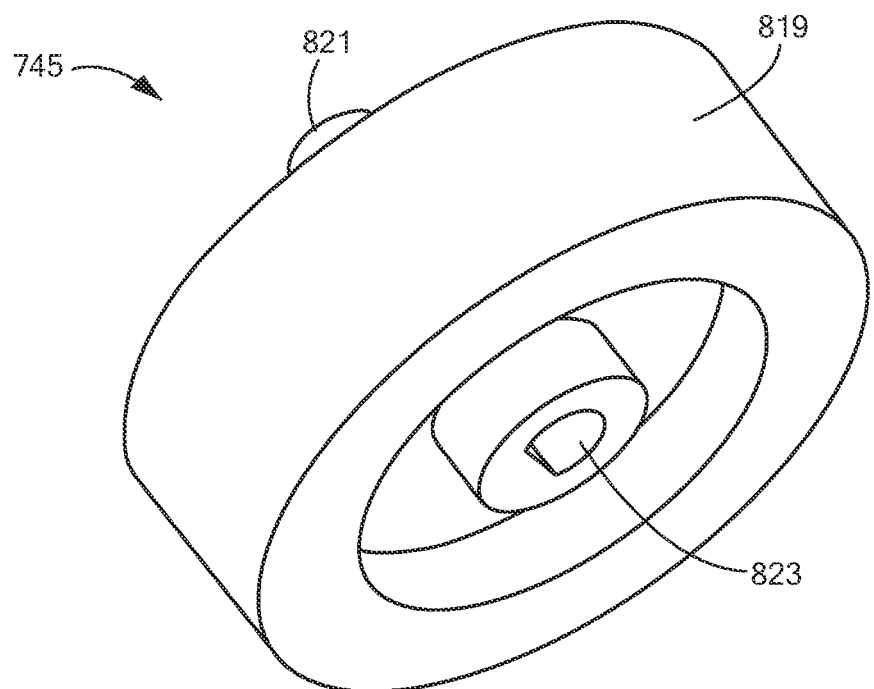

Motor magnet 745, which is also shown separately in FIGS. 35(*a*) and 35(*b*), may be positioned within opening 789 of housing body 787 and may be shaped to comprise a base 819 and a shaft 821, wherein shaft 821 may extend upwardly from base 819. Shaft 821 may include a cavity 823, which may be appropriately dimensioned to receive rotatable shaft 817 of motor 743 in such a way that shaft 821 may be mechanically coupled for rotation to rotatable shaft 817 of motor 743.

Figure 36A:
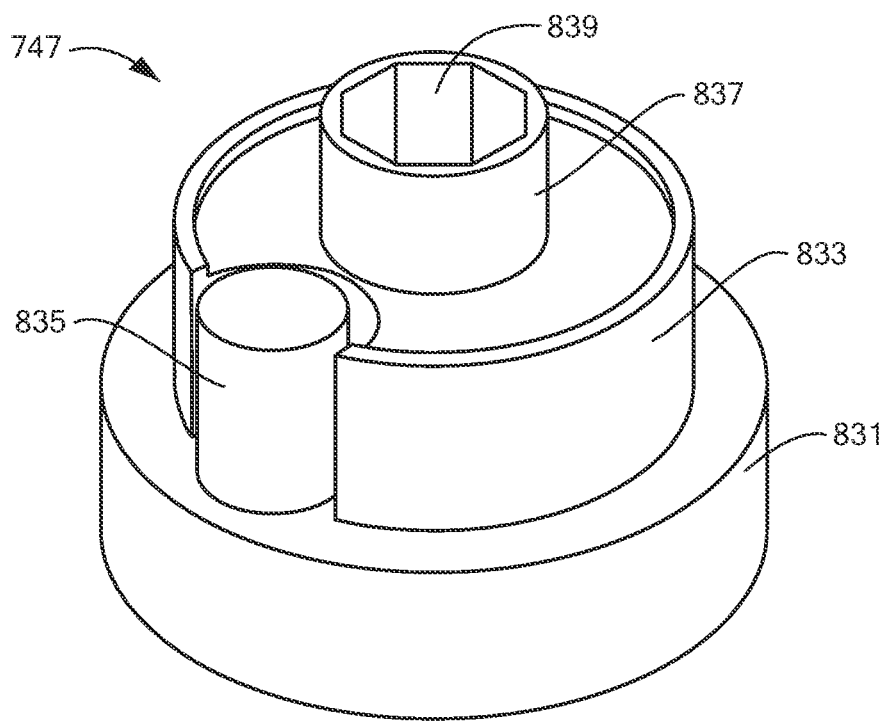
FIGS. 36(a) and 36(b) are enlarged top perspective and enlarged bottom perspective views, respectively, of the upper magnet washer shown in FIG. 29.
Figure 36B:
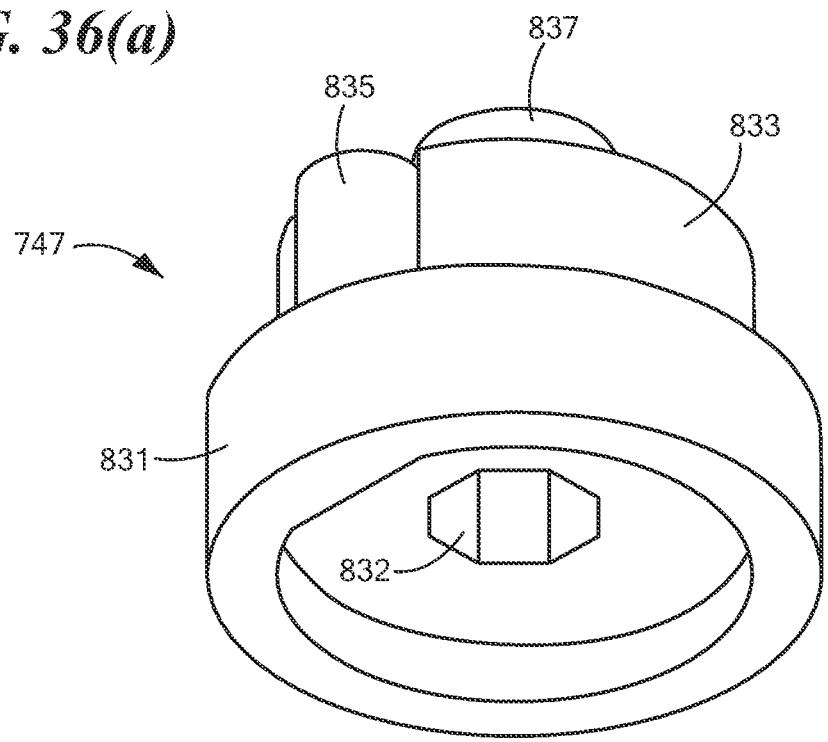

Upper magnet washer 747, which is also shown separately in FIGS. 36(a) and 36(b), may be positioned within opening 789 of housing body 787 and may be shaped to include a base 831. Base 831 may be shaped to include a bore 832 adapted to receive shaft 821 of motor magnet 745. A first projection 833 may extend upwardly coaxially from base 831, and a second projection 835 may extend upwardly off-axis from base 831. A third projection 837 may extend upwardly coaxially from first projection 833. A bore 839 may be provided in third projection 837. Bore 839 may be appropriately dimensioned to receive shaft 805 of knob 759 in such a way that third projection 837 may be mechanically coupled for rotation to shaft 805 of knob 759. In this manner, as will be discussed further below, manual rotation of knob 759 may be used to effect the rotation of upper magnet washer 747, for example, to align second projection 835 with tube stop 761.

Tab washer 749 may be positioned between motor magnet 745 and upper magnet washer 747, with tab washer 749 having an opening 841 through which shaft 821 of motor magnet 745 may be coaxially inserted. The combination of motor magnet 745, upper magnet washer 747, and tab washer 749 may act as a magnetic clutch, wherein upper magnet washer 747 becomes decoupled from rotation to motor magnet 745 when the pressure in the fluid path exceeds a predetermined threshold.

As can readily be appreciated, pump 709 may be modified to replace the magnetic clutch described above with a mechanical clutch which slips at a predetermined torque to limit the forces delivered to the pumping mechanism. Alternatively, a current limiter may be placed between the battery and the motor to limit the torque delivered, or a pressure limit switch may be provided in the fluid path to cutoff the electric power to the motor, or a pressure relief valve may be provided to relieve the pressure by dumping the fluid from the fluid path.

Figure 37:
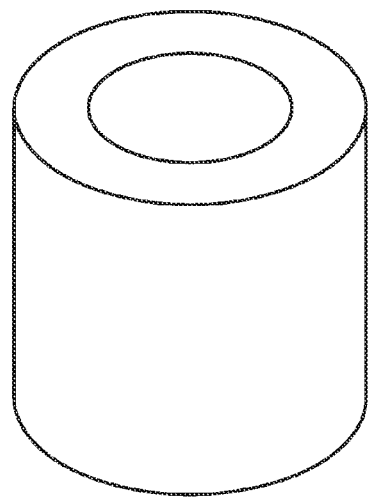
FIG. 37 is an enlarged perspective view of the roller shown in FIG. 29.

Roller 751, which is also shown separately in FIG. 37, may be mounted coaxially over second projection 835 of upper magnet washer 747. Roller 751 may be appropriately dimensioned to engage silicone tube 753 sufficiently to pinch shut silicone tube 753. In this manner, as upper magnet washer 747 rotates, roller 751 may serve to force fluid along the longitudinal axis of silicone tube 753.

Figure 38:
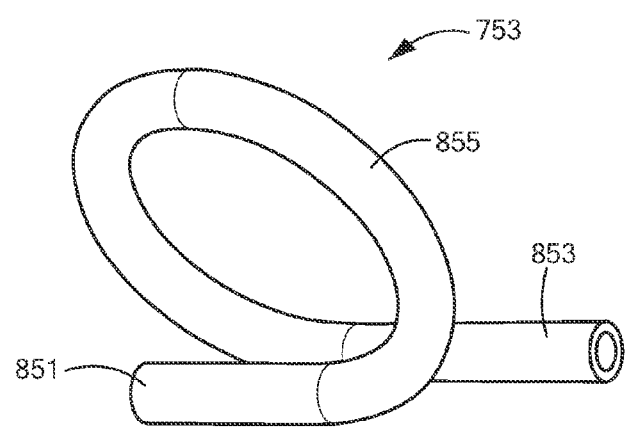
FIG. 38 is an enlarged perspective view of the silicone tubing shown in FIG. 29.

Silicone tube 753, which is also shown separately in FIG. 38, may have a first end 851, a second end 853, and a looped portion 855. First end 851 may be positioned in groove 793 of housing body 787 and in groove 809 of housing cover 801. Second end 853 may be positioned in groove 795 of housing body 787 and in groove 811 of housing cover 801. Looped portion 855 may be seated on base 831 of upper magnet washer 747 and may be wrapped around first projection 833 and second projection 835 of upper magnet washer 747.

Figure 39A:
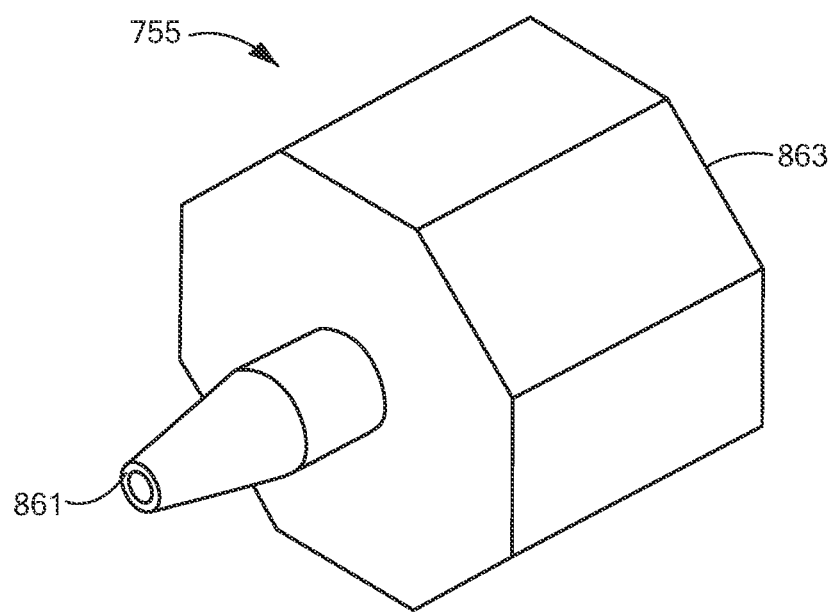
FIGS. 39(a) and 39(b) are enlarged proximal perspective and enlarged distal perspective views, respectively, of the male luer shown in FIG. 29.
Figure 39B:
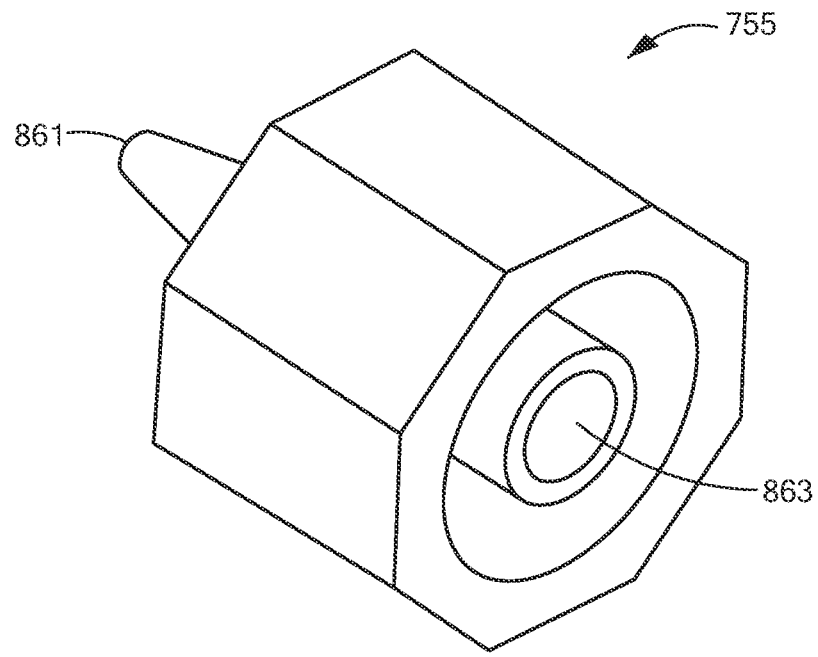

Male luer 755, which is also shown separately in FIGS. 39(a) and 39(b), may be a generally tubular unitary structure molded or otherwise fashioned from a suitably strong material, such as a suitable polymer, metal or other material. Male luer 755 may be shaped to include a first end 861 and a second end 863. First end 861 may be adapted for insertion into second end 853 of silicone tube 753. Second end 863 may be adapted to be mated with a female connector (not shown) on second tubing 723 (see FIG. 27).

Figure 40A:
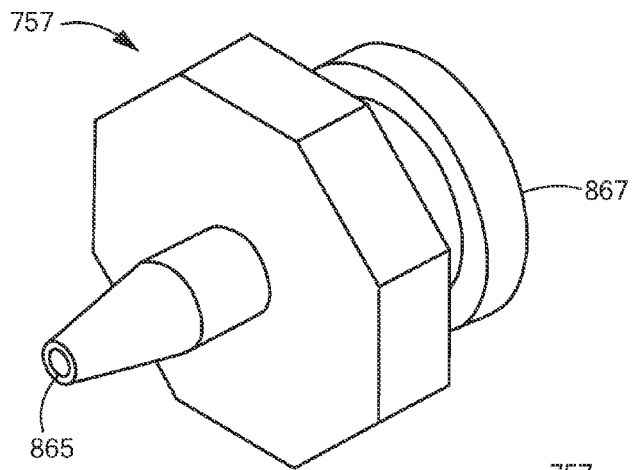
FIGS. 40(a) and 40(b) are enlarged proximal perspective and enlarged distal perspective views, respectively, of the female luer shown in FIG. 29.
Figure 40B:
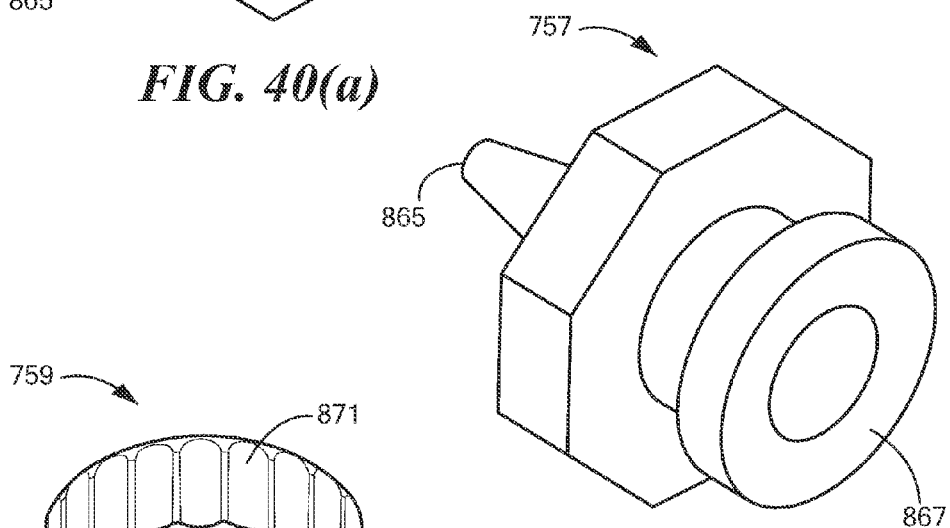

Female luer 757, which is also shown separately in FIGS. 40(a) and 40(b), may be a generally tubular unitary structure molded or otherwise fashioned from a suitably strong material, such as a suitable polymer, metal or other material. Female luer 757 may be shaped to include a first end 865 and a second end 867. First end 865 may be adapted for insertion into first second end 851 of silicone tube 753. Second end 867 may be adapted to be mated with a male connector (not shown) on first tubing 721 (see FIG. 27).

Figure 41:
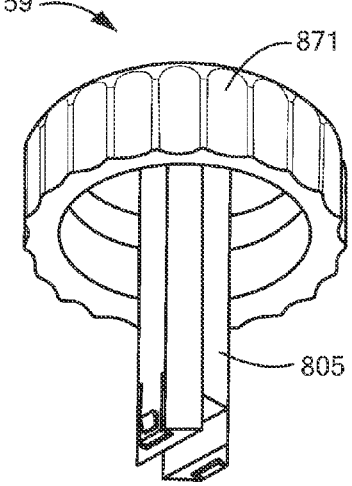
FIG. 41 is an enlarged perspective view of the knob shown in FIG. 29.

Knob 759, which is also shown separately in FIG. 41, may be a unitary structure molded or otherwise fashioned from a suitably strong material, such as a suitable polymer, metal or other material. Knob 759 may comprise a head 871 and shaft 805. Shaft 905 may be appropriately dimensioned to for insertion through opening 803 in housing cover 801 and into engagement with bore 839 of upper magnet washer 747.

Figure 42A:
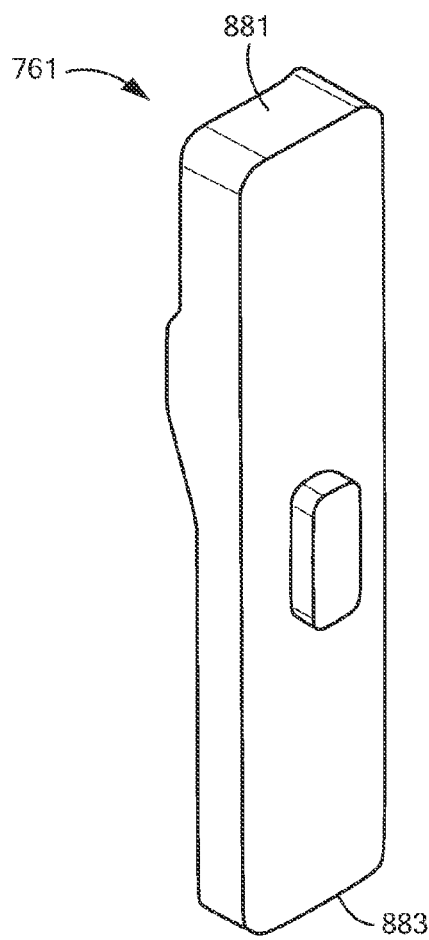
FIGS. 42(a) and 42(b) are enlarged front perspective and enlarged rear perspective views, respectively, of the tube stop shown in FIG. 29.
Figure 42B:
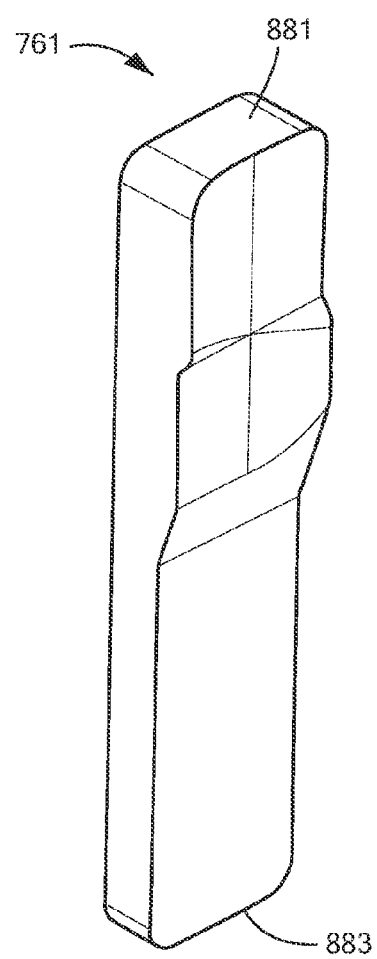

Tube stop 761, which is also shown separately in FIGS. 42(a) and 42(b), may be a unitary structure molded or otherwise fashioned from a suitably strong material, such as a suitable polymer, metal or other material. Tube stop 761 may be shaped to have a comparatively greater thickness at a first end 881 and a comparatively lesser thickness at a second end 893. A reason for the non-uniform thickness of tube stop 761 is set forth below.

A premise for the inclusion of pump 709 in system 701 is to allow fluid to be pumped automatically without needing so handle a syringe in the traditional way. However, under certain conditions, it may be essential or desirable to pump the fluid manually. Consequently, pump 709 should be designed to allow the free flow of fluid through pump 709 under syringe control and to allow the same syringe dexterity and back pressure sensitivity for the doctor.

For this reason, pump 709 may be adjustable between a manual mode and an automatic mode. An automatic mode may be understood to mean that the electric motor moves the rotor and pumps fluid with no hands on the syringe. There are several reasons why manual mode may be required or desired: (1) if the motor fails part-way through drug administration infusion or aspiration; (2) if the doctor chooses to fill the syringe manually with the pump attached to the output port of the syringe; (3) if the doctor chooses to prime the pump housing, tubing and needle manually, instead of automatically with the motor.

To allow pump 709 have a manual mode capability, pump 709 includes an adjustable back plate, i.e., tube stop 761, where the tubing crosses-over or loops onto itself. The thickness of tube stop 761 is designed so that it can achieve two "states"—tube compression or no compression at a particular point in the tube housing. To this end, tube stop 761 has one thick end and one thin end. The profile between the two ends is a ramp which allows smooth transition from one state to the other as tube stop 761 is moved from its compressing position to a non-compressing position.

With the motor turned off, roller 751 may be rotated manually to the tube cross-over point by the use of knob 759. Positioning roller 751 manually ensures that roller 751 is aligned with tube stop 761. This is because the motor could stop anywhere in its 360 degree rotation path. When roller 751 is aligned and tube stop 761 is slid into a non-compressing condition by the operator, fluid can pass through silicone tube 753 freely with no restriction. Reinstating automatic (motor-powered mode) is as simple as sliding tube stop 761 back into a compressing position.

As can be appreciated, although pump 709 is described herein as being of the type comprising a single roller 751, pump 709 may be modified to include a plurality of rollers.

Referring back now to FIG. 27, foot pedal assembly 713, which may be identical to foot pedal assembly 601, may be electrically coupled by a cable 891 to a connector 893. Connector 893, in turn, may be connected to a connector 895, which, in turn, may be electrically coupled to motor 743 (see FIG. 29) by a cable 897.

It should be recognized that foot pedal assembly 713 may be replaced by a pair of conventional foot pedals or by a pair of foot pedals similar to foot pedal 501.

If desired, one or more components of system 701, and in fact, preferably all of the components of system 701, except possibly for handheld ultrasound imager 705, may be disposable, single-use items. This single-use feature may be desirable as it may provide a convenient way of ensuring the sterility of system 701 in an operating room or surgery center environment.

Figure 43:
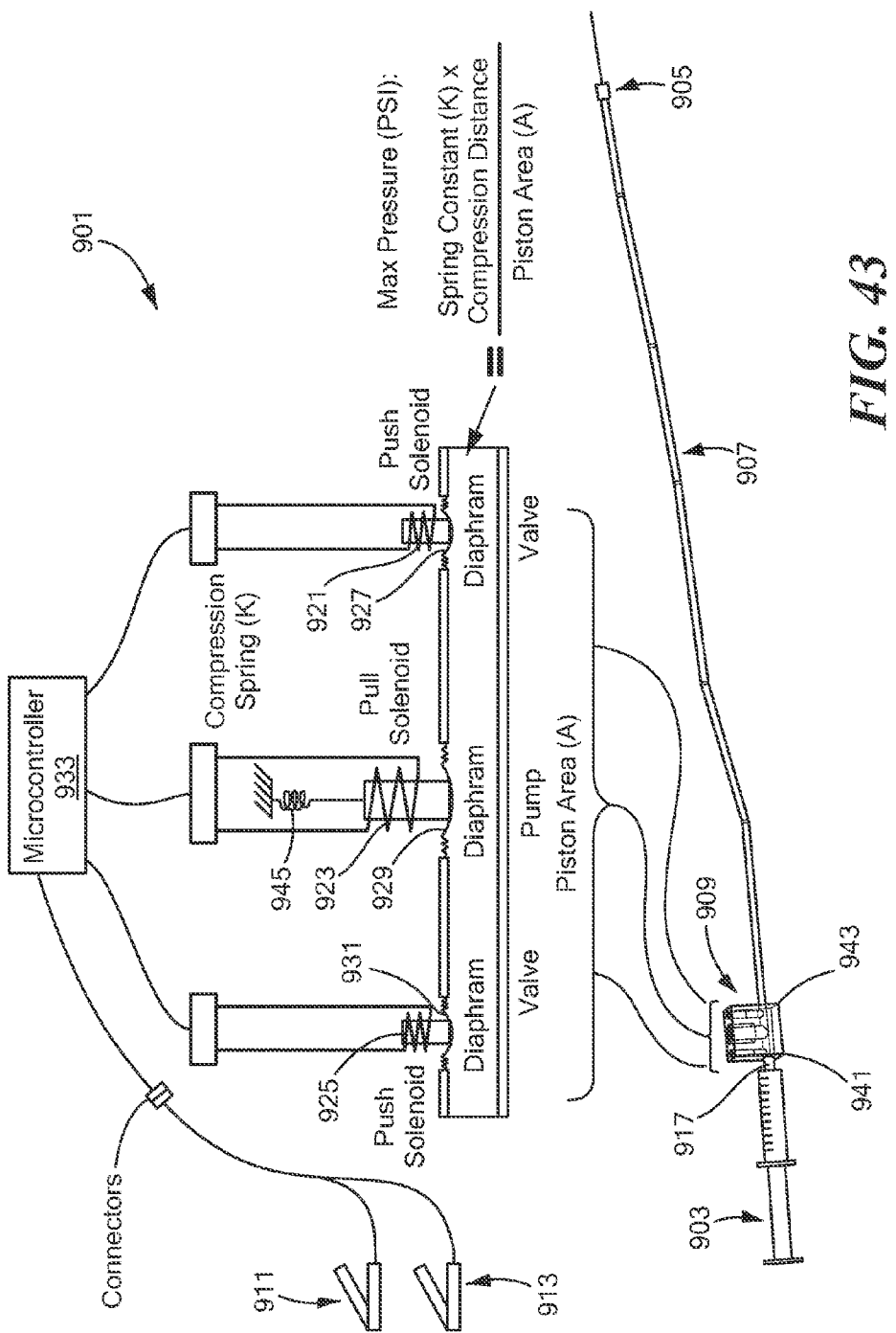
FIG. 43 is a perspective view, partly schematic, of a fourth embodiment of a system according to the present invention for controllably administering fluid to a patient and/or for controllably withdrawing fluid from the patient.

Referring now to FIG. 43, there is shown a fourth embodiment of a system according to the present invention for controllably administering fluid to a patient and/or for controllably withdrawing fluid from the patient, the system being represented generally by reference numeral 901.

System 901 may comprise one or more of a syringe 903, an infusion needle assembly 905, extension tubing 907, a pump 909, a first foot pedal 911 and a second foot pedal 913. Although not shown, system 901 may also comprise one or both of a handheld ultrasound imager and a nerve stimulator lead.

Syringe 903, infusion needle assembly 905 and extension tubing 907 may be conventional. First foot pedal 911 and second foot pedal 913 may take the form of any of the conventional or novel foot pedals or foot pedal assemblies discussed herein.

Pump 909 may comprise a female luer connector (not shown) that may be connected directly to the male luer connector 917 of syringe 903. Pump 909 may further comprise three solenoids 921, 923 and 925 that control a distal valve diaphragm 927, a pump diaphragm 929, and a proximal valve diaphragm 931, respectively. When powered, the microcontroller 933 has three states: non-pumping, infusing, and aspirating. In the non-pumping state, the diaphragms are in the normally open position so there is a clear fluid path from the proximal end 941 of pump 909 to the distal end 943 of pump 909. In either the infusion or aspiration states, solenoids 921, 923, and 925 are each sequenced in time to aspirate from one end of the pump 909 with one of valves 927 and 931 open and the other of valves 927 and 931 closed and with the pump diaphragm 929 pulled to the up position against the force of the compression spring 945. In the next time sequence, the valves 927 and 931 are reversed from open to closed and closed to open, and the pump diaphragm 929 is allowed to be driven by the spring 945. The fluid pressure limit is set by the product of the displacement of the spring 945 and the spring constant divided by the area of the diaphragm 929. The flow rate will be determined by the fixed rate of the time sequencing and the pressure in the fluid path. The higher the time sequencing, the higher the flow rate. The higher the pressure, the lower the flow rate. In the event of an occlusion in the fluid path, the fluid pressure will build up, which will reduce the linear displacement of the pump diaphragm 929 until it ultimately has no displacement as the maximum allowed pressure, thereby reducing the flow rate to zero. This pump has a maximum pressure allowable in the fluid path and a variable flow rate which is a function of the pressure in the fluid path. By comparison, most traditional syringe pumps have controlled flow rates with a maximum pressure limit threshold.

Figure 44:
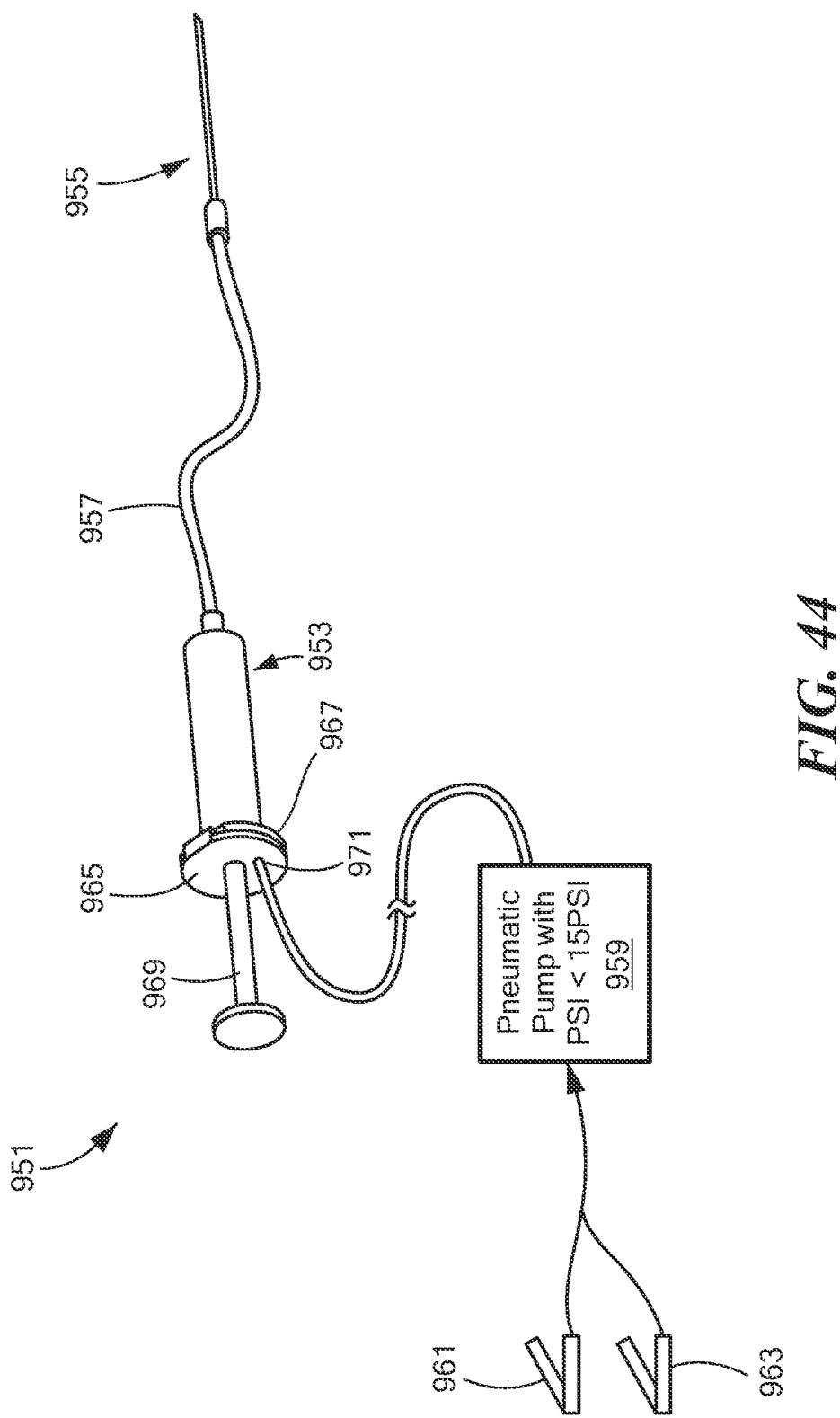
FIG. 44 is a perspective view, partly schematic, of a fifth embodiment of a system according to the present invention for controllably administering fluid to a patient and/or for controllably withdrawing fluid from the patient.

Referring now to FIG. 44, there is shown a fifth embodiment of a system according to the present invention for controllable administering fluid to a patient and/or for controllably withdrawing fluid from the patient, the system being represented generally by reference number 951.

System 951 may comprise one or more of a syringe 953, an infusion needle assembly 955, extension tubing 957, a pump 959, a first foot pedal 961 and a second foot pedal 963. Although not shown, system 951 may also comprise one or both of a handheld ultrasound imager and a nerve stimulator lead.

Infusion needle assembly 955 and extension tubing 957 may be conventional. First foot pedal 961 and second foot pedal 963 may take the form of any of the conventional or novel foot pedals or foot pedal assemblies discussed herein.

Pump 959 may be a pneumatic pump that pumps at a pressure less than the threshold pressure one wishes not to exceed, e.g., 15 psi for nerve block procedures. An end cap 965 may be positioned at the proximal flange 967 of syringe 953 to create a sealed cavity between end cap 965 and distal end of plunger 969. A pneumatic port 971 may be provided in end cap 965, which accepts either positive pneumatic gauge pressure to infuse equivalent to the pressure limit imposed on the pneumatic pump 959 with foot pedals 961 and 963 by driving plunger 969 distally or accepts negative pneumatic gauge pressure to aspirate by driving plunger 969 proximally.

Figure 45:
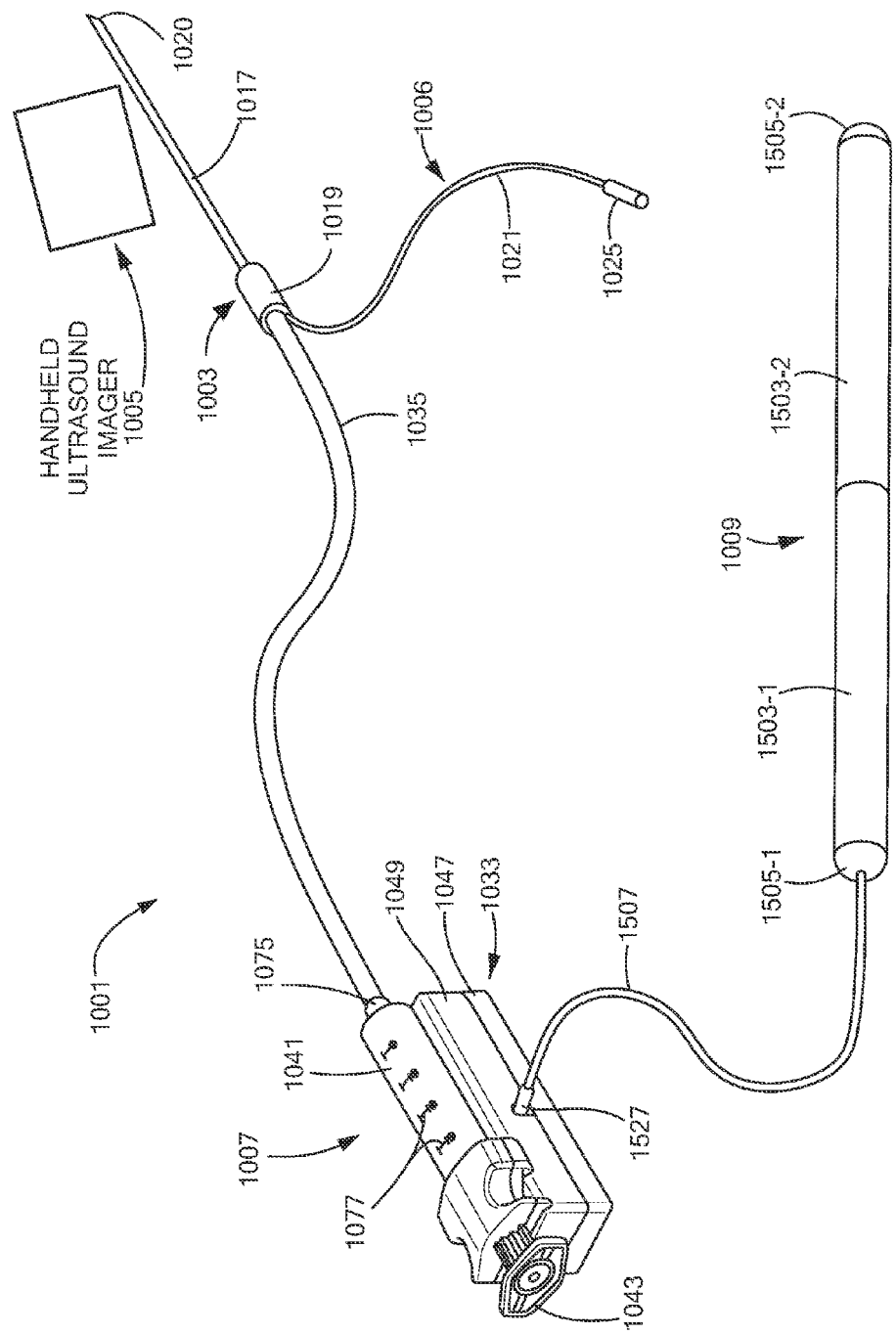
FIG. 45 is a perspective view, partly schematic, of a sixth embodiment of a system according to the present invention for controllably administering fluid to a patient and/or for controllably withdrawing fluid from the patient.

Referring now to FIG. 45, there is shown a perspective view, partly schematic, of a sixth embodiment of a system according to the present invention for controllably administering fluid to a patient and/or for controllably withdrawing fluid from the patient, the system being represented generally by reference numeral 1001.

System 1001 may include one or more of an infusion needle assembly 1003, a handheld ultrasound imager 1005, a nerve stimulator lead 1006, a syringe/pump assembly 1007, and a foot pedal assembly 1009. Each of the foregoing components will now be discussed further below.

Infusion needle assembly 1003, which may be similar to infusion needle assembly 13, may be conventional and may include an infusion needle 1017 and a needle hub 1019. Infusion needle 1017 may be a generally tubular member having a sharpened distal end 1020 and may have a length of, for example, approximately 25 mm to approximately 150 mm and an outer diameter of, for example, approximately 25 gauge to approximately 18 gauge. Needle hub 1019 may be a generally tubular or otherwise finger graspable member coaxially positioned around and fixed to infusion needle 1017.

Handheld ultrasound imager 1005 may be similar so handheld ultrasound imager 15 of system 11 and may be used in a similar fashion.

Nerve stimulator lead 1006 may comprise a wire 1021 or other electrically conductive member having a first end inserted into needle hub 1019 and in contact with infusion needle 1017 and a second end coupled to an electrically conductive connector 1025. At least a portion of the length of wire 1021 between its first and second ends may be coaxially covered with an electrically insulating jacket (not shown). Connector 1025 may be coupled to a source of electrical current, and nerve stimulator lead 1006 may be used in the fashion described above to cause a body portion contacted by infusion needle 1017 to involuntarily twitch, thereby providing a visual indicator to the physician of the location of infusion needle 1017.

If desired, one or both of handheld ultrasound imager 1005 and nerve stimulator lead 1006 may be omitted from system 1001.

Figure 46A:
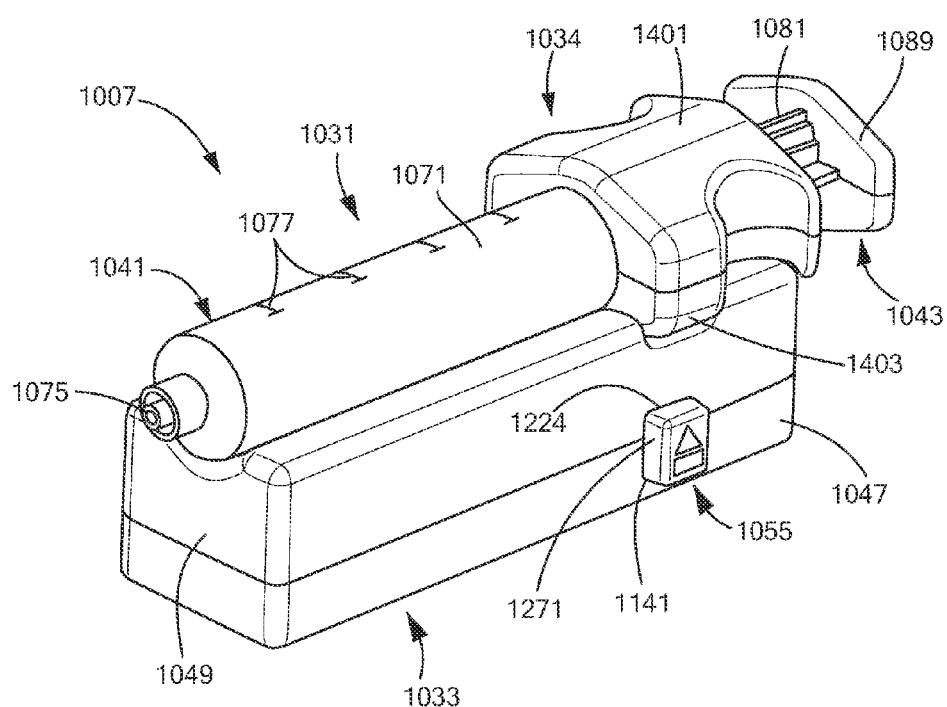
FIGS. 46(a) and 46(b) are perspective views of the syringe/pump assembly of FIG. 45, showing the syringe and the pump coupled to one another via the adaptor and decoupled from one another, respectively.
Figure 46B:
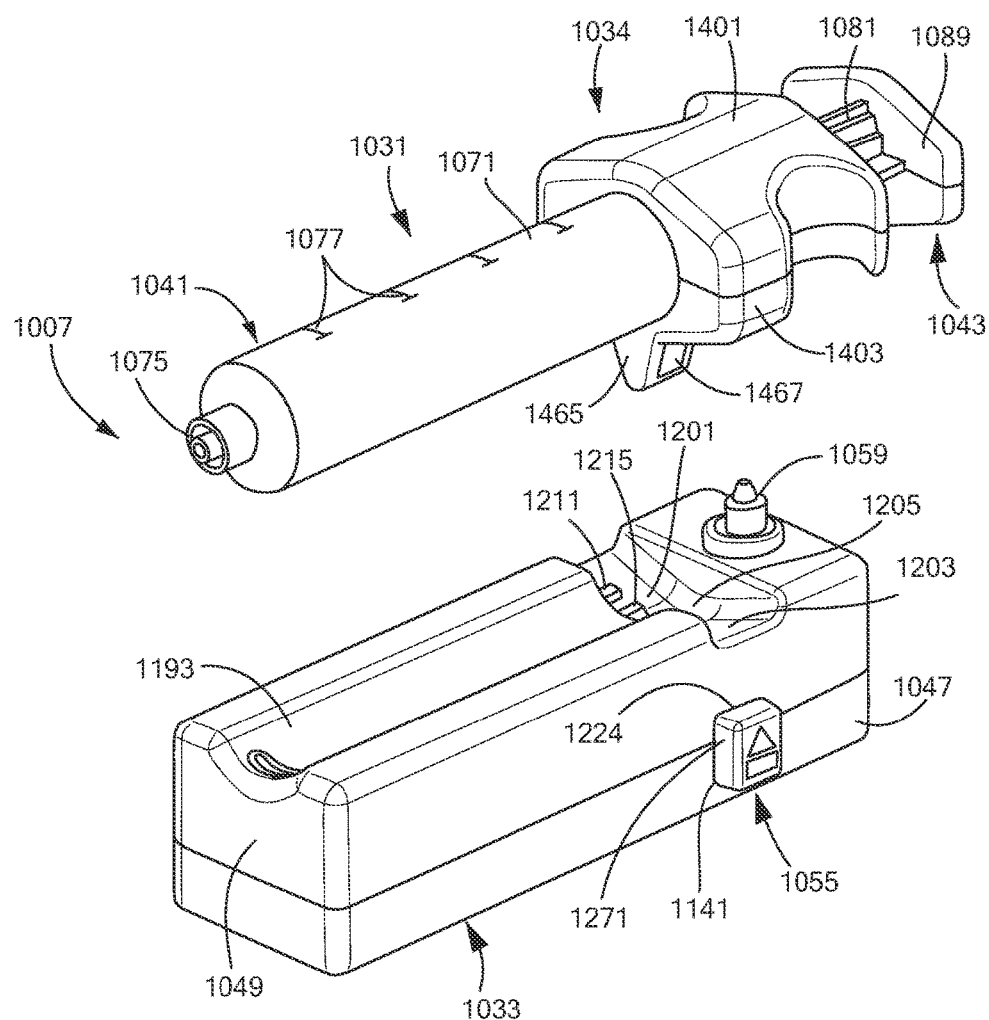
Figure 46C:
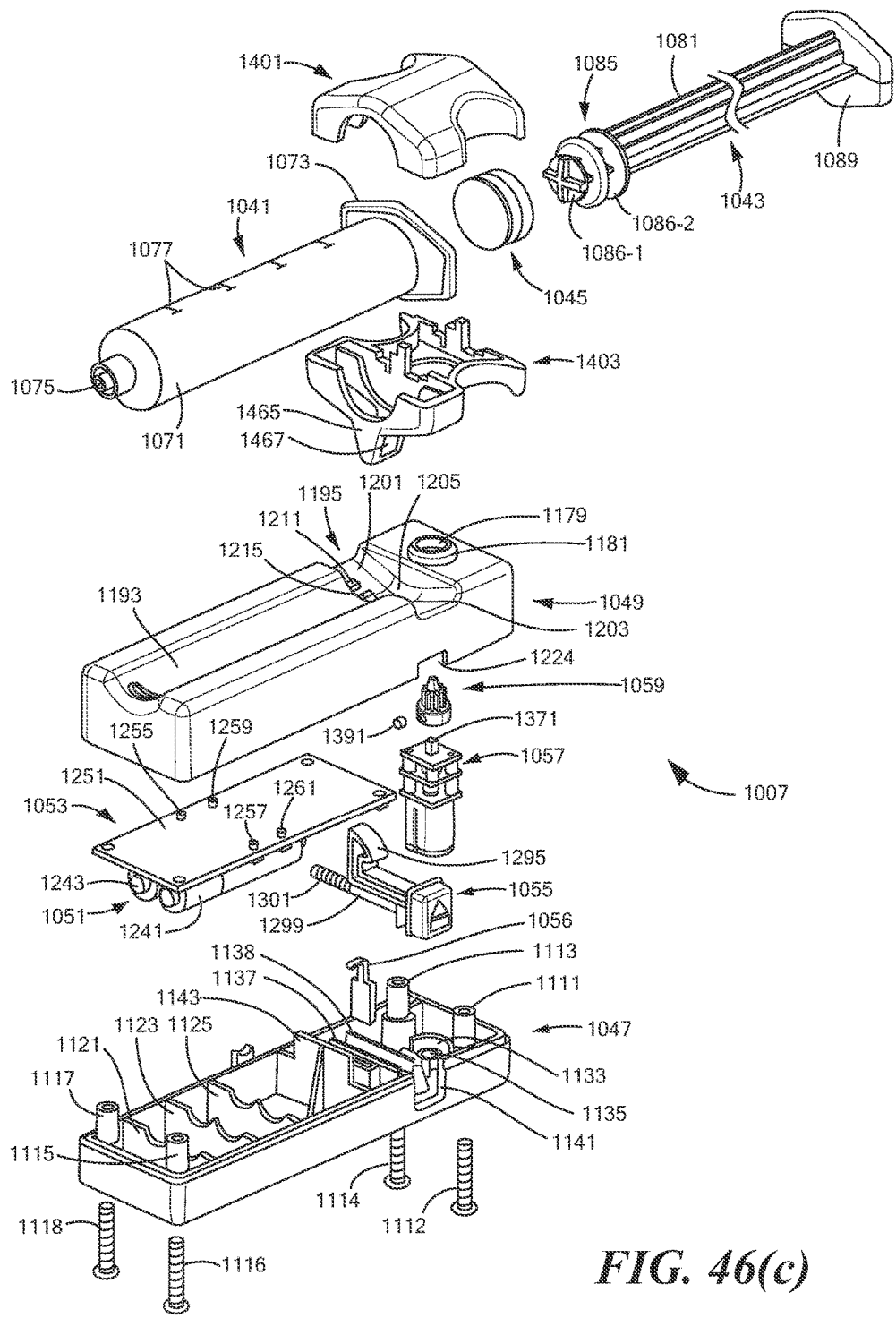
FIG. 46(c) is a partly exploded perspective view of the syringe/pump assembly of FIG. 45.

Syringe/pump assembly 1007, which is also shown separately in FIGS. 46(*a*) through 46(*c*), may comprise a syringe 1031, a pump 1033, and an adaptor 1034. Each of the foregoing components will now be discussed in further detail.

Syringe 1031 may be used to hold a quantity of a fluid, such as a medication (e.g., anesthesia) to be administered to a patient or may be used to hold a quantity of a fluid that has been aspirated from the patient. Syringe 1031 may comprise a syringe body 1041, a syringe plunger 1043 and a seal 1045.

Syringe body 1041, which may be similar to syringe body 141, may comprise a unitary tubular member shaped to define a generally cylindrical main portion 1071 having a flange 1073 disposed at a proximal end thereof and having a male luer connector 1075 disposed at a distal end thereof. Male luer connector 1075 may be appropriately constructed to mate with a female luer connector (not shown) on the proximal end of a length of tubing 1035 that may be used to fluidly interconnect syringe body 1041 and infusion needle assembly 1003. Markings 1077 may be provided on main portion 1071 of syringe body 1041 to indicate the volume of fluid present within syringe body 1041. In the embodiment shown, syringe body 1041 may be dimensioned to hold approximately 20 ml of fluid; however, syringe body 1041 need not be so dimensioned and may be dimensioned to hold greater than 20 ml of fluid (e.g., up to 60 ml or more) or less than 20 ml of fluid (e.g., down to 10 ml or leas). Syringe body 1041 may be molded or otherwise fashioned from a rigid, transparent, medical-grade polymer or similar material.

Figure 47:
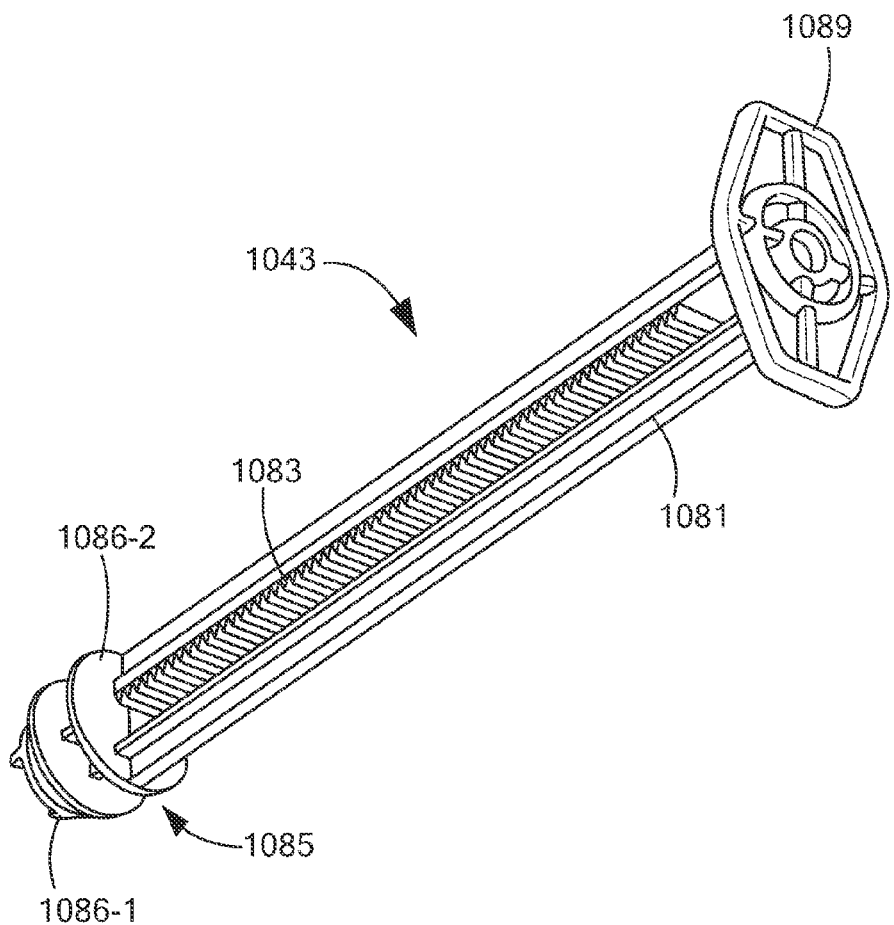
FIG. 47 is a perspective view of the syringe plunger shown in FIG. 45.
Figure 48A:
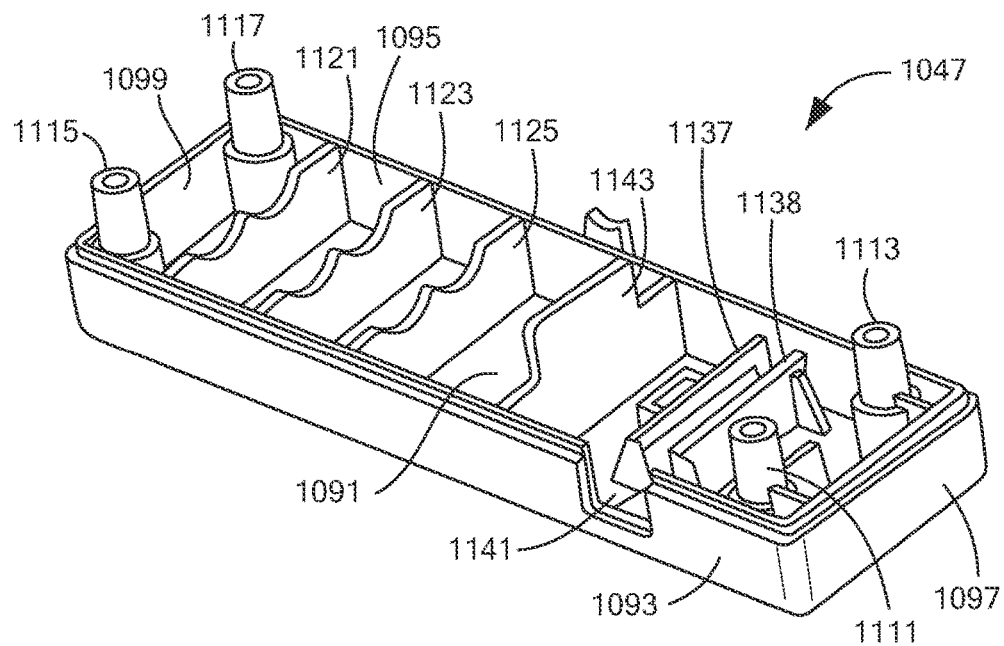
FIGS. 48(a) through 48(e) are top perspective, bottom perspective, top, bottom, and longitudinal section views, respectively, of the pump housing body shown in FIG. 45.
Figure 48B:
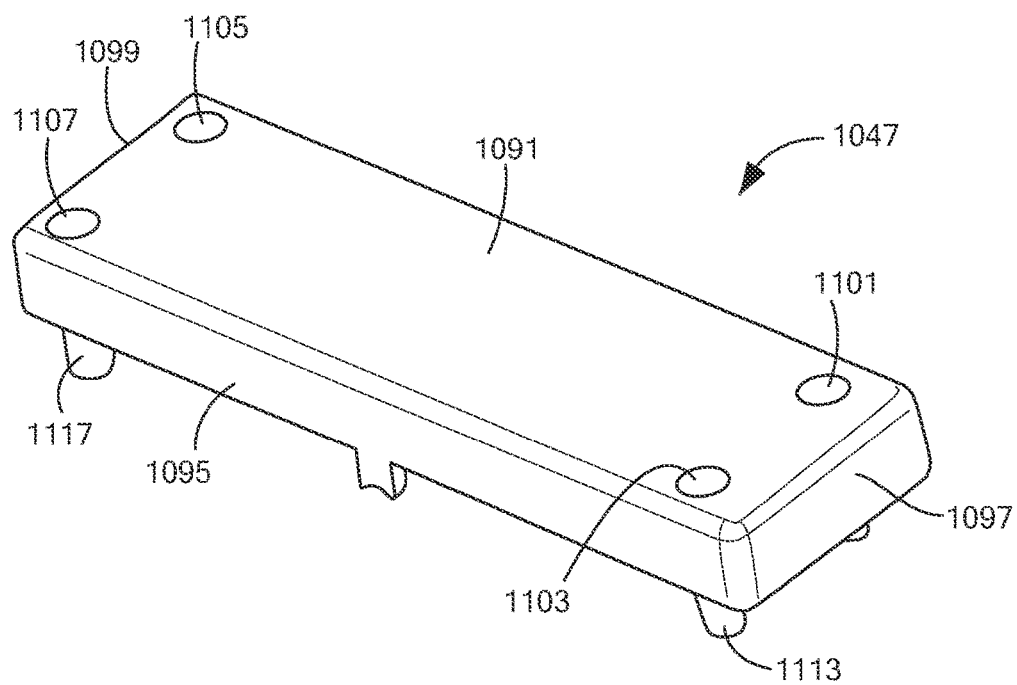
Figure 48C:
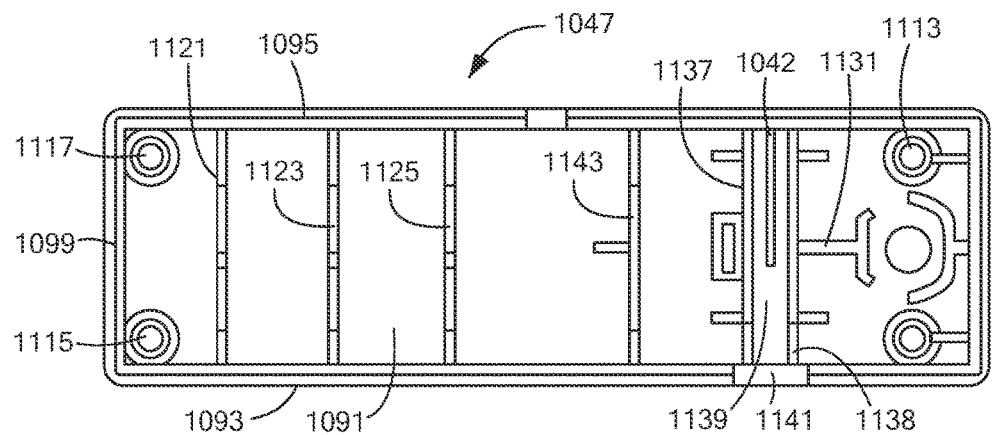
Figure 48D:
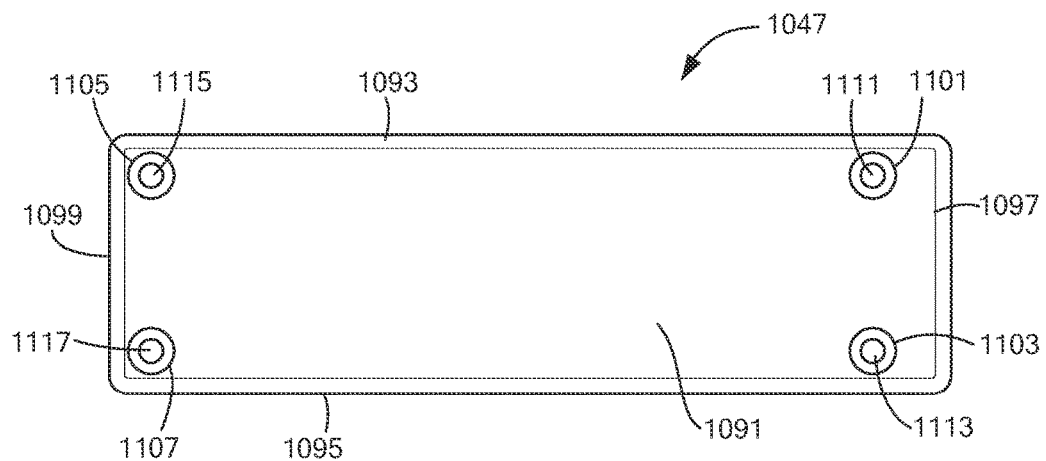
Figure 48E:
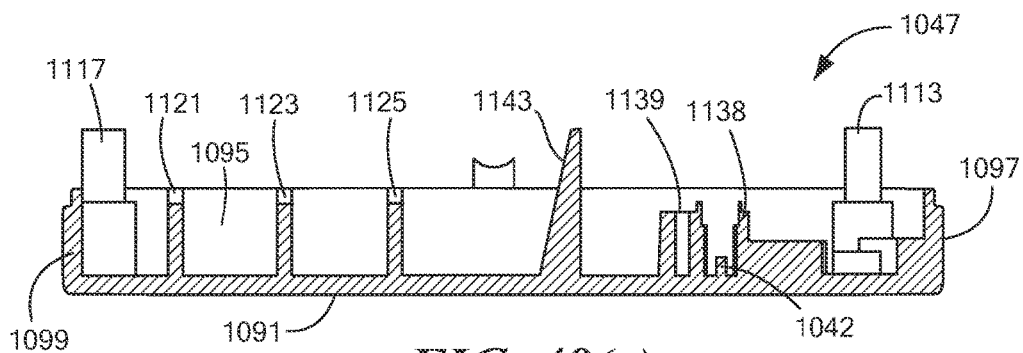
Figure 49A:
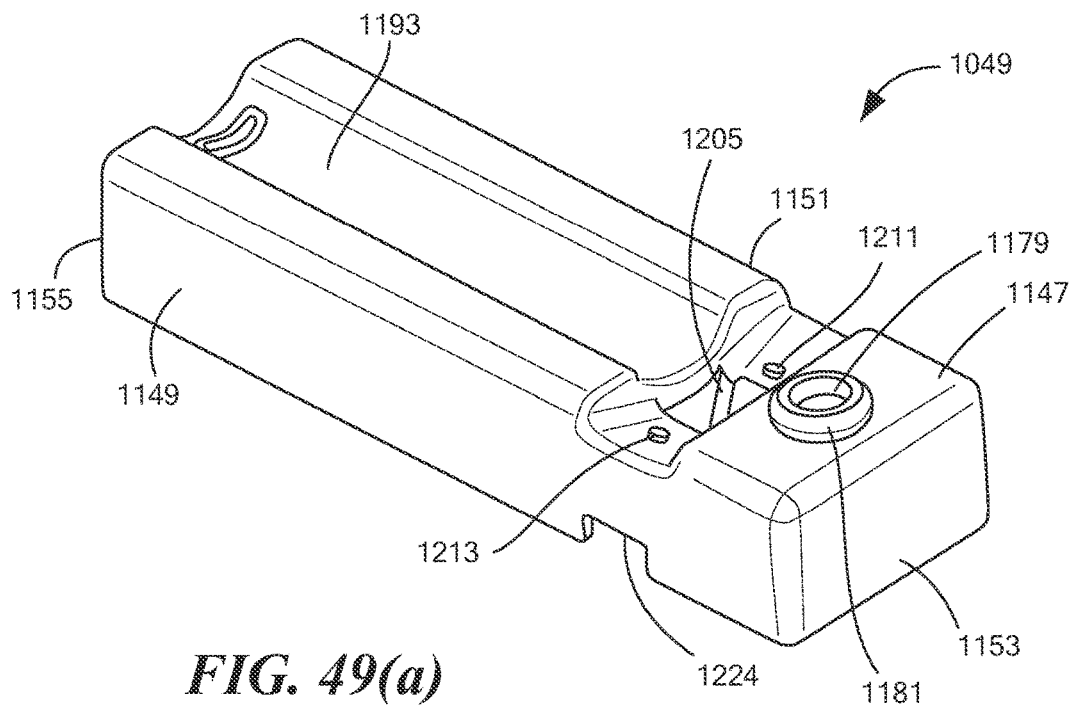
FIGS. 49(a) through 49(e) are top perspective, bottom perspective, top, bottom, and longitudinal section views, respectively, of the pump housing cover shown in FIG. 45.
Figure 49B:
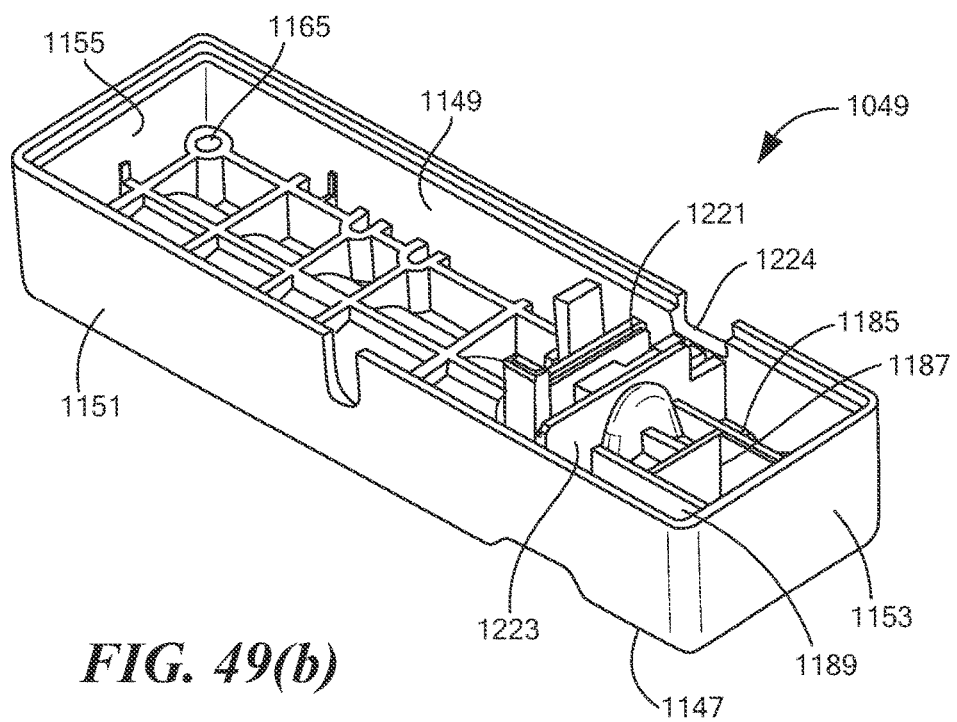
Figure 49C:
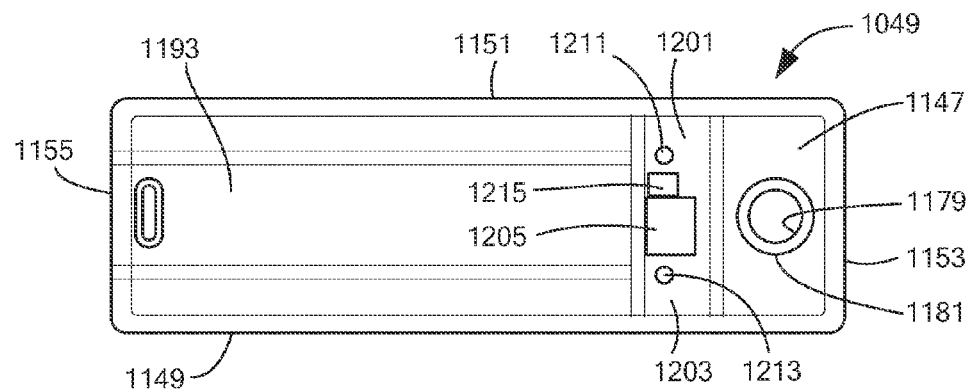
Figure 49D:
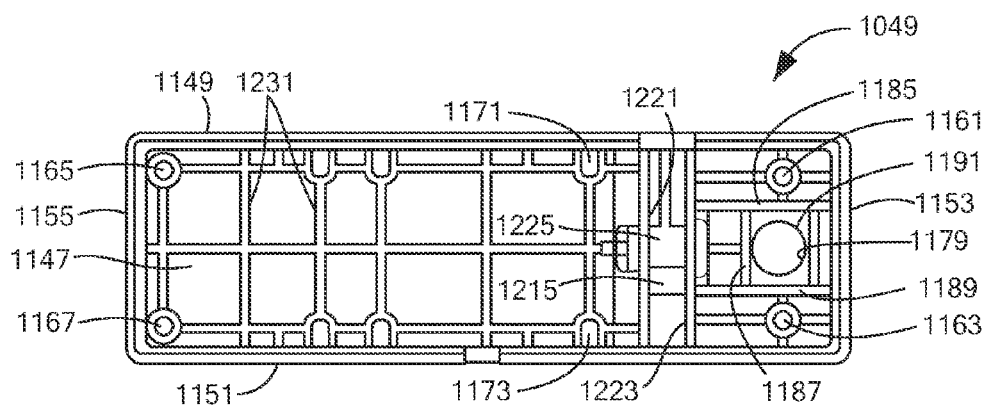
Figure 49E:
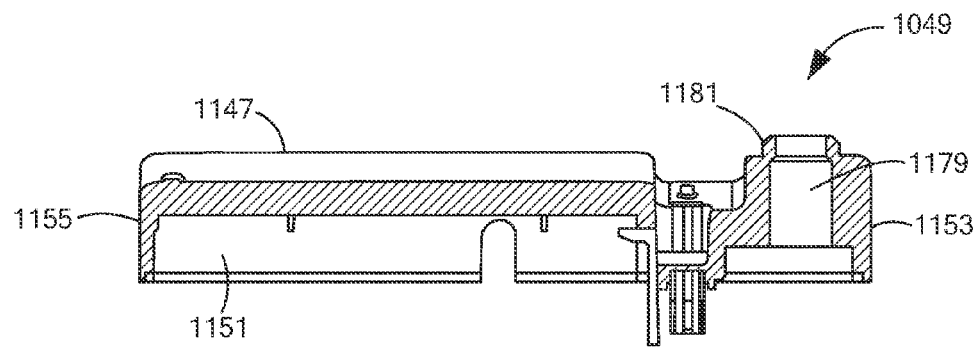

Syringe plunger 1043, which is also shown separately in FIG. 47 and which may be similar to syringe plunger 143, may comprise an elongated unitary member, which may be molded or otherwise fashioned from a rigid, medical-grade polymer or similar material. Syringe plunger 1043 may be shaped to include a column portion 1081 that is generally semi-annular in transverse cross-section. A rack 1083, whose purpose will become apparent below, may be formed on an interior surface of column portion 1081 along at least a portion of the length of column portion 1081. An end member, end cap or collar 1085 may be provided at the distal end of column portion 1081. A distal end 1086-1 of end member 1085 may be adapted to receive seal 1045 thereover. A proximal end 1086-2 of end member 1085 may be adapted to engage a circumferential rib (not shown) on the interior of syringe body 1041 to delimit proximal movement of syringe plunger 1043 relative to syringe body 1041. A handle 1089 may be provided at the proximal end of column portion 1081.

Seal 1045, which may be similar to seal 145, may be conventional. As noted above, seal 1045 may be mounted on the distal end 1086-1 of syringe plunger 1043 and may be appropriately dimensioned to provide a fluid-tight seal between syringe body 1041 and syringe plunger 1043.

Pump 1033, which may be used to expel fluid from syringe 1031 or to draw fluid into syringe 1031 by appropriately driving translational movement of syringe plunger 1043 relative to syringe body 1041, may comprise a housing body 1047, a housing cover 1049, a power source 1051, a control device 1053, a locking clip 1055, a motor 1057, and a gear 1059. Each of the foregoing components will now be discussed further below.

Housing body 1047, which is also shown separately in FIGS. 48(*a*) through 48(*e*) may be a unitary structure molded or otherwise fashioned from a suitably strong material, such as a suitable polymer, metal or other material. Housing body 1047, which may take the form of a generally rectangular trough, may be shaped to include a bottom wall 1091, a first side wall 1093, a second side wall 1095, a first end wall 1097, a second end wall 1099, and an open top. A plurality of wall, embossments and other structural features may extend upwardly from or otherwise be provided in bottom wall 1091 of housing body 1047. As an example of one such feature, a plurality of transverse openings 1101, 1103, 1105, and 1107 may be provided in bottom wall 1091 proximate to its four corners. As an example of another such feature, a plurality of hollow posts 1111, 1113, 1115, and 1117, which hollow posts may be aligned with transverse openings 1101, 1103, 1105, and 1107, respectively, may extend upwardly from bottom wall 1091. Hollow posts 1111, 1113, 1115, and 1117 may be used to receive screws 1112, 1114, 1116, and 1118, respectively, for use in coupling together housing body 1047 and housing cover 1049. As an example of another such feature, a plurality of walls 1121, 1123, and 1125 may extend upwardly from bottom wall 1091 and may extend between first side wall 1093 and second side wall 1095. The top surfaces of walls 1121, 1123, and 1125 may be appropriately shaped to receive a pair of batteries laid thereacross.

As an example of another such feature, a plurality of bosses 1131, 1133 and 1135 may extend upwardly from bottom wall 1091 and may be appropriately arranged to receive the bottom end of motor 1057. As an example of another such feature, a pair of walls 1137 and 1138 may extend upwardly from bottom wall 1091 proximate to a recess 1141 formed in first side wall 1093. Walls 1137 and 1138 may jointly define a space 1139 that may be used to slidably receive a portion of locking clip 1055. Wall 1137 may also be slotted to receive a portion of a detent clip 1056 used to support control device 1053. As an example of another such feature, an embossment 1042 extending upwardly from bottom wall 1091 may be positioned in space 1139 for use in engaging a spring used to bias locking clip 1055. As an example of another such feature, a wall 1143 may extend upwardly from bottom wall 1091 and may extend between first side wall 1093 and second side wall 1095. Wall 1143 may be appropriately dimensioned so that its top surface may provide mechanical support to a circuit board of control device 1053 seated thereon.

Housing cover 1049, which is also shown separately in FIGS. 49(*a*) through 49(*e*), may be a unitary structure molded or otherwise fashioned from a suitably strong material, such as a suitable polymer, metal or other material. Housing cover 1049, which may take the form of a generally rectangular inverted trough, may be shaped to include a top wall 1147, a first side wall 1149, a second side wall 1151, a first end wall 1153, a second end wall 1155, and an open bottom. Housing cover 1049 may be appropriately dimensioned relative to housing body 1047 so that housing cover 1040 may be secured to housing body 1047 to jointly define a cavity for receiving one or more components of pump 1033. A plurality of walls, embossments and other structural features may extend from or otherwise be provided in top wall 1147 of housing cover 1049. As an example of one such feature, a plurality of hollow posts 1161, 1163, 1165, and 1167 may extend downwardly from top wall 1147 and may be positioned so that screws 1112, 1114, 1116, and 1118 inserted through hollow posts 1111, 1113, 1115, and 1117 of housing body 1047 may be received therein, whereby housing cover 1049 and housing body 1047 may be joined together. Hollow posts 1161, 1163, 1165, and 1167 may be internally threaded to receive screws 1112, 1114, 1116 and 1118 or may have mounted therewithin internally threaded sleeves (not shown) that may threadingly engage screws 1112, 1114, 1116, and 1118.

As an example of another such feature, a plurality of hollow posts 1171 and 1173 may extend downwardly from top wall 1147 end may be positioned so that screws (not shown) inserted through a circuit board of control device 1053 may be received therein, whereby the circuit board may be coupled to housing cover 1049. Hollow posts 1171 and 1173 may be internally threaded to receive such screws or may have mounted therewithin internally threaded sleeves (not shown) that may threadingly engage such screws. As an example of another such feature, a transverse opening 1179 may be provided in top wall 1147 of housing body 1047, and a collar 1181 surrounding transverse opening 1179 may extend upwardly a short distance from top wall 1147. Transverse opening 1179 and collar 1181 may be appropriately dimensioned for gear 1059 to extend upwardly therethrough. As an example of another such feature, a plurality of walls 1185, 1187, 1189, and 1191 may extend downwardly trout top wall 1147 and may be appropriately arranged to collectively define a compartment in which a portion of motor 1057 may be received.

As an example of another such feature, top wall 1147 may be shaped to include a first depression 1193 and/or a second depression 1195. First depression 1193 may be appropriately sized and shaped to matingly receive syringe body 1041. Second depression 1195 may be appropriately sized and shaped to matingly receive adaptor 1034. More specifically, second depression 1195 may comprise a first side portion 1201, a second side portion 1203, and a central portion 1205. First side portion 1201 may be sloped downwardly towards central portion 1205 and may be shaped to include an upward projection 1211. Second side portion 1203 may be sloped downwardly towards central portion 1205 and may be shaped to include an upward projection 1213. Central portion 1205 may extend downwardly below first side portion 1201 and second side portion 1203 and may be shaped to include an opening 1215 through which a portion of locking clip 1055 may be removably inserted. A pair of walls 1221 and 1223 may extend downwardly from the underside of top wall 1147 proximate to a recess 1224 formed in first side wall 1149 and may be used to define a space 1225 that may slidably receive a portion of locking clip 1055. Walls 1221 and 1223 may be stepped or otherwise shaped to delimit the sliding movement of locking clip 1055 in space 1225. As an example of another such feature, one or more ribs 1231 may extend downwardly from top wall 1147 to engage a circuit board of control device 1053.

As an example of another such feature, top wall 1147 may be provided with one or more transverse openings (not shown) that may serve as windows to LEDs or other visual indicators on control device 1053 that system 1001 is being operated in an infusion mode. Additionally or alternatively, top wall 1147 may be provided with one or more transverse openings (not shown) that may serve as windows to LEDs or other visual indicators on control device 1053 that system 1001 is being operated in an aspiration mode. As can be appreciated, instead of providing transverse openings in top wall 1147 to serve as windows, housing cover 1049 may be made of a transparent or translucent material.

Power source 1051 may comprise one or more conventional batteries and, more specifically, may comprise one or more conventional disposable AAA batteries. Although power source 1051 is shown in the present embodiment as consisting of two batteries 1241 and 1243, power source 1051 could have as few as one battery or as many as three or more batteries.

Control device 1053 may be in the form of a printed circuit board 1251 that may be coupled to the underside of housing cover 1049 in the manner discussed above. Printed circuit board 1251 may be configured to control the actuation of motor 1057 based on the actuation of foot pedal assembly 1009. Printed circuit board 1251 may additionally be configured in any of the manners disclosed herein to cause motor 1057 to stop, even if foot pedal assembly 1009 is being actuated, when the fluid pressure within the fluid path exceeds a predetermined threshold. For example, printed circuit board 1251 may comprise a current sensing circuit, a resistor and a shut-off switch that are arranged as described above in connection with control device 111' of FIG. 21. Printed circuit board 1251 may additionally be equipped with one or more LEDs 1255 and 1257 or other indicators that may be used to provide visual or other indication that system 1001 is being operated in an infusion mode and/or may be equipped with one or more LEDs 1259 and 1261 or other indicators that may be used to provide visual or other indication that system 1001 is being operated in an aspiration mode. As a means of distinguishing the infusion mode from the aspiration mode, LEDs 1255 and 1257 may emit light of a first color or colors and LEDs 1259 and 1261 may emit light of a second color or colors that are different from the first color or colors. Batteries 1241 and 1243 may be coupled to the underside of printed circuit board 1251 by conventional means, such as a conductive clip, and may be supported by walls 1121, 1123 and 1125 of housing body 1047.

Locking clip 1055, which is also shown separately in FIGS. 50(a) through 50(d), may be a unitary structure molded or otherwise fashioned from a suitably strong material, such as a suitable polymer, metal or other material. Locking clip 1055 may include a block 1271 of generally rectangular shape. Block 1271, in turn, may have a front 1273, a rear 1275, a top 1277, a bottom 1279, a first side 1281, and a second side 1283. Rear 1275 may be slightly enlarged relative to the other surfaces of block 1271 so as to provide a peripheral lip 1285. Locking clip 1055 may additionally include an arm 1291 that may extend rearwardly from rear 1275 of block 1271. A finger 1293 may extend at an angle, for example, generally perpendicularly, from the rear end of arm 1291. Finger 1293 may be bent forwardly to form a pawl 1295. Locking clip 1055 may further include a block 1297 extending rearwardly from rear 1275 and below arm 1291. A post 1299 may extend rearwardly from block 1297 generally parallel to and below arm 1291. Post 1299 may be used to mount a coil spring 1301 coaxially thereover.

Locking clip 1055 may be appropriately dimensioned so that block 1271 may be slidably mounted within an opening formed jointly by recess 1141 of housing body 1047 and recess 1224 of housing cover 1049, with block 1271 being retained within said opening by peripheral lip 1285. Post 1299 of locking clip 1055 may be slidably mounted within space 1139 between walls 1137 and 1138 of housing body 1047 and may be biased in the direction of recesses 1141 and 1224 by coil spring 1301, whose distal end may engage embossment 1042. Arm 1291, finger 1293 and pawl 1295 may be appropriately dimensioned so that, when coil spring 1301 is not being compressed as a result of an operator's depression of block 1271, pawl 1295 may extend sufficiently through opening 1215 in housing cover 1049 to lockably engage a portion of adaptor 1034 sitting in central portion 1205 of second depression 1195 and so that, when coil spring 1301 is sufficiently compressed due to an operator's depression of block 1271, pawl 1295 may be withdrawn sufficiently from opening 1215 so as not to engage adaptor 1034, thereby enabling adaptor 1034 to be withdrawn from pump 1033.

Motor 1057, which may be, for example, a conventional bi-directional DC motor, may be electrically coupled to control device 1053 by wires (not shown) or other suitable means. Motor 1057 may comprise a rotatable shaft 1371, which may be generally D-shaped in transverse cross-section. Motor 1057 may be appropriately dimensioned to be securely received by bosses 1131, 1133 and 1135 of housing body 1047 and by walls 1185, 1187, 1189 and 1191 of housing cover 1049.

Figure 51A:
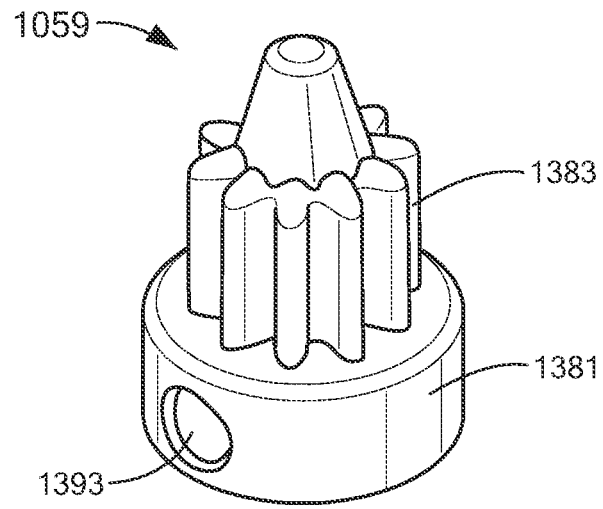
FIGS. 51(a) and 51(b) are top perspective and bottom perspective views, respectively, of the gear shown in 46(c)
Figure 51B:
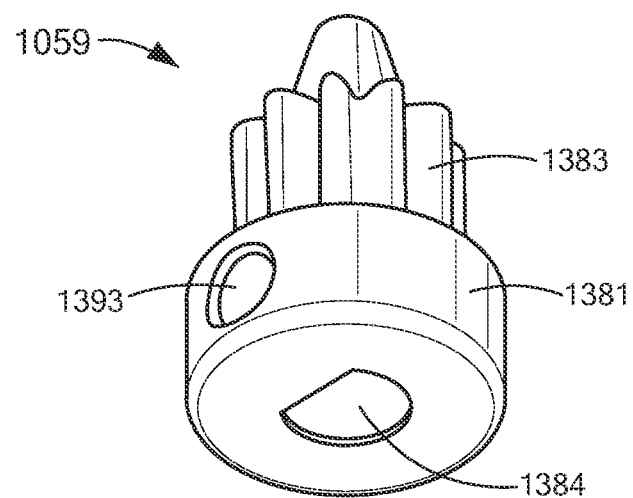

Gear 1059, which is also shown separately in FIGS. 51(a) and 51(b), may be a unitary structure molded or otherwise fashioned from a suitably strong material, such as a suitable polymer, metal or other material. Gear 1059 may be appropriately shaped to include a base portion 1381 and a toothed wheel 1383. Base portion 1381 may include a longitudinally extending bore 1384, which may be appropriately dimensioned to receive rotatable shall 1371 so that gear 1059 may be coupled to shaft 1371 for rotation. Gear 1059 may be fixed to shaft 1371 by means of a hex socket 1391 inserted into a hole 1393 in base portion 1381. Toothed wheel 1383 may be appropriately dimensioned so that, when syringe 1031 is coupled to pump 1033, gear 1059 is brought into engagement with rack 1083 of syringe plunger 1043, and the rotation of gear 1059 causes syringe plunger 1043 to be moved translationally relative to syringe body 1041, resulting either in the expulsion of fluid from syringe body 1041 or in the suctioning of fluid into syringe body 1041, depending on the direction in which syringe plunger 1043 is moved.

Pump 1033 may additionally include a power on/off switch (not shown).

Figure 52A:
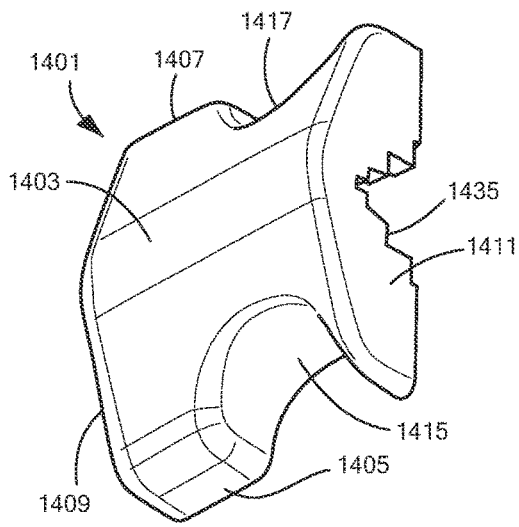
FIGS. 52(a) through 52(c) are top perspective, bottom perspective, and bottom views, respectively, of the top portion of the adaptor shown in FIG. 45.
Figure 52B:
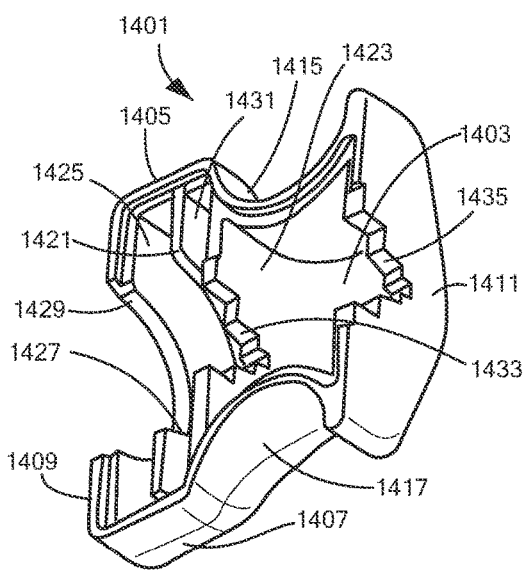
Figure 52C:
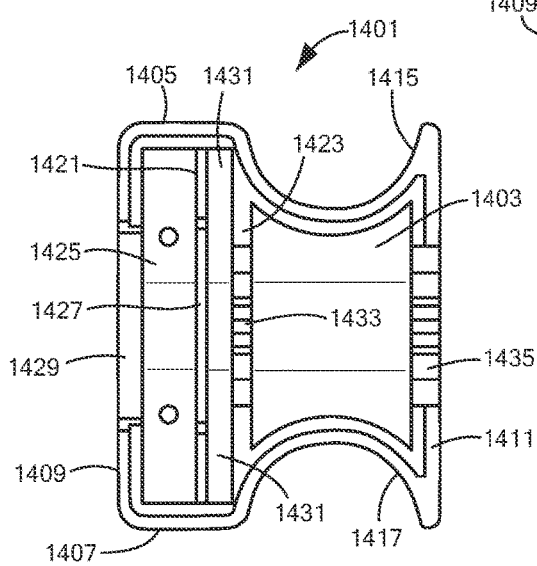

Adaptor 1034, which may be fixedly and coaxially mounted on syringe 1031 and which may be used to mechanically couple/decouple syringe 1031 to/from pump 1033, may comprise a top portion 1401 and a bottom portion 1403. Top portion 1401 and bottom portion 1403 may be complementarily shaped and may be joined to one another by adhesive, welding, mechanical means, or other suitable means. Top portion 1401, which is also shown separately in FIGS. 52(a) through 52(c), may be a unitary structure molded or otherwise fashioned from a suitably strong material, such as a suitable polymer, metal or other material. Top portion 1401 may be shaped to include a top wall 1403, a first side wall 1405, a second side wall 1407, a first end wall 1409, a second end wall 1411, and an open bottom. Top wall 1403 may be shaped to conform to the shape of syringe flange 1073. First side wall 1405 may include a recess 1415 that may be shaped to receive a first finger of an operator for use to handling adaptor 1034, and second side wall 1407 may include a recess 1417 that may be shaped so receive a second finger of an operator for use in handling adaptor 1034. A plurality of internal walls 1421 and 1423 may extend downwardly from top wall 1403 and may extend from first side wall 1405 to second side wall 1407. Internal wall 1421 may run parallel to first end wall 1409 and may define a first compartment 1425 with top wall 1403, first end wall 1409, first side wall 1405 and second side wall 1407. Internal wall 1421 may include a recess 1427, and first end wall 1409 may include a recess 1429. Recesses 1427 and 1429 may be shaped to matingly receive syringe body 1401 thereacross. Internal wall 1423 may ran parallel to internal wall 1421 and may define a second compartment 1431 with top wall 1403, internal wall 1421, first side wall 1405 and second side wall 1407. Second compartment 1431 may be shaped to matingly receive a portion of syringe flange 1073. Internal wall 1423 may include a recess 1433 and second end wall 1411 may include a recess 1435. Recesses 1433 and 1435 may be shaped, to matingly receive syringe plunger 1043 in such a manner that syringe plunger 1043 may be slidably mounted thereacross.

Figure 53A:
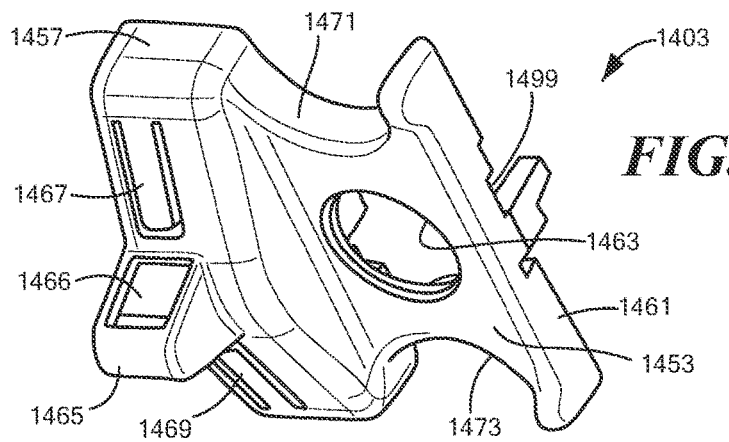
FIGS. 53(a) through 53(c) are bottom perspective, top perspective, and bottom views, respectively, of the bottom portion of the adaptor shown in FIG. 45.
Figure 53B:
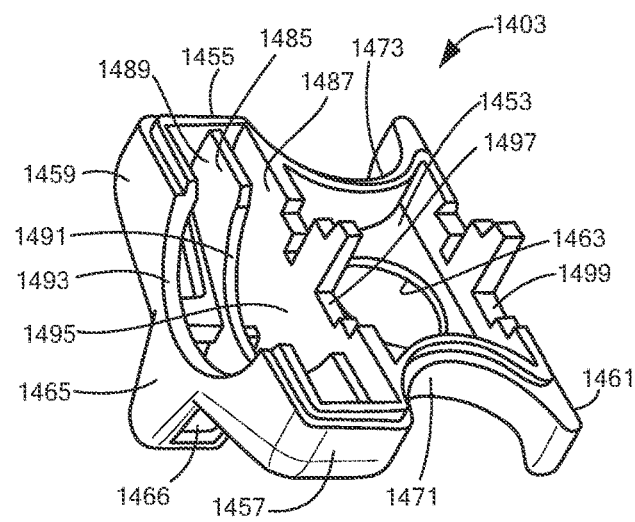
Figure 53C:
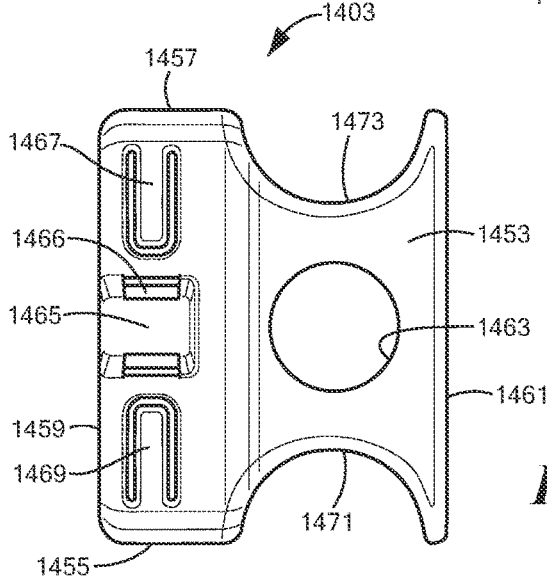

Bottom portion 1403, which is also shown separately in FIGS. 53(a) through 53(c), may be a unitary structure molded or otherwise fashioned from a suitably strong material, such as a suitable polymer, metal or other material. Bottom portion 1403 may be shaped to include a bottom wall 1453, a first side wall 1455, a second side wall 1457, a first end wall 1459, a second end wall 1461, and an open top. Bottom wall 1453 may include a transverse opening 1463 that may be appropriately dimensioned and positioned to permit gear 1059 to pass therethrough so that gear 1059 may engage rack 1083 of syringe plunger 1043. Bottom wall 1453 may additionally include a projection 1465 extending downwardly therefrom. Projection 1465 may be shaped to mate with central portion 1205 of second depression 1195 of housing cover 1049. Moreover, projection 1465 may include an opening 1466 that may mate with pawl 1295 of locking clip 1055 so that adaptor 1034 may be lockingly mounted on pump 1033. Bottom wall 1453 may further include a pair of hingedly mounted spring tabs 1467 and 1469. Spring tabs 1467 and 1469 may be appropriately shaped to mate with first side portion 1201 and second side portion 1203, respectively, of housing cover 1049 and to resiliently engage projections 1211 and 1213, respectively.

First side wall 1455 of bottom portion 1403 may include a recess 1471 that may be aligned with recess 1415 of top portion 1401 to receive a first finger of an operator for use in handling adaptor 1034, and second side wall 1457 may include a recess 1473 that may be aligned with recess 1417 of top portion 1401 to receive a second finger of an operator for use in handling adaptor 1034. A plurality of internal walls 1485 and 1487 may extend upwardly from bottom wall 1453 and may extend from first side wall 1455 to second side wall 1457. Internal wall 1485 may run parallel to first end wall 1459 and may define a first compartment 1489 with bottom wall 1453, first end wall 1459, first side wall 1455 and second side wall 1457. Internal wall 1485 may include a recess 1491, and first end wall 1459 may include a recess 1493. Recesses 1491 and 1493 may be shaped to matingly receive syringe body 1401 thereacross. Internal wall 1487 may run parallel to internal wall 1485 and may define a second compartment 1495 with bottom wall 1453, internal wall 1485, first side wall 1455 and second side wall 1457. Second compartment 1495 may be shaped to matingly receive a portion of syringe flange 1073. Internal wall 1487 may include a recess 1497 and second end wall 1461 may include a recess 1499. Recesses 1497 and 1499 may be shaped to matingly receive syringe plunger 1043 in such a manner that syringe plunger 1043 may be slidably mounted thereacross.

Foot pedal assembly 1009, which is also shown separately in FIGS. 54(a) and 54(b), may comprise a printed circuit board 1501, a plurality of resiliently-compressible tubes 1503-1 and 1503-2, a plurality of plugs 1505-1 and 1505-2, and an electrical cable 1507. Each of the foregoing components will now be discussed further below.

Printed circuit board 1501 may comprise a circuit board 1511. Circuit board 1511, in turn, may be an elongated member having a first portion 1513 and a second portion

1515. Circuit board 1511 may be sufficiently flexible to enable first portion 1513 to be flexed towards second portion 1515 or vice versa. Due or more pressure-actuated switches 1517 may be mounted on first portion 1513, and one or more pressure-actuated switches 1519 may be mounted on second portion 1515. Switches 1517 and 1519 may be configured so that actuation of at least one of switches 1517 may cause pump 1033 to be operated in an infusion mode, and actuation of at least one of switches 1519 may cause pump 1033 to be operated in an aspiration mode, or vice versa.

Resiliently-compressible tubes 1503-1 and 1503-2 may be resilient members molded or otherwise fashioned from blown polyethylene or a similarly suitable material that quickly returns to its original shape after being radially compressed. Tube 1503-1 may be appropriately dimensioned to receive first portion 1513 of circuit board 1501, and tube 1503-2 may be appropriately dimensioned to receive second portion 1515 of circuit board 1502. Preferably, tubes 1503-1 and 1503-2 are slightly undersized relative to printed circuit board 1501 so that, when printed circuit board 1501 is inserted thereinto, tubes 1503-1 and 1503-2 become slightly distended by printed circuit board 1501. In this manner, regardless of the at-rest rotational position of tubes 1503-1 and 1503-2 on a floor or similar surface, when an operator steps on tube 1503-1 or tube 1503-2, the stepping of the operator's foot on the applicable tube rapidly ensures a suitable orientation of printed circuit board 1501 for actuation of the desired pressure-actuated switches. Tubes 1503-1 and 1503-2 may be generally identical to one another in size, shape, construction, and appearance or may be marked and/or colored differently to denote the different effects resulting from their being depressed, for example, infusion or aspiration. As can be appreciated, although tubes 1503-1 and 1503 are shown in the present embodiment as directly contacting one another in an end-to-end arrangement, tubes 1503-1 and 1503-2 may be spaced apart from one another, for example, using a suitable tubular member. In addition, it should be appreciated that tubes 1503-1 and 1503-2 may be replaced with a single tube having a length equal to the combined lengths of tubes 1503-1 and 1503-2.

Plug 1505-1, which may be used to plug the outside end of tube 1503-1, may be mounted in tube 1503-1 with an interference fit and an adhesive. Plug 1505-2, which may be used to plug the outside end of tube 1503-2, may be mounted in tube 1503-2 with an interference fit and an adhesive. Plug 1505-1 may be shaped to include a longitudinal bore 1521, through which a first end 1523 of cable 1507 may be inserted. First end 1523 of cable 1507 may be coupled to printed circuit board 1501 and may be secured thereto using a cable tie 1525. A second end 1526 of cable 1523 may be provided with an audio plug 1527, which may be removably coupled to a plug receptacle 1528 mounted on printed circuit board 1251 in pump 1033 and accessible through an opening 1529 of housing cover 1049.

To prepare system 1001 for the injection of fluid into a patient, syringe/pump 1007 may first be prepped. This may be done, preferably while the combination of syringe 1031 and adaptor 1034 is decoupled from pump 1033, by manna by refracting syringe plunger 1043 within syringe body 1041 while male luer connector 1075 or a fluid conducting member attached thereto is inserted into the desired fluid. The combination of syringe 1031 and adaptor 1034 may then be coupled to pump 1033 first by aligning-adaptor 1034 with pump 1033 so that opening 1463 of adaptor 1034 is positioned over gear 1059 of pump 1033 and so that projection 1495 of adaptor 1034 is positioned over central portion 1205 of second depression 1195 of pump 1033. Next, adaptor 1034 may be brought into locking engagement with pump 1033 by inserting projection 1465 of adaptor 1034 down into central portion 1205 of second depression 1195 until pawl 1295 of locking clip 1055 snaps-locks into opening 1466 of projection 1465. The aforementioned snap-locking together of adaptor 1034 and pump 1033 is accompanied by the engagement of gear 1059, which is inserted through opening 1463 of adaptor 1034, with rack 1083 of plunger 1043. With syringe/pump 1007 thus prepped, infusion needle assembly 1003 may be fluidly coupled to syringe body 1041 if it has not already been so coupled. Infusion needle 1017 may then be inserted into the patient at a desired location. To dispense fluid from syringe 1031 into the patient, the operator steps onto tube 1503-1 to actuate at least one of switches 1517 positioned therewithin (or, if tube 1503-1 is configured for aspiration and tube 1503-2 is configured for infusion, the operator steps on tube 1503-2 to depress at least one of switches 1519 positioned therewithin). The actuation of at least one of switches 1517 causes LEDs 1255 and 1257 to emit light and simultaneously causes motor 1057 to drive the rotation of gear 1059 against rack 1083 such that plunger 1043 causes the dispensing of fluid from syringe 1031. To aspirate fluid from the patient, the operator steps onto tube 1503-2 to actuate at least one of switches 1519 positioned therewithin (or, if tube 1503-1 is configured for aspiration and tube 1503-2 is configured for infusion, the operator steps on tube 1503-1 to depress at least one of switches 1517 positioned therewithin). The actuation of at least one of switches 1519 causes LEDs 1259 and 1261 to emit light and simultaneously causes motor 1057 to drive the rotation of gear 1059 against rack 1083 such that plunger 1043 causes fluid to be drawn into syringe 1031. If, at any time during which at least one switch 1517 or at least one switch 1519 is actuated, the pressure in the fluid path exceeds the predetermined threshold, control device 1053 automatically stops the operation of motor 1057.

To remove the combination of syringe 1031 and adaptor 1034 from pump 1033, one may slide block 1271 of locking clip 1055 sufficiently towards the interior of pump 1033 so that pawl 1295 of locking clip 1055 is withdrawn from opening 1466 of projection 1465 and, at the same time, may lift the combination of syringe 1031 and adaptor 1034 away from pump 1033.

If desired, one or more components of system 1001 and, in fact, preferably all of the components of system 1001, except possibly for handheld ultrasound imager 1005 and pump 1033, may be disposable, single-use items.

As noted above, control device 1053 may be in the form of a control circuit that senses the motor current using a series resistor, such as a 1 ohm series resistor. The sensed motor current is then used as a proxy for the fluid pressure in the syringe chamber. This pressure is a direct result of the driving force of the plunger and is determined by the gear, the rack and the torque of the motor. The torque performance of the motor is fairly linear with the current drawn by the motor. The correspondence of motor current to the resultant syringe pressure is sufficient to determine the infusion pressure during procedures like anesthesia infusion procedures. By limiting the operation of the motor to an acceptable current range, an acceptable range of infusion pressure can be maintained.

An alternative to the foregoing arrangement is to measure the pressure in the syringe chamber directly by modifying the seal and the end cap design of the syringe plunger. More specifically, a space can be designed between the seal and the end cap such that the gap distance between the proximal surface of the seal and the distal surface of the plunger end cap is known when the syringe is empty and without fluid. When the syringe contains fluid, the syringe can be operated so that the chamber fluid pressure is above atmospheric. In response to the increased syringe fluid pressure on the distal surface of the seal, the shape of the seal changes in such a way as to reduce the gap distance between the seal and the plunger end cap. This change in the gap distance directly correlates with the pressure in the fluid of the syringe.

The aforementioned gap distance may be measured by any of a number of different techniques. To measure the gap distance electrically, two conductive paths may be provided from the seal and the plunger to run along the full length of the plunger to the syringe collar with electrically conductive wipers, subsequently terminating at the printed circuit board in the pump housing to control the fluid pressure by shutting off the motor current and torque.

The foregoing gap displacement may be detected as either a binary or continuous analog signal.

Figure 55:
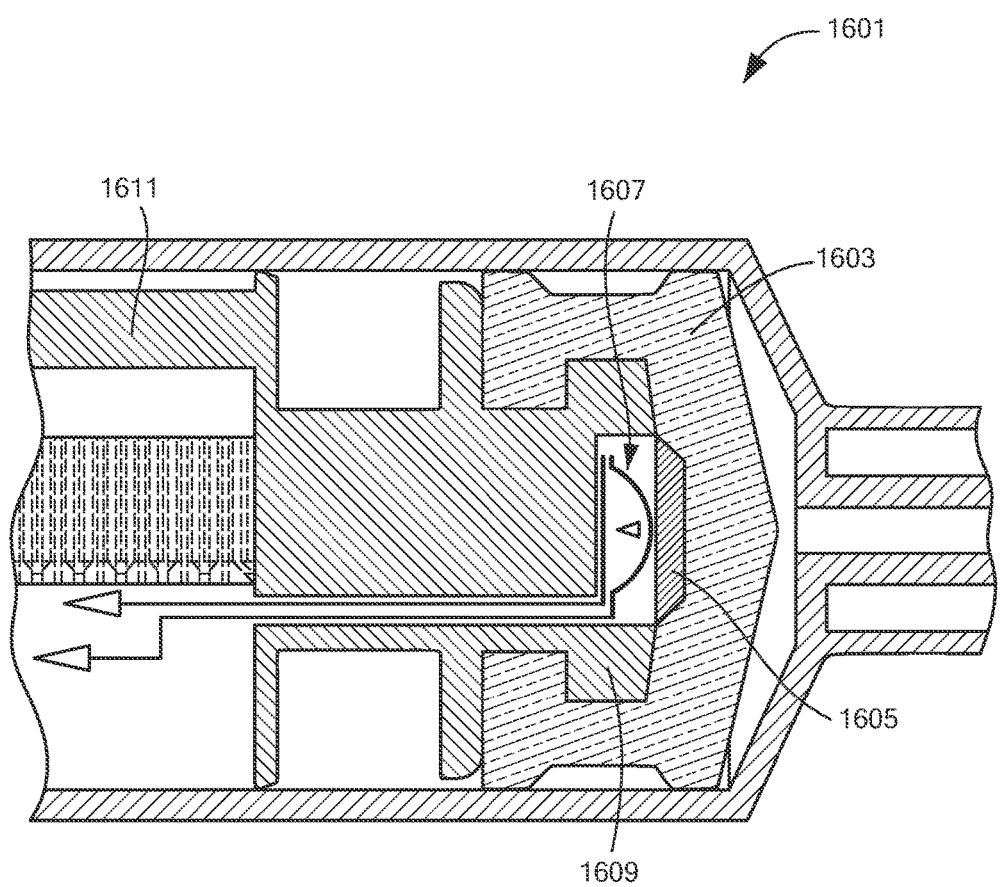
FIG. 55 is a fragmentary, partly schematic, section view of a first alternate syringe for use in the system of FIG. 45, the first alternate syringe comprising a first embodiment of a fluid pressure sensing device.

One example of a binary embodiment tor detecting gap displacement is shown in FIG. 55 as part of syringe 1601. As can be seen in FIG. 55, the proximal surface of a seal 1603 may be provided with a stiff pressure plate 1605 which pushes against a click switch 1607 embedded its a distal end cap 1609 of a plunger 1611. When a threshold occlusion pressure exists and the gap is closed, pressure plate 1605 activates click switch 1607, making an audible sound that indicates to an operator that the threshold pressure has been exceeded.

As another example of a binary embodiment, the proximal surface of the seal may be made of or coated with an electrically conductive material which shorts out contacts embedded in the distal end can of the plunger. When a threshold occlusion pressure exists and the gap is closed, the conductive surface closes the contacts. The closure event is passed along the conductive paths from the plunger to the collar to the printed circuit board, where the control circuitry terminates the motor current and torque.

Figure 56:
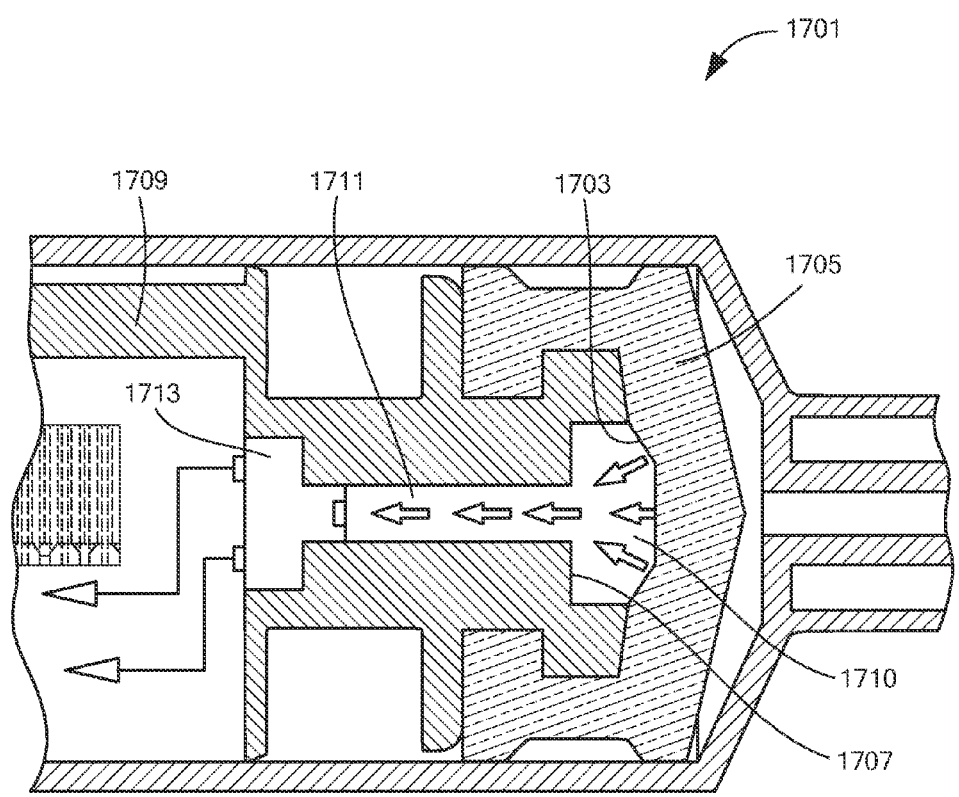
FIG. 56 is a fragmentary, partly schematic, section view of a second alternate syringe tor use in the system of FIG. 45, the second alternate syringe comprising a second embodiment of a fluid pressure sensing device.

One example of an analog embodiment for detecting gap displacement is shown in FIG. 56 as part of syringe 1701. As can be seen in FIG. 56, the proximal surface 1703 of the seal 1705 and the end cap 1707 of the plunger 1709 may provide a sealed pneumatic chamber 1710 for detecting the fluid pressure inside the syringe body. A pneumatic channel 1711 may be created from this sealed chamber and connected to an inexpensive small pneumatic sensor device 1713 mounted on the rails of the plunger 1709. Such pneumatic sensor devices of this type are currently used for consumer blood pressure measurement medical devices. The electrical signals from such a device may be passed along the conductive paths from the plunger to the collar to the printed circuit board, where the electrical signals are converted to pressure to determine whether to terminate the motor current and torque.

Figure 57:
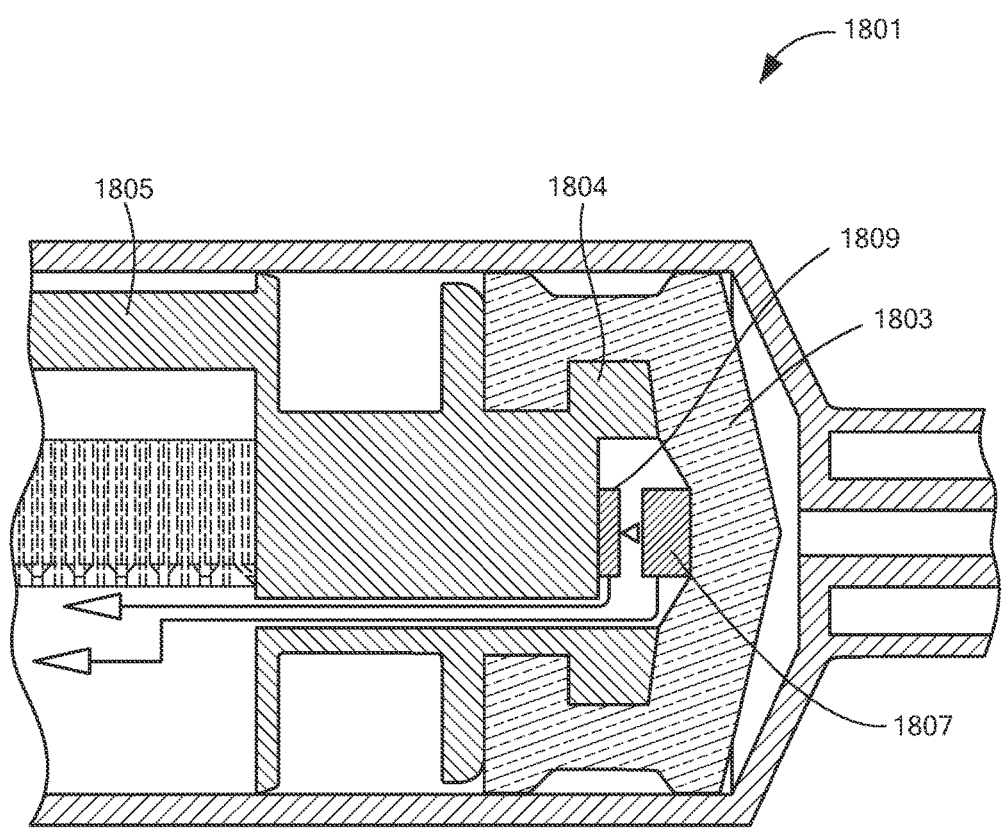
FIG. 57 is a fragmentary, partly schematic, section view of a third alternate syringe for use in the system of FIG. 45, the third alternate syringe comprising a third embodiment of a fluid pressure sensing device.

Another example of an analog embodiment for detecting gap displacement is shown in FIG. 57 as part of syringe 1801. As can be seen in FIG. 57, the proximal surface of the seal 1803 may have an electrically conductive element 1507 mounted thereon, and the end cap 1804 of the plunger 1805 may have an electrically conductive element 1809 mounted thereon. Elements 1807 and 1809 may be used to detect the gap distance either capacitively (i.e., as two parallel electrical plates) or inductively (i.e., as coupling between two parallel coils). The capacitive or inductive electrical signals may be passed along the conductive paths from the plunger to the collar to the printed circuit board, where the capacitive or inductive signals is processed to determine whether to terminate the motor current and torque.

Another example of an analog embodiment for detecting gap displacement has conductive elements that may be resistive, thereby allowing the variation in the contact area of the two surfaces its response to the seal pressure compliance to correspond to the syringe fluid pressure. The surface of the end cap may be flat, and the surface of the seal may be convex with a sphericity proportional to the fluid pressure and compliance on the seal. The resultant resistance between the two surfaces in contact varies in proportion to the fluid pressure. The electrical signals from this resistive sensor may be passed along the conductive paths from the plunger to the collar to the printed circuit board, where the resistance is processed to determine whether to terminate the motor current and torque.

Figure 58A:
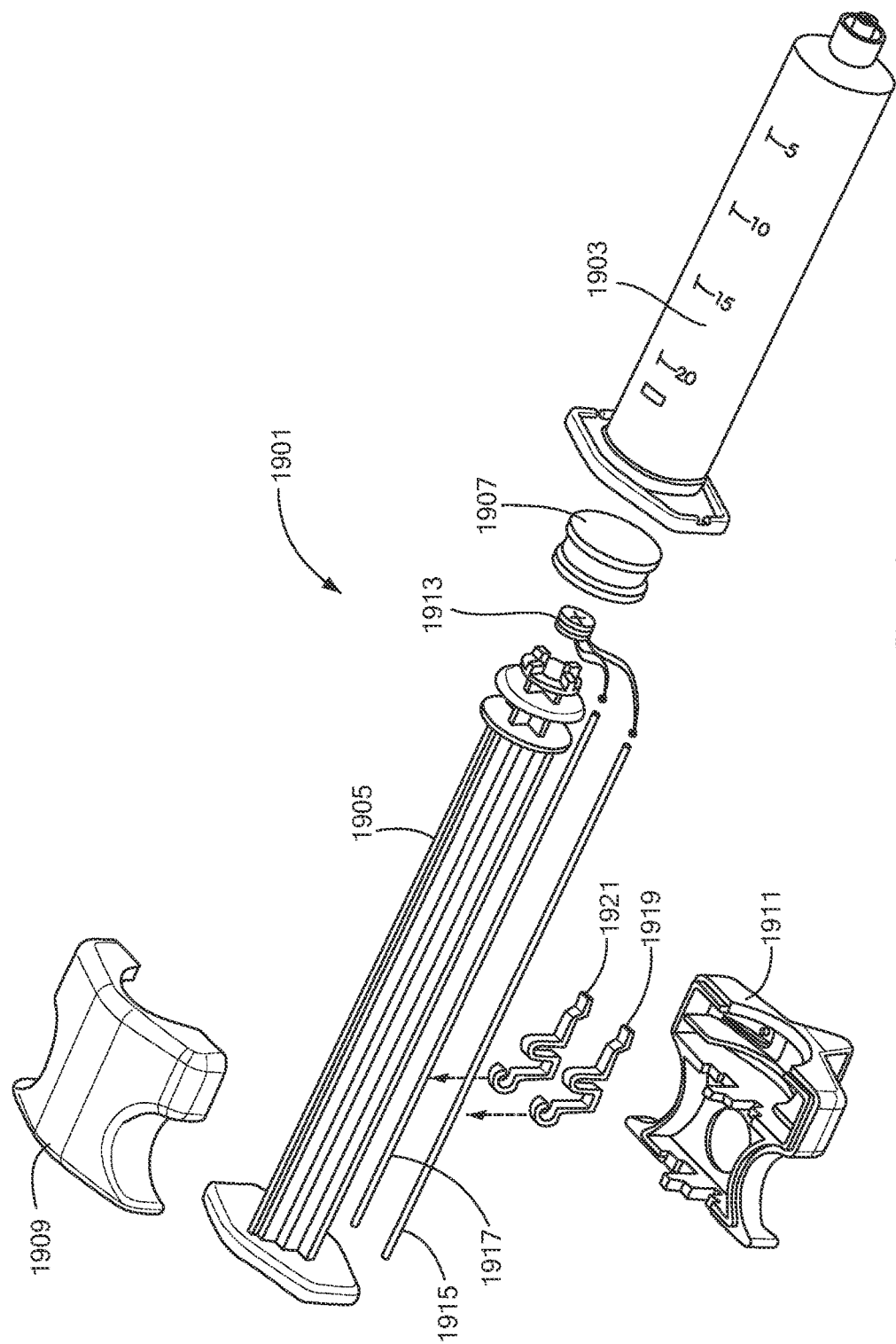
FIGS. 58(a) and 58(b) are exploded perspective and longitudinal section views, respectively, of a fourth alternate syringe for use in the system of FIG. 45, the fourth alternate syringe comprising a fourth embodiment of a fluid pressure sensing device, the syringe being shown in combination with an adaptor.
Figure 58B:
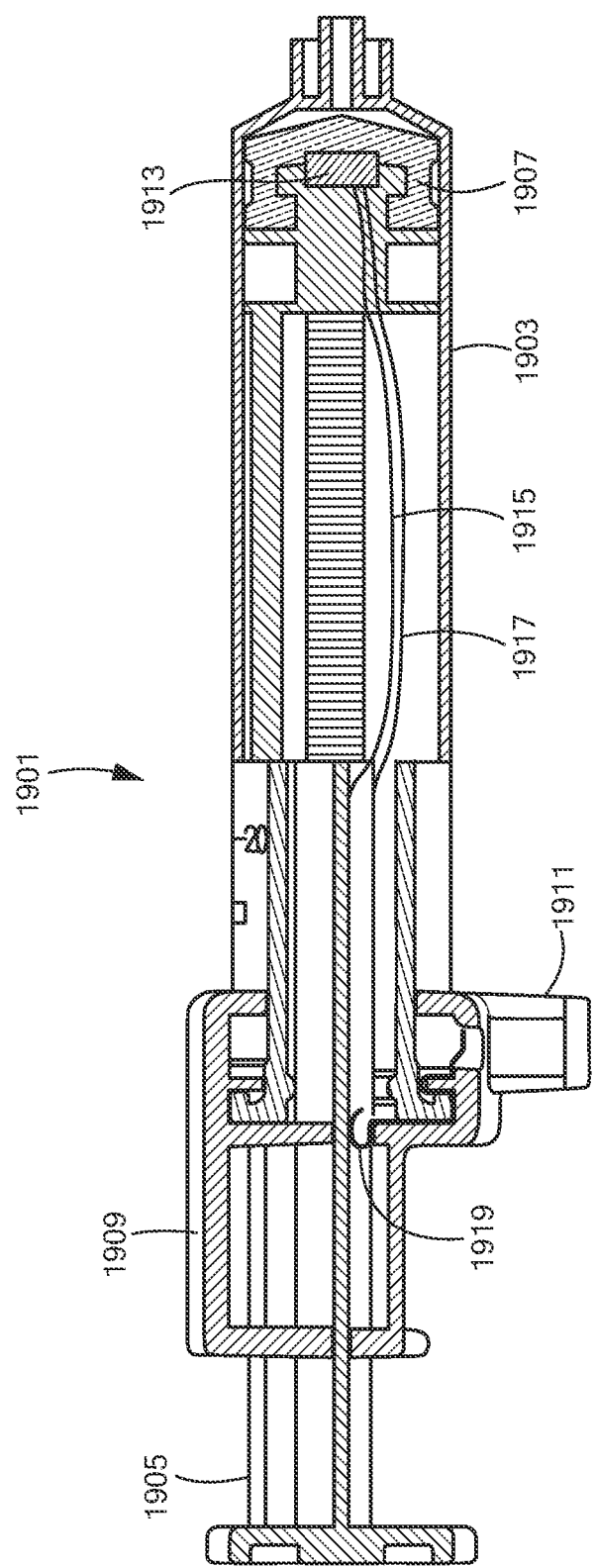

Still another arrangement is shown in FIGS. 58(*a*) and 58(*b*) as syringe 1901. Syringe 1901 may comprise a syringe body 1903, a syringe plunger 1905, a seal 1907, an adaptor top portion 1909, an adaptor bottom portion 1911, a pressure sensing module 1913, bus bars 1915 and 1917, and spring contacts 1919 and 1921.

In the foregoing analog embodiments, continuous variable measurement can also provide additional information about fluid characteristics. Microcomputer software processing could be added so the printed circuit board, allowing real-time data to be generated for an operator, such as flow rates, actual pressure monitoring and fluid injection velocity. Procedure information may also be maintained for patient records.

It should be noted that the present invention is not to be limited to applications involving nerve blocks using regional anesthesia. Rather, the present invention may also be used in joint injections (tendons or muscles), deep vascular access, suction biopsies, aspiration of bodily fluids, intralesional injections for tumor chemotherapy treatments of tumors, and general controlled injection or aspiration of fluids of the human body. The present invention also has applications in dentistry and pediatrics. In dentistry, initial injection pressures of 100 mmHg (2 psi) or less have been found to correlate with less pain and anxiety compared to higher injection pressures (300 mmHg (5 psi) and greater) (see Kudo, "Initial Injection Pressure for Dental Local Anesthesia: Effects on Pain and Anxiety," Anesthesia Progress, 52(3); 95-101 (2005), which is incorporated herein by reference.

It should also be noted that an alternative to the use of a bi-directional drive mechanism in any of the above embodiments is aspiration by means of an evacuated aspiration vial.

The embodiments of the present invention described above are intended to be merely exemplary and those skilled in the art shall be able to make numerous variations and modifications to if without departing from the spirit of the present invention. All such variations and modifications are intended to be within the scope of the present invention as defined in the appended claims.

What is claimed is:

1. A system for controllably administering fluid to a patient and/or for controllably withdrawing fluid from the patient, the system comprising:
   an infusion needle;
   a syringe for holding a quantity of fluid, the syringe being in fluid communication with the infusion needle, the syringe comprising a syringe body and a syringe plunger, the syringe plunger comprising a column portion having a proximal end and a distal end, the syringe plunger further comprising a handle disposed at the proximal end of the column portion, the distal end of the column portion being insertable into the syringe body, the column portion comprising a rack;

a bi-directional pump adapted to be operably coupled to the infusion needle for creating fluid flow through the infusion needle, the bi-directional pump comprising a gear engageable with the rack for driving the rack so as to move the syringe plunger relative to the syringe body in order to alternately produce positive and negative fluid flow in the infusion needle; and a hands-free switch for activating and/or deactivating the bi-directional pump, the hands-free switch comprising a first switch and a second switch, wherein actuation of the first switch causes the bi-directional pump to expel fluid from the syringe body, wherein actuation of the second switch causes the bi-directional pump to draw fluid into the syringe body, wherein the bi-directional pump is inactive when neither the first switch nor the second switch is actuated, and wherein at least one of the first switch and the second switch comprises a resiliently-compressible tube and a pressure-sensitive switch disposed within a void of the resiliently-compressible tube.

2. The system as claimed in claim 1 wherein the syringe is removably connectable to the bi-directional pump.

3. The system as claimed in claim 1 wherein the pump comprises a cloth grabber for use in immobilizing the pump and wherein the cloth grabber comprises a member shaped to include a transverse opening and at least one resilient finger, the at least one resilient finger defining, in part, the transverse opening.

4. The system as claimed in claim 1 further comprising a control device for automatically preventing the fluid pressure in the infusion needle from exceeding a predetermined threshold.

5. The system as claimed in claim 4 wherein the predetermined threshold is 10 psi to 20 psi.

6. The system as claimed in claim 4 wherein the control device comprises a pressure relief valve that bleeds fluid when the fluid pressure approaches the predetermined threshold.

7. The system as claimed in claim 4 wherein the control device comprises a pressure sensor and a switch for cutting off power to the bi-directional pump when the fluid pressure exceeds the predetermined threshold.

8. The system as claimed in claim 7 wherein the syringe further comprises a seal, wherein the seal is deformable by fluid pressure, and wherein the pressure sensor comprises a first component coupled to the syringe plunger and a second component coupled to the seal.

9. The system as claimed in claim 7 wherein the control device further comprises means for continuously measuring and reporting one or more fluid characteristics.

10. The system as claimed in claim 4 wherein the control device comprises a maximum torque limiter.

11. The system as claimed in claim 10 wherein the maximum torque limiter comprises a current sensor, a resistor and a shutoff switch.

12. The system as claimed in claim 1 wherein the fluid within the syringe has a fluid pressure, wherein the bi-directional pump comprises a motor, the motor drawing a motor current, and wherein the motor current is proportional to the fluid pressure within the syringe, the system further comprising a control device for preventing the fluid pressure within the syringe from exceeding a maximum value, the control device comprising circuitry that senses the current of the motor and that controls the motor based on the sensed current of the motor.

13. The system as claimed in claim 1 wherein the bi-directional pump comprises a DC motor, the system further comprising at least one battery for powering the DC motor.

14. A method for controllably administering fluid to a patient and/or for controllably withdrawing fluid from the patient, the method comprising:

providing the system of claim 1;

positioning the infusion needle at a desired location within the patient;

using the hands-free switch to activate and to deactivate the bi-directional pump.

15. The method as claimed in claim 14 wherein the system further comprises a control device for automatically preventing the fluid pressure in the infusion needle from exceeding a predetermined threshold.

16. A system for controllably administering fluid to a patient and/or for controllably withdrawing fluid from the patient, the system comprising:

a syringe/pump assembly, the syringe/pump assembly comprising a syringe, the syringe comprising a syringe body and a syringe plunger, the syringe plunger comprising a column portion having a proximal end and a distal end, the syringe plunger further comprising a handle disposed at the proximal end of the column portion, the distal end of the column portion being insertable into the syringe body, the column portion comprising a rack extending along a length of the column portion, a housing, the housing comprising a top wall adapted to support the syringe body, the top wall comprising a first transverse opening and a second transverse opening, a bi-directional pump, the bi-directional pump comprising a motor and a gear, the motor being disposed within the housing, the gear being coupled to the motor and extending through the first transverse opening in the top wall of the housing, the gear being engageable with the rack of the syringe plunger for driving the rack so as to move the syringe plunger relative to the syringe body to alternately produce positive and negative fluid flow in the infusion needle, an adaptor, the adaptor being coupled to the syringe and comprising a projection, and a locking clip mounted on the housing, the locking clip extending through the second transverse opening and releasably engaging the projection of the adaptor;

an infusion needle, the infusion needle being operatively coupled to the syringe; and a hands-free switch for activating and/or deactivating the motor.

17. The system as claimed in claim 16 wherein the hands-free switch comprises a resiliently-compressible tube and a pressure-sensitive switch disposed within a void of the resiliently-compressible tube.

18. The system as claimed in claim 16 further comprising a control device for automatically preventing the fluid pressure in the infusion needle from exceeding a predetermined threshold.

19. The system as claimed in claim 18 wherein the predetermined threshold is 10 psi to 20 psi.

20. The system as claimed in claim 18 wherein the control device comprises a pressure sensor and a switch for cutting off power to the pump when the fluid pressure exceeds the predetermined threshold.

21. The system as claimed in claim 20 wherein the syringe further comprises a seal, wherein the seal is deformable by fluid pressure, and wherein the pressure sensor comprises a first component coupled to the syringe plunger and a second component coupled to the seal.

22. The system as claimed in claim 20 wherein the control device further comprises means for continuously measuring and reporting one or more fluid characteristics.

23. The system as claimed in claim 18 wherein the control device comprises a maximum torque limiter.

24. The system as claimed in claim 23 wherein the maximum torque limiter comprises a current sensor, a resistor and a shutoff switch.

25. The system as claimed in claim 16 wherein the top wall of the housing further comprises a first depression, the first depression being arcuate and being sized and shaped to matingly receive the syringe body.

26. The system as claimed in claim 25 wherein the top wall of the housing further comprises a second depression, wherein the second depression includes a portion that is sized and shaped to matingly receive the projection of the adaptor.

27. The system as claimed in claim 26 wherein the second depression further comprises a projection and wherein the adaptor further comprises a spring tab for resiliently engaging the projection of the second depression.

28. The system as claimed in claim 16 wherein the locking clip comprises a block and a pawl, wherein the block is disposed within an aperture of the housing, and wherein the pawl is coupled to the block and is shaped to mate with the projection of the adaptor.

29. The system as claimed in claim 28 wherein the projection of the adaptor is shaped to include an opening and wherein the pawl of the locking clip is insertable into the opening of the projection.

30. The system as claimed in claim 29 wherein the locking clip is slidably mounted on the housing for movement between a locked position in which the pawl mates with the projection of the adaptor, thereby securing the adaptor to the housing, and a released position in which the pawl is removed from the projection of the adaptor, thereby enabling the adaptor to be removed from the housing.

31. The system as claimed in claim 30 further comprising a spring, the spring being mounted on the locking clip for biasing the locking clip towards the locked position.

32. The system as claimed in claim 16 wherein the hands-free switch comprises a pedal assembly, wherein the pedal assembly comprises a first switch and a second switch, wherein actuation of the first switch causes the bi-directional pump to expel fluid from the syringe body, wherein actuation of the second switch causes the bi-directional pump to draw fluid into the syringe body, and wherein the bi-directional pump is inactive when neither the first switch nor the second switch is actuated.

* * * * *